US012558033B2

(12) United States Patent
Telfort et al.

(10) Patent No.: US 12,558,033 B2
(45) Date of Patent: *Feb. 24, 2026

(54) ACOUSTIC RESPIRATORY MONITORING SENSOR HAVING MULTIPLE SENSING ELEMENTS

(71) Applicant: Masimo Corporation, Irvine, CA (US)

(72) Inventors: Valery G. Telfort, Irvine, CA (US);
Dimitar Dimitrov, Saint-Laurent (CA);
Phi Trang, Montreal (CA)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/652,083

(22) Filed: May 1, 2024

(65) Prior Publication Data

US 2024/0285238 A1     Aug. 29, 2024

Related U.S. Application Data

(63) Continuation of application No. 17/144,770, filed on Jan. 8, 2021, now Pat. No. 11,998,362, which is a
(Continued)

(51) Int. Cl.
*A61B 5/00*          (2006.01)
*A61B 7/00*          (2006.01)
(Continued)

(52) U.S. Cl.
CPC ............ *A61B 5/7214* (2013.01); *A61B 7/003* (2013.01); *A61B 7/008* (2013.01); *A61B 7/04* (2013.01);
(Continued)

(58) Field of Classification Search
None
See application file for complete search history.

(56) References Cited

U.S. PATENT DOCUMENTS

| | | |
|---|---|---|
| 2,699,465 A | 1/1955 | Hamilton |
| 3,399,467 A | 9/1968 | Ravin |

(Continued)

FOREIGN PATENT DOCUMENTS

| | | |
|---|---|---|
| CA | 2490438 | 1/2004 |
| CA | 2262236 | 4/2008 |

(Continued)

OTHER PUBLICATIONS

US 8,740,816 B2, 06/2014, Telfort et al. (withdrawn)
(Continued)

*Primary Examiner* — Michael R Bloch
(74) *Attorney, Agent, or Firm* — Knobbe, Martens, Olson & Bear, LLP

(57) ABSTRACT
According to certain described aspects, multiple acoustic sensing elements are employed in a variety of beneficial ways to provide improved physiological monitoring, among other advantages. In various embodiments, sensing elements can be advantageously employed in a single sensor package, in multiple sensor packages, and at a variety of other strategic locations in the monitoring environment. According to other aspects, to compensate for skin elasticity and attachment variability, an acoustic sensor support is provided that includes one or more pressure equalization pathways. The pathways can provide an air-flow channel from the cavity defined by the sensing elements and frame to the ambient air pressure.

20 Claims, 35 Drawing Sheets

Related U.S. Application Data continuation of application No. 16/193,756, filed on
Nov. 16, 2018, now Pat. No. 10,925,544, which is a
continuation of application No. 15/366,899, filed on
Dec. 1, 2016, now Pat. No. 10,349,895, which is a
continuation of application No. 14/247,120, filed on
Apr. 7, 2014, now Pat. No. 9,538,980, which is a
continuation of application No. 12/904,931, filed on
Oct. 14, 2010, now Pat. No. 8,690,799.

(60) Provisional application No. 61/313,645, filed on Mar.
12, 2010, provisional application No. 61/252,099,
filed on Oct. 15, 2009.

(51) Int. Cl.
| A61B 7/04 | (2006.01) |
| A61B 5/0205 | (2006.01) |
| A61B 5/024 | (2006.01) |
| A61B 5/08 | (2006.01) |
| A61B 5/145 | (2006.01) |

(52) U.S. Cl.
CPC ........... A61B 5/0006 (2013.01); A61B 5/0205
(2013.01); A61B 5/02438 (2013.01); A61B
5/02444 (2013.01); A61B 5/08 (2013.01);
A61B 5/0816 (2013.01); A61B 5/082
(2013.01); A61B 5/145 (2013.01); A61B
5/4818 (2013.01); A61B 5/6822 (2013.01);
A61B 5/6833 (2013.01); A61B 5/721
(2013.01); A61B 2560/0412 (2013.01); A61B
2562/0204 (2013.01); A61B 2562/182
(2013.01); A61B 2562/222 (2013.01); A61B
2562/227 (2013.01); Y10T 29/49005 (2015.01)

(56)                    References Cited

U.S. PATENT DOCUMENTS

| | | | |
|---|---|---|---|
| 6,040,578 A | 3/2000 | Malin et al. |
| 6,045,509 A | 4/2000 | Caro et al. |
| 6,048,323 A | 4/2000 | Hon |
| 6,066,204 A | 5/2000 | Haven |
| 6,067,462 A | 5/2000 | Diab et al. |
| 6,081,735 A | 6/2000 | Diab et al. |
| 6,083,156 A | 7/2000 | Lisiecki |
| 6,088,607 A | 7/2000 | Diab et al. |
| 6,091,973 A | 7/2000 | Colla et al. |
| 6,106,481 A | 8/2000 | Cohen |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,168,568 B1 | 1/2001 | Gavriely |
| 6,178,343 B1 | 1/2001 | Bindszus et al. |
| 6,184,521 B1 | 2/2001 | Coffin, IV et al. |
| 6,206,830 B1 | 3/2001 | Diab et al. |
| 6,210,344 B1 | 4/2001 | Perin et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,261,237 B1 | 7/2001 | Swanson et al. |
| 6,261,238 B1 | 7/2001 | Gavriely |
| 6,263,222 B1 | 7/2001 | Diab et al. |
| 6,271,760 B1 | 8/2001 | Watanabe et al. |
| 6,275,594 B1 | 8/2001 | Senoo et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,295,365 B1 | 9/2001 | Ota |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,014 B1 | 6/2002 | Toda |
| 6,411,373 B1 | 6/2002 | Garside et al. |
| 6,415,033 B1 | 7/2002 | Halleck et al. |
| 6,415,167 B1 | 7/2002 | Blank et al. |
| 6,423,013 B1 | 7/2002 | Bakker et al. |
| 6,430,437 B1 | 8/2002 | Marro |
| 6,430,525 B1 | 8/2002 | Weber et al. |
| 6,438,238 B1 | 8/2002 | Callahan |
| 6,463,311 B1 | 10/2002 | Diab |
| 6,470,199 B1 | 10/2002 | Kopotic et al. |
| 6,486,588 B2 | 11/2002 | Doron et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,560,470 B1 | 5/2003 | Pologe |
| 6,571,113 B1 | 5/2003 | Fein et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,702,755 B1 | 3/2004 | Stasz et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,074 B1 | 4/2004 | Kästle |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,816,744 B2 | 11/2004 | Garfield et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,869,402 B2 | 3/2005 | Arnold |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,937,736 B2 | 8/2005 | Toda |
| 6,939,305 B2 | 9/2005 | Flaherty et al. |
| 6,943,348 B1 | 9/2005 | Coffin IV |
| 6,950,687 B2 | 9/2005 | Al-Ali |
| 6,954,971 B1 | 10/2005 | Bryant et al. |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |

(56)          References Cited

U.S. PATENT DOCUMENTS

| | | | |
|---|---|---|---|
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,020,508 | B2 | 3/2006 | Stivoric et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,035,684 | B2 | 4/2006 | Lee |
| 7,039,449 | B2 | 5/2006 | Al-Ali |
| 7,041,060 | B2 | 5/2006 | Flaherty et al. |
| 7,044,918 | B2 | 5/2006 | Diab |
| 7,048,687 | B1 | 5/2006 | Reuss et al. |
| 7,067,893 | B2 | 6/2006 | Mills et al. |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| 7,096,060 | B2 | 8/2006 | Arand et al. |
| 7,110,804 | B2 | 9/2006 | Baumer et al. |
| D529,616 | S | 10/2006 | Deros et al. |
| 7,132,641 | B2 | 11/2006 | Schulz et al. |
| 7,133,710 | B2 | 11/2006 | Acosta et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,190,945 | B1 | 3/2007 | Crisafulli |
| 7,215,984 | B2 | 5/2007 | Diab et al. |
| 7,215,986 | B2 | 5/2007 | Diab et al. |
| 7,221,971 | B2 | 5/2007 | Diab et al. |
| 7,225,006 | B2 | 5/2007 | Al-Ali et al. |
| 7,225,007 | B2 | 5/2007 | Al-Ali et al. |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,246,069 | B1 | 7/2007 | O'Hanlon et al. |
| 7,254,429 | B2 | 8/2007 | Schurman et al. |
| 7,254,431 | B2 | 8/2007 | Al-Ali et al. |
| 7,254,433 | B2 | 8/2007 | Diab et al. |
| 7,254,434 | B2 | 8/2007 | Schulz et al. |
| 7,270,126 | B2 | 9/2007 | Wallace et al. |
| 7,272,425 | B2 | 9/2007 | Al-Ali |
| 7,274,955 | B2 | 9/2007 | Kiani et al. |
| D554,263 | S | 10/2007 | Al-Ali et al. |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,361,148 | B2 | 4/2008 | Narimatsu |
| 7,368,855 | B2 | 5/2008 | Orten |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Al-Ali et al. |
| 7,377,899 | B2 | 5/2008 | Weber et al. |
| 7,383,070 | B2 | 6/2008 | Diab et al. |
| 7,395,158 | B2 | 7/2008 | Monfre et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,457,757 | B1 | 11/2008 | McNeill |
| 7,467,002 | B2 | 12/2008 | Weber et al. |
| 7,469,157 | B2 | 12/2008 | Diab et al. |
| 7,469,158 | B2 | 12/2008 | Cutler et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,514,725 | B2 | 4/2009 | Wojtczuk et al. |
| 7,515,044 | B2 | 4/2009 | Welch et al. |
| 7,519,406 | B2 | 4/2009 | Blank et al. |
| 7,526,328 | B2 | 4/2009 | Diab et al. |
| D592,507 | S | 5/2009 | Wachman et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,618,375 | B2 | 11/2009 | Flaherty et al. |
| 7,620,674 | B2 | 11/2009 | Ruchti et al. |
| D606,659 | S | 12/2009 | Kiani et al. |
| 7,625,117 | B2 | 12/2009 | Haslett et al. |
| 7,629,039 | B2 | 12/2009 | Eckerbom et al. |
| 7,640,140 | B2 | 12/2009 | Ruchti et al. |
| 7,647,083 | B2 | 1/2010 | Al-Ali et al. |
| D609,193 | S | 2/2010 | Al-Ali et al. |
| 7,662,105 | B2 | 2/2010 | Hatlestad |
| 7,668,588 | B2 | 2/2010 | Kovacs |
| D614,305 | S | 4/2010 | Al-Ali et al. |
| 7,697,966 | B2 | 4/2010 | Monfre et al. |
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,783,056 | B2 | 8/2010 | Wilmink |
| 7,791,155 | B2 | 9/2010 | Diab |
| 7,801,581 | B2 | 9/2010 | Diab |
| 7,806,226 | B2 | 10/2010 | Drummond et al. |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,860,553 | B2 | 12/2010 | Govari et al. |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,903,825 | B1 | 3/2011 | Melanson |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,940,937 | B2 | 5/2011 | Smith |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |

(56)                    References Cited

U.S. PATENT DOCUMENTS

| | | | |
|---|---|---|---|
| 7,976,480 | B2 | 7/2011 | Grajales et al. |
| 7,988,637 | B2 | 8/2011 | Diab |
| 7,988,688 | B2 | 8/2011 | Webb et al. |
| 7,990,382 | B2 | 8/2011 | Kiani |
| 7,991,165 | B2 | 8/2011 | Kassal et al. |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| 8,092,396 | B2 | 1/2012 | Bagha et al. |
| 8,108,039 | B2 | 1/2012 | Saliga et al. |
| RE43,169 | E | 2/2012 | Parker |
| 8,116,841 | B2 | 2/2012 | Bly et al. |
| 8,118,620 | B2 | 2/2012 | Al-Ali et al. |
| 8,121,673 | B2 | 2/2012 | Tran |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,214,007 | B2 | 7/2012 | Baker et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,532 | B2 | 7/2012 | Davis |
| 8,229,533 | B2 | 7/2012 | Diab et al. |
| 8,233,955 | B2 | 7/2012 | Al-Ali et al. |
| 8,241,223 | B2 | 8/2012 | Gavriely et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,291 | B2 | 9/2012 | Bridger et al. |
| 8,265,723 | B1 | 9/2012 | McHale et al. |
| 8,274,360 | B2 | 9/2012 | Sampath et al. |
| 8,275,140 | B2 | 9/2012 | Smith |
| 8,280,473 | B2 | 10/2012 | Al-Ali |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| 8,320,576 | B1 | 11/2012 | Abbruscato |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-Ali et al. |
| 8,385,996 | B2 | 2/2013 | Smith et al. |
| 8,388,353 | B2 | 3/2013 | Kiani et al. |
| 8,396,228 | B2 | 3/2013 | Bilan |
| 8,399,822 | B2 | 3/2013 | Al-Ali |
| 8,401,602 | B2 | 3/2013 | Kiani |
| 8,403,865 | B2 | 3/2013 | Halperin et al. |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,449,469 | B2 | 5/2013 | Banet et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellott et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,491,489 | B2 | 7/2013 | Shin et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,517,981 | B2 | 8/2013 | Zornow |
| 8,523,781 | B2 | 9/2013 | Al-Ali |
| 8,526,665 | B2 | 9/2013 | Lutz et al. |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,600,467 | B2 | 12/2013 | Al-Ali et al. |
| 8,606,342 | B2 | 12/2013 | Diab |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,595 | B2 | 2/2014 | Basinger |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,688,183 | B2 | 4/2014 | Bruinsma et al. |
| 8,688,189 | B2 | 4/2014 | Shennib |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |

(56)                References Cited

U.S. PATENT DOCUMENTS 8,740,792  B1    6/2014  Kiani et al.
8,754,776  B2    6/2014  Poeze et al.
8,755,535  B2    6/2014  Telfort et al.
8,755,856  B2    6/2014  Diab et al.
8,755,872  B1    6/2014  Marinow
8,761,850  B2    6/2014  Lamego
8,764,671  B2    7/2014  Kiani
8,768,423  B2    7/2014  Shakespeare et al.
8,771,204  B2    7/2014  Telfort et al.
8,777,634  B2    7/2014  Kiani et al.
8,781,543  B2    7/2014  Diab et al.
8,781,544  B2    7/2014  Al-Ali et al.
8,781,549  B2    7/2014  Al-Ali et al.
8,788,003  B2    7/2014  Schurman et al.
8,790,268  B2    7/2014  Al-Ali
8,801,613  B2    8/2014  Al-Ali et al.
8,821,397  B2    9/2014  Al-Ali et al.
8,821,415  B2    9/2014  Al-Ali et al.
8,830,449  B1    9/2014  Lamego et al.
8,831,700  B2    9/2014  Schurman et al.
8,840,549  B2    9/2014  Al-Ali et al.
8,847,740  B2    9/2014  Kiani et al.
8,849,365  B2    9/2014  Smith et al.
8,852,094  B2   10/2014  Al-Ali et al.
8,852,994  B2   10/2014  Wojtczuk et al.
8,868,147  B2   10/2014  Stippick et al.
8,868,150  B2   10/2014  Al-Ali et al.
8,870,792  B2   10/2014  Al-Ali et al.
8,886,271  B2   11/2014  Kiani et al.
8,888,539  B2   11/2014  Al-Ali et al.
8,888,708  B2   11/2014  Diab et al.
8,892,180  B2   11/2014  Weber et al.
8,897,847  B2   11/2014  Al-Ali
8,909,310  B2   12/2014  Lamego et al.
8,911,377  B2   12/2014  Al-Ali
8,912,909  B2   12/2014  Al-Ali et al.
8,920,317  B2   12/2014  Al-Ali et al.
8,921,699  B2   12/2014  Al-Ali et al.
8,922,382  B2   12/2014  Al-Ali et al.
8,929,964  B2    1/2015  Al-Ali et al.
8,942,777  B2    1/2015  Diab et al.
8,948,834  B2    2/2015  Diab et al.
8,948,835  B2    2/2015  Diab
8,961,413  B2    2/2015  Teller et al.
8,965,471  B2    2/2015  Lamego
8,983,564  B2    3/2015  Al-Ali
8,989,831  B2    3/2015  Al-Ali et al.
8,996,085  B2    3/2015  Kiani et al.
8,998,809  B2    4/2015  Kiani
9,028,429  B2    5/2015  Telfort et al.
9,037,207  B2    5/2015  Al-Ali et al.
9,060,721  B2    6/2015  Reichgott et al.
9,066,666  B2    6/2015  Kiani
9,066,680  B1    6/2015  Al-Ali et al.
9,072,474  B2    7/2015  Al-Ali et al.
9,078,560  B2    7/2015  Schurman et al.
9,084,569  B2    7/2015  Weber et al.
9,095,316  B2    8/2015  Welch et al.
9,106,038  B2    8/2015  Telfort et al.
9,107,625  B2    8/2015  Telfort et al.
9,107,626  B2    8/2015  Al-Ali et al.
9,113,831  B2    8/2015  Al-Ali
9,113,832  B2    8/2015  Al-Ali
9,119,595  B2    9/2015  Lamego
9,131,881  B2    9/2015  Diab et al.
9,131,882  B2    9/2015  Al-Ali et al.
9,131,883  B2    9/2015  Al-Ali
9,131,917  B2    9/2015  Telfort et al.
9,138,180  B1    9/2015  Coverston et al.
9,138,182  B2    9/2015  Al-Ali et al.
9,138,192  B2    9/2015  Weber et al.
9,142,117  B2    9/2015  Muhsin et al.
9,153,112  B1   10/2015  Kiani et al.
9,153,121  B2   10/2015  Kiani et al.
9,161,696  B2   10/2015  Al-Ali et al.

9,161,713  B2   10/2015  Al-Ali et al.
9,167,995  B2   10/2015  Lamego et al.
9,176,141  B2   11/2015  Al-Ali et al.
9,186,102  B2   11/2015  Bruinsma et al.
9,192,312  B2   11/2015  Al-Ali
9,192,329  B2   11/2015  Al-Ali
9,192,351  B1   11/2015  Telfort et al.
9,195,385  B2   11/2015  Al-Ali et al.
9,211,072  B2   12/2015  Kiani
9,211,095  B1   12/2015  Al-Ali
9,218,454  B2   12/2015  Kiani et al.
9,226,696  B2    1/2016  Kiani
9,241,662  B2    1/2016  Al-Ali et al.
9,245,668  B1    1/2016  Vo et al.
9,259,185  B2    2/2016  Abdul-Hafiz et al.
9,267,572  B2    2/2016  Barker et al.
9,277,880  B2    3/2016  Poeze et al.
9,289,167  B2    3/2016  Diab et al.
9,295,421  B2    3/2016  Kiani et al.
9,307,928  B1    4/2016  Al-Ali et al.
9,323,894  B2    4/2016  Kiani
D755,392   S     5/2016  Hwang et al.
9,326,712  B1    5/2016  Kiani
9,333,316  B2    5/2016  Kiani
9,339,220  B2    5/2016  Lamego et al.
9,341,565  B2    5/2016  Lamego et al.
9,351,673  B2    5/2016  Diab et al.
9,351,675  B2    5/2016  Al-Ali et al.
9,364,181  B2    6/2016  Kiani et al.
9,368,671  B2    6/2016  Wojtczuk et al.
9,370,325  B2    6/2016  Al-Ali et al.
9,370,326  B2    6/2016  McHale et al.
9,370,335  B2    6/2016  Al-Ali et al.
9,375,185  B2    6/2016  Ali et al.
9,386,953  B2    7/2016  Al-Ali
9,386,961  B2    7/2016  Al-Ali et al.
9,392,945  B2    7/2016  Al-Ali et al.
9,397,448  B2    7/2016  Al-Ali et al.
9,408,542  B1    8/2016  Kinast et al.
9,411,936  B2    8/2016  Landrum et al.
9,436,645  B2    9/2016  Al-Ali et al.
9,439,599  B2    9/2016  Thompson
9,445,759  B1    9/2016  Lamego et al.
9,466,919  B2   10/2016  Kiani et al.
9,474,474  B2   10/2016  Lamego et al.
9,480,422  B2   11/2016  Al-Ali
9,480,435  B2   11/2016  Olsen
9,492,110  B2   11/2016  Al-Ali et al.
9,510,779  B2   12/2016  Poeze et al.
9,517,024  B2   12/2016  Kiani et al.
9,532,722  B2    1/2017  Lamego et al.
9,538,949  B2    1/2017  Al-Ali et al.
9,538,980  B2    1/2017  Telfort et al.
9,549,696  B2    1/2017  Lamego et al.
9,554,737  B2    1/2017  Schurman et al.
9,560,996  B2    2/2017  Kiani
9,560,998  B2    2/2017  Al-Ali et al.
9,566,019  B2    2/2017  Al-Ali et al.
9,579,039  B2    2/2017  Jansen et al.
9,591,975  B2    3/2017  Dalvi et al.
9,622,692  B2    4/2017  Lamego et al.
9,622,693  B2    4/2017  Diab
D788,312   S     5/2017  Al-Ali et al.
9,636,055  B2    5/2017  Al Ali et al.
9,636,056  B2    5/2017  Al-Ali
9,649,054  B2    5/2017  Lamego et al.
9,662,052  B2    5/2017  Al-Ali et al.
9,668,679  B2    6/2017  Schurman et al.
9,668,680  B2    6/2017  Bruinsma et al.
9,668,703  B2    6/2017  Al-Ali
9,675,286  B2    6/2017  Diab
9,687,160  B2    6/2017  Kiani
9,693,719  B2    7/2017  Al-Ali et al.
9,693,737  B2    7/2017  Al-Ali
9,697,928  B2    7/2017  Al-Ali et al.
9,717,425  B2    8/2017  Kiani et al.
9,717,458  B2    8/2017  Lamego et al.
9,724,016  B1    8/2017  Al-Ali et al.
9,724,024  B2    8/2017  Al-Ali

(56)                    References Cited

U.S. PATENT DOCUMENTS

| | | | |
|---|---|---|---|
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| 9,968,266 B2 | 5/2018 | An et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Ai-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,349,895 B2 | 7/2019 | Telfort et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |

(56) References Cited

U.S. PATENT DOCUMENTS

| | | | |
|---|---|---|---|
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 12,207,901 B1 | 1/2025 | Lapotko et al. |
| D1,060,680 S | 2/2025 | Al-Ali et al. |
| D1,061,585 S | 2/2025 | Ndort |
| D1,063,893 S | 2/2025 | DeJong et al. |
| 12,220,207 B2 | 2/2025 | Telfort et al. |
| 12,235,941 B2 | 2/2025 | Kiani et al. |
| 12,236,767 B2 | 2/2025 | Muhsin |
| D1,066,244 S | 3/2025 | Lim et al. |
| D1,066,672 S | 3/2025 | Al-Ali et al. |
| D1,072,837 S | 4/2025 | Ahmed et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2002/0193670 A1 | 12/2002 | Garfield et al. |
| 2003/0013975 A1 | 1/2003 | Kiani |
| 2003/0018243 A1 | 1/2003 | Gerhardt et al. |
| 2003/0135087 A1 | 7/2003 | Hickle et al. |
| 2003/0144582 A1 | 7/2003 | Cohen et al. |
| 2003/0149349 A1 | 8/2003 | Jensen |
| 2003/0156288 A1 | 8/2003 | Barnum et al. |
| 2003/0196660 A1 | 10/2003 | Haveri |
| 2003/0212312 A1 | 11/2003 | Coffin, IV et al. |
| 2004/0015093 A1 | 1/2004 | Knapp, II et al. |
| 2004/0106163 A1 | 6/2004 | Workman, Jr. et al. |
| 2004/0133087 A1 | 7/2004 | Ali et al. |
| 2004/0149282 A1 | 8/2004 | Hickle |
| 2004/0158162 A1 | 8/2004 | Narimatsu |
| 2004/0167416 A1 | 8/2004 | Lee |
| 2004/0215094 A1 | 10/2004 | Baumer et al. |
| 2004/0226771 A1 | 11/2004 | Werblud |
| 2004/0228494 A1 | 11/2004 | Smith |
| 2004/0243016 A1 | 12/2004 | Sanderson |
| 2005/0033128 A1 | 2/2005 | Ali et al. |
| 2005/0055276 A1 | 3/2005 | Kiani et al. |
| 2005/0065417 A1 | 3/2005 | Ali et al. |
| 2005/0114455 A1 | 5/2005 | Conroy et al. |
| 2005/0123071 A1 | 6/2005 | Okada |
| 2005/0234317 A1 | 10/2005 | Kiani |
| 2005/0283059 A1 | 12/2005 | Vijay et al. |
| 2006/0047215 A1 | 3/2006 | Newman et al. |
| 2006/0059324 A1 | 3/2006 | Simske et al. |
| 2006/0073719 A1 | 4/2006 | Kiani |
| 2006/0094943 A1 | 5/2006 | Van Slyke |
| 2006/0144397 A1 | 7/2006 | Wallace et al. |
| 2006/0155167 A1 | 7/2006 | Elliott |
| 2006/0161054 A1 | 7/2006 | Reuss et al. |
| 2006/0184052 A1 | 8/2006 | Iwasawa |
| 2006/0189871 A1 | 8/2006 | Al-Ali et al. |
| 2006/0190051 A1 | 8/2006 | Gerber et al. |
| 2006/0198533 A1 | 9/2006 | Wang |
| 2006/0238333 A1 | 10/2006 | Welch et al. |
| 2006/0264767 A1 | 11/2006 | Shennib |
| 2007/0016030 A1 | 1/2007 | Stringer |
| 2007/0049837 A1* | 3/2007 | Shertukde ............. G01H 11/08 |
| | | 600/528 |
| 2007/0056582 A1 | 3/2007 | Wood et al. |
| 2007/0058818 A1 | 3/2007 | Yoshimine |
| 2007/0073116 A1 | 3/2007 | Kiani et al. |
| 2007/0106179 A1 | 5/2007 | Bagha et al. |
| 2007/0118054 A1 | 5/2007 | Pinhas |
| 2007/0135725 A1 | 6/2007 | Hatlestad |
| 2007/0147639 A1 | 6/2007 | Richardson et al. |

(56) References Cited

U.S. PATENT DOCUMENTS

| | | |
|---|---|---|
| 2007/0165872 A1 | 7/2007 | Bridger et al. |
| 2007/0167855 A1 | 7/2007 | Shin et al. |
| 2007/0173730 A1 | 7/2007 | Bikko |
| 2007/0180140 A1 | 8/2007 | Welch et al. |
| 2007/0185397 A1 | 8/2007 | Govari et al. |
| 2007/0208262 A1 | 9/2007 | Kovacs |
| 2007/0208267 A1 | 9/2007 | Schmid |
| 2007/0244377 A1 | 10/2007 | Cozad et al. |
| 2007/0255153 A1 | 11/2007 | Kumar et al. |
| 2007/0282174 A1 | 12/2007 | Sabatino |
| 2007/0282478 A1 | 12/2007 | Al-Ali et al. |
| 2008/0039735 A1 | 2/2008 | Hickerson |
| 2008/0064965 A1 | 3/2008 | Jay et al. |
| 2008/0076972 A1 | 3/2008 | Dorogusker et al. |
| 2008/0077026 A1 | 3/2008 | Banet et al. |
| 2008/0077198 A1 | 3/2008 | Webb et al. |
| 2008/0077435 A1 | 3/2008 | Muradia |
| 2008/0093157 A1 | 4/2008 | Drummond et al. |
| 2008/0094228 A1 | 4/2008 | Welch et al. |
| 2008/0097249 A1 | 4/2008 | Pool et al. |
| 2008/0103375 A1 | 5/2008 | Kiani |
| 2008/0114220 A1 | 5/2008 | Banet et al. |
| 2008/0137876 A1 | 6/2008 | Kassal et al. |
| 2008/0139953 A1 | 6/2008 | Baker et al. |
| 2008/0143496 A1 | 6/2008 | Linjama |
| 2008/0162123 A1 | 7/2008 | Goldin |
| 2008/0188733 A1 | 8/2008 | Al-Ali et al. |
| 2008/0188760 A1 | 8/2008 | Al-Ali et al. |
| 2008/0219464 A1 | 9/2008 | Smith |
| 2008/0221418 A1 | 9/2008 | Al-Ali et al. |
| 2008/0251313 A1 | 10/2008 | Knight et al. |
| 2008/0281219 A1 | 11/2008 | Glickman et al. |
| 2008/0310652 A1 | 12/2008 | Gustabsson |
| 2009/0018409 A1 | 1/2009 | Banet et al. |
| 2009/0018429 A1 | 1/2009 | Saliga et al. |
| 2009/0036759 A1 | 2/2009 | Ault et al. |
| 2009/0076363 A1 | 3/2009 | Bly et al. |
| 2009/0093687 A1 | 4/2009 | Telfort et al. |
| 2009/0095926 A1 | 4/2009 | MacNeish, III |
| 2009/0170664 A1 | 7/2009 | Shirasaki et al. |
| 2009/0187065 A1 | 7/2009 | Basinger |
| 2009/0247924 A1 | 10/2009 | Lamego et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0299157 A1 | 12/2009 | Telfort et al. |
| 2009/0299742 A1 | 12/2009 | Toman et al. |
| 2009/0316925 A1 | 12/2009 | Eisenfeld et al. |
| 2010/0004518 A1 | 1/2010 | Vo et al. |
| 2010/0030040 A1 | 2/2010 | Poeze et al. |
| 2010/0069725 A1 | 3/2010 | Al-Ali |
| 2010/0090901 A1 | 4/2010 | Smith et al. |
| 2010/0094096 A1 | 4/2010 | Petruzzelli et al. |
| 2010/0099964 A1 | 4/2010 | O'Reilly et al. |
| 2010/0179438 A1 | 7/2010 | Heneghan |
| 2010/0195864 A1 | 8/2010 | Lutz et al. |
| 2010/0196861 A1 | 8/2010 | Lunner |
| 2010/0204996 A1 | 8/2010 | Zeng et al. |
| 2010/0232615 A1 | 9/2010 | Sörlander et al. |
| 2010/0234718 A1 | 9/2010 | Sampath et al. |
| 2010/0256505 A1 | 10/2010 | Xu |
| 2010/0261979 A1 | 10/2010 | Al-Ali et al. |
| 2010/0270257 A1 | 10/2010 | Wachman et al. |
| 2010/0305416 A1 | 12/2010 | Bédard et al. |
| 2010/0317936 A1 | 12/2010 | Al-Ali et al. |
| 2011/0001605 A1 | 1/2011 | Kiani et al. |
| 2011/0028802 A1 | 2/2011 | Addison |
| 2011/0028806 A1 | 2/2011 | Merritt et al. |
| 2011/0028809 A1 | 2/2011 | Goodman |
| 2011/0034831 A1 | 2/2011 | Christensen et al. |
| 2011/0040197 A1 | 2/2011 | Welch et al. |
| 2011/0066062 A1 | 3/2011 | Banet et al. |
| 2011/0082711 A1 | 4/2011 | Poeze et al. |
| 2011/0087081 A1 | 4/2011 | Kiani et al. |
| 2011/0087083 A1 | 4/2011 | Poeze et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0172561 A1 | 7/2011 | Al-Ali et al. |
| 2011/0172967 A1 | 7/2011 | Al-Ali et al. |
| 2011/0196211 A1 | 8/2011 | Al-Ali et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0213273 A1 | 9/2011 | Telfort et al. |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0279963 A1 | 11/2011 | Kumar et al. |
| 2011/0288383 A1 | 11/2011 | Diab |
| 2011/0288431 A1 | 11/2011 | Alshaer et al. |
| 2011/0301444 A1 | 12/2011 | Al-Ali |
| 2012/0041316 A1 | 2/2012 | Al Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0116175 A1 | 5/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0227739 A1 | 9/2012 | Kiani |
| 2012/0230523 A1 | 9/2012 | Ehrlund |
| 2012/0232427 A1 | 9/2012 | Bakema et al. |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0302920 A1 | 11/2012 | Bridger et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0090567 A1 | 4/2013 | Al-Ali et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0116578 A1 | 5/2013 | An et al. |
| 2013/0162433 A1 | 6/2013 | Muhsin et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |

(56) References Cited

U.S. PATENT DOCUMENTS

| | | |
|---|---|---|
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0309506 A1 | 10/2014 | Lamego et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2014/0371548 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0099998 A1 | 4/2015 | Christensen et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |

(56)  References Cited

U.S. PATENT DOCUMENTS

| | | |
|---|---|---|
| 2017/0042488 A1 | 2/2017 | Muhsin |
| 2017/0055847 A1 | 3/2017 | Kiani et al. |
| 2017/0055851 A1 | 3/2017 | Ai-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0103874 A1 | 4/2018 | Lee et al. |
| 2018/0110478 A1 | 4/2018 | Al-Ali |
| 2018/0125445 A1 | 5/2018 | Telfort et al. |
| 2018/0153446 A1 | 6/2018 | Kiani |
| 2018/0206815 A1 | 7/2018 | Telfort |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0142344 A1 | 5/2019 | Telfort et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0128069 A1 | 5/2021 | Telfort et al. |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Ai-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |

(56)                    References Cited

U.S. PATENT DOCUMENTS

| 2025/0000458 A1 | 1/2025 | Abdul-Hafiz et al. |
| 2025/0037836 A1 | 1/2025 | Kiani |

FOREIGN PATENT DOCUMENTS

| CN | 201497610 | 6/2010 |
| CN | 202005761 | 10/2011 |
| EP | 0 716 628 | 12/1998 |
| EP | 0 659 058 | 1/1999 |
| EP | 0 956 820 | 11/1999 |
| EP | 1 518 442 | 3/2005 |
| EP | 2 014 234 | 1/2009 |
| EP | 1 207 536 | 2/2010 |
| EP | 2 488 106 | 8/2012 |
| EP | 2 488 978 | 8/2012 |
| FR | 2 847 796 | 6/2004 |
| GB | 2 358 546 | 7/2001 |
| JP | S53-094482 | 8/1978 |
| JP | S56-031742 | 3/1981 |
| JP | 60-059900 | 4/1985 |
| JP | 62-014898 | 1/1987 |
| JP | 01-309872 | 12/1989 |
| JP | H04-317637 | 11/1992 |
| JP | H07-152553 | 6/1995 |
| JP | 10-155755 | 6/1998 |
| JP | 2001-50713 | 2/2001 |
| JP | 2003-329719 | 11/2003 |
| JP | 2005-522292 | 7/2005 |
| JP | 2005-531230 | 10/2005 |
| JP | 2012-513872 | 6/2012 |
| JP | 2013-508029 | 3/2013 |
| JP | 2013-508030 | 3/2013 |
| NO | 20040819 | 2/2004 |
| WO | WO 94/005207 | 3/1994 |
| WO | WO 94/013207 | 6/1994 |
| WO | WO 95/029632 | 11/1995 |
| WO | WO 99/053277 | 10/1999 |
| WO | WO 00/010462 | 3/2000 |
| WO | WO 01/034033 | 5/2001 |
| WO | WO 01/087005 | 11/2001 |
| WO | WO 01/097691 | 12/2001 |
| WO | WO 02/003042 | 1/2002 |
| WO | WO 01/078059 | 3/2002 |
| WO | WO 02/024067 | 7/2002 |
| WO | WO 03/058646 | 7/2003 |
| WO | WO 03/087737 | 10/2003 |
| WO | WO 2004/000111 | 12/2003 |
| WO | WO 2004/004411 | 1/2004 |
| WO | WO 2004/078038 | 9/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |
| WO | WO 2009/155593 | 12/2009 |
| WO | WO 2010/078168 | 7/2010 |
| WO | WO 2011/047211 | 4/2011 |
| WO | WO 2011/047213 | 4/2011 |
| WO | WO 2011/047216 | 8/2011 |
| WO | WO 2011/047207 | 9/2011 |
| WO | WO 2011/047209 | 3/2012 |
| WO | WO 2013/056141 | 4/2013 |

OTHER PUBLICATIONS

US 2024/0016391 A1, 01/2024, Lapotko et al. (withdrawn)
U.S. Appl. No. 12/904,836, Bidirectional Physiological Information Display, Sep. 3, 2013.
U.S. Appl. No. 12/904,823, Bidirectional Physiological Information Display, Jul. 29, 2014.
U.S. Appl. No. 14/444,705, Bidirectional Physiological Information Display, Jun. 6, 2017.
U.S. Appl. No. 15/615,654, Bidirectional Physiological Information Display, Jul. 23, 2019.
U.S. Appl. No. 12/643,939, Acoustic Sensor Assembly, Jul. 8, 2014.
U.S. Appl. No. 14/259,527, Acoustic Sensor Assembly, May 12, 2015
U.S. Appl. No. 14/671,367, Acoustic Sensor Assembly, Sep. 15, 2015.
U.S. Appl. No. 14/820,376, Acoustic Sensor Assembly, Oct. 24, 2017.
U.S. Appl. No. 15/709,174, Acoustic Sensor Assembly, Feb. 4, 2020.
U.S. Appl. No. 16/717,082, Acoustic Sensor Assembly, Jan. 24, 2023.
U.S. Appl. No. 12/904,931, Acoustic Respiratory Monitoring Sensor Having Multiple Sensing Elements, Apr. 8, 2014.
U.S. Appl. No. 12/904,890, Acoustic Respiratory Monitoring Sensor Having Multiple Sensing Elements, Apr. 22, 2014.
U.S. Appl. No. 12/904,938, Acoustic Respiratory Monitoring Sensor Having Multiple Sensing Elements, Jun. 17, 2014.
U.S. Appl. No. 12/904,907, Acoustic Respiratory Monitoring Sensor Having Multiple Sensing Elements, May 6, 2014.
U.S. Appl. No. 14/247,120, Acoustic Respiratory Monitoring Sensor Having Multiple Sensing Elements, Jan. 10, 2017.
U.S. Appl. No. 15/366,899, Acoustic Respiratory Monitoring Sensor Having Multiple Sensing Elements, Jul. 16, 2019.
U.S. Appl. No. 16/193,756, Acoustic Respiratory Monitoring Sensor Having Multiple Sensing Elements, Feb. 23, 2021.
U.S. Appl. No. 12/904,789, Acoustic Respiratory Monitoring Systems and Method, Nov. 5, 2019.
U.S. Appl. No. 12/905,036, Physiological Acoustic Monitoring System, Sep. 2, 2014.
U.S. Appl. No. 15/204,773, Physiological Acoustic Monitoring System, Jan. 16, 2018.
U.S. Appl. No. 15/837,642, Physiological Acoustic Monitoring System, Jul. 9, 2019.
U.S. Appl. No. 14/473,831, Physiological Acoustic Monitoring System, Jul. 12, 2016.
U.S. Appl. No. 13/650,775, Physiological Acoustic Monitoring System, Oct. 28, 2014.
U.S. Appl. No. 14/522,474, Physiological Acoustic Monitoring System, Jun. 21, 2016.
U.S. Appl. No. 15/184,951, Physiological Acoustic Monitoring System, Oct. 16, 2018.
U.S. Appl. No. 16/159,395, Physiological Acoustic Monitoring System, Apr. 20, 2021.
U.S. Appl. No. 13/152,259, Opticoustic Sensor, May 3, 2016.
U.S. Appl. No. 14/928,484, Opticoustic Sensor, Oct. 10, 2017.
U.S. Appl. No. 14/030,268, Acoustic Patient Sensor Coupler, May 1, 2018.
U.S. Appl. No. 15/926,555, Acoustic Patient Sensor Coupler, Jun. 1, 2021.
U.S. Appl. No. 14/512,286, Acoustic Sensor With Attachment Portion, Nov. 10, 2020.
U.S. Appl. No. 16/434,979, Bidirectional Physiological Information Display, Jun. 7, 2019.
U.S. Appl. No. 16/717,082, Acoustic Sensor Assembly, Dec. 17, 2019.
U.S. Appl. No. 17/144,770, Acoustic Respiratory Monitoring Sensor Having Multiple Sensing Elements, Jan. 8, 2021.
U.S. Appl. No. 16/600,983, Acoustic Respiratory Monitoring Systems and Method, Oct. 14, 2019.
U.S. Appl. No. 13/554,908, Acoustic Respiratory Monitoring Sensor With Suspended Sensing Unit, Jul. 20, 2012.
U.S. Appl. No. 16/505,437, Physiological Acoustic Monitoring System, Jul. 8, 2019.
U.S. Appl. No. 17/233,206, Physiological Acoustic Monitoring System, Apr. 16, 2021.
U.S. Appl. No. 15/729,178, Opticoustic Sensor, Oct. 10, 2017.
U.S. Appl. No. 17/241,705, Acoustic Patient Sensor Coupler, Apr. 27, 2021.
U.S. Appl. No. 18/638,177, Acoustic Patient Sensor Coupler, Apr. 17, 2024.
U.S. Appl. No. 17/036,896, Acoustic Sensor With Attachment Portion, Sep. 29, 2020.

(56)                    References Cited

OTHER PUBLICATIONS

Analog Devices, "12-Bit Serial Input Multiplying D/A Converter", DAC8043A, Product Data Sheet, Analog Devices, Inc., 2000, pp. 8.
Avago Technologies, "HCNR200 and HCNR201, High-Linearity Analog Optocouplers", Data Sheet, Avago Technologies, Nov. 18, 2008, pp. 19.
Eldor et al., "A device for monitoring ventilation during anesthesia; the paratracheal audible respiratory monitor", Canadian Journal of Anesthesia, 1990, vol. 9, No. 1, p. 95-98.
Office Action for EP Application No. 10779086.7 dated Mar. 5, 2013.
EP Office Action dated May 18, 2011 in application No. 03711767.8.
European Search Report for Application No. 13185148.7 dated Dec. 6, 2013.
International Preliminary Report on Patentability (IPRP) in PCT/US2010/052754, dated Apr. 26, 2012.
International Preliminary Report on Patentability dated Apr. 15, 2014 for PCT Application No. PCT/US2012/060084.
International Preliminary Report on Patentability in PCT/US2010/052763 dated Apr. 17, 2012 in 9 pages.
International Search Report & Written Opinion for PCT/US2010/052756, mailed Feb. 6, 2012; 17 pages.
International Search Report & Written Opinion, PCT Application PCT/US2010/052758, Feb. 10, 2011; 12 pages.
International Search Report & Written Opinion, PCT Application PCT/US2010/058981, Feb. 17, 2011; 11 pages.
International Search Report and Written Opinion dated Dec. 21, 2012 for PCT Application No. PCT/US2012/060084.
International Search Report and Written Opinion for PCT/US2009/042902, mailed Dec. 8, 2009.
International Search Report and Written Opinion in PCT/US2010/052754 mailed Jul. 27, 2011.
International Search Report and Written Opinion in PCT/US2010/052763, mailed May 13, 2011.
International Search Report and Written Opinion received in PCT Application No. PCT/US2010/052760 as mailed Mar. 8, 2011 in 11 pages.
International Search Report and Written Opinion issued in PCT Application No. PCT/US2009/069287, Jun. 30, 2010.
International Search Report, PCT Application PCT/CA2003/000536, Dec. 11, 2003; 2 pages.
Japanese Office Action re Application No. 2007-506626, dated Mar. 1, 2011.
Office Action in Japanese Application No. 2011-544508 mailed Apr. 30, 2014.
PCT Invitation to Pay Fees and Initial Search Report in PCT/US2009/069287, dated Apr. 21, 2010.
PCT Invitation to Pay Fees and Initial Search Report in PCT/US2010/052754, dated Mar. 15, 2011.
PCT Invitation to Pay Fees and Initial Search Report in PCT/US2010/052756, dated Oct. 5, 2011.
Sierra et al., "Monitoring Respiratory Rate based on Tracheal Sounds. First Experiences", Proceedings of the 26the Annual International Conference of the IEEE EMBS, Sep. 1-5, 2004, pp. 317-320.
WelchAllyn "ECG ASIC, ECG 3-lead, 5-lead, 12-lead and RESP Signal Processing, ECG ASIC Part No. 000.91163", May 2001, pp. 84.
White, "Advanced Compression Techniques, Tips & Tricks", Part 1 and Part 2, Dec. 2000 and Jan. 2001 in 7 pages.
Office Action for EP Application No. 10779086.7 dated Jul. 11, 2016.
Office Action for European Patent Application No. 13185148.7 dated Apr. 4, 2017.
Oversampling by Wikipedia, the free encyclopedia, pub. Online Oct. 7, 2012 at "https://wikipedia.org/w/index.php?title=Oversampling&oldid=516454012", accessed Sep. 3, 2015.
Pseudorandom noise by Wikipedia, the free encyclopedia, pub. Online Jul. 25, 2012 at "https://wikipedia.org/w/index.php?title=Pseudorandom_noise&oldid=504121479", accessed Sep. 3, 2015.
Noise generator by Wikipedia, the free encyclopedia, pub. Online May 6, 2012 at "https://wikipedia.org/w/index.php?title=Noise_generator&oldid=490897729", accessed Sep. 3, 2015.
Office Action for EP Application No. 10779086.7 dated May 12, 2017.
Office Action for EP Application No. 13185148.7 dated Nov. 7, 2017.
EP Office Action dated Oct. 16, 2018 in application No. 10773191.1.
Office Action for EP Application No. 10779086.7 dated Dec. 10, 2018.
Office Action in European Application No. 12784142.7 dated Apr. 10, 2018 in 5 pages.
Office Action for Application No. 13185148.7 dated Jun. 7, 2018.
Office Action in European Application No. 13185148.7 dated Apr. 4, 2019.
Office Action in European Application No. 20191376.1 dated Dec. 18, 2020 in 7 pages.
Office Action in European Application No. 19182152.9 dated Nov. 4, 2019 in 10 pages.
Office Action in European Application No. 20175965.1 dated Oct. 12, 2020 in 7 pages.
GE Healthcare, "Transport ProTM Patient Monitor" Operator's Manual, Software Version 2.1, Apr. 9, 2007, 286 pages.

* cited by examiner

FIG. 1C

ACOUSTIC RESPIRATORY MONITORING SENSOR HAVING MULTIPLE SENSING ELEMENTS

INCORPORATION BY REFERENCE TO ANY RELATED APPLICATIONS

Any and all applications, if any, for which a foreign or domestic priority claim is identified in the Application Data Sheet of the present application are hereby incorporated by reference under 37 CFR 1.57.

Additionally, this application relates to the following U.S. patent applications, the disclosures of which are incorporated in their entirety by reference herein:

| application Ser. No. | Filing Date | Title |
|---|---|---|
| 60/893,853 | Mar. 8, 2007 | MULTI-PARAMETER PHYSIOLOGICAL MONITOR |
| 60/893,850 | Mar. 8, 2007 | BACKWARD COMPATIBLE PHYSIOLOGICAL SENSOR WITH INFORMATION ELEMENT |
| 60/893,858 | Mar. 8, 2007 | MULTI-PARAMETER SENSOR FOR PHYSIOLOGICAL MONITORING |
| 60/893,856 | Mar. 8, 2007 | PHYSIOLOGICAL MONITOR WITH FAST GAIN ADJUST DATA ACQUISITION |
| 12/044,883 | Mar. 8, 2008 | SYSTEMS AND METHODS FOR DETERMINING A PHYSIOLOGICAL CONDITION USING AN ACOUSTIC MONITOR |
| 61/252,083 | Oct. 15, 2009 | DISPLAYING PHYSIOLOGICAL INFORMATION |
| 12/904,836 | Oct. 14, 2010 | BIDIRECTIONAL PHYSIOLOGICAL INFORMATION DISPLAY |
| 12/904,823 | Oct. 14, 2010 | BIDIRECTIONAL PHYSIOLOGICAL INFORMATION DISPLAY |
| 61/141,584 | Dec. 30, 2008 | ACOUSTIC SENSOR ASSEMBLY |
| 61/252,076 | Oct. 15, 2009 | ACOUSTIC SENSOR ASSEMBLY |
| 12/643,939 | Dec. 21, 2009 | ACOUSTIC SENSOR ASSEMBLY |
| 12/904,890 | Oct. 14, 2010 | ACOUSTIC RESPIRATORY MONITORING SENSOR HAVING MULTIPLE SENSING ELEMENTS |
| 12/904,938 | Oct. 14, 2010 | ACOUSTIC RESPIRATORY MONITORING SENSOR HAVING MULTIPLE SENSING ELEMENTS |
| 12/904,907 | Oct. 14, 2010 | ACOUSTIC PATIENT SENSOR |
| 12/904,789 | Oct. 14, 2010 | ACOUSTIC RESPIRATORY MONITORING SYSTEMS AND METHODS |
| 61/252,062 | Oct. 15, 2009 | PULSE OXIMETRY SYSTEM WITH LOW NOISE CABLE HUB |
| 61/265,730 | Dec. 1, 2009 | PULSE OXIMETRY SYSTEM WITH ACOUSTIC SENSOR |
| 12/904,775 | Oct. 14, 2010 | PULSE OXIMETRY SYSTEM WITH LOW NOISE CABLE HUB |
| 12/905,036 | Oct. 14, 2010 | PHYSIOLOGICAL ACOUSTIC MONITORING SYSTEM |
| 61/331,087 | May 4, 2010 | ACOUSTIC RESPIRATION DISPLAY |
| 61/391,098 | Oct. 8, 2010 | ACOUSTIC MONITOR |

Many of the embodiments described herein are compatible with embodiments described in the above related applications. Moreover, some or all of the features described herein can be used or otherwise combined with many of the features described in the applications listed above.

BACKGROUND

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range of between 0.001 Hz to 1 GHz; a low acoustical impedance close to water and human tissue; a high dielectric strength; a good mechanical strength; and piezoelectric membranes are moisture resistant and inert to many chemicals.

Due in large part to the above attributes, piezoelectric membranes are particularly suited for the capture of acoustic waves and the conversion thereof into electric signals and, accordingly, have found application in the detection of body sounds. However, there is still a need for a reliable acoustic sensor, particularly one suited for measuring bodily sounds in noisy environments.

SUMMARY

Embodiments of an acoustic sensor and physiological monitoring system described herein are configured to provide accurate and robust measurement of bodily sounds under a variety of conditions, such as in noisy environments or in situations in which stress, strain, or movement can be imparted onto the sensor with respect to a patient.

While certain embodiments described herein are compatible with single-sensing element designs, according to certain aspects, multiple acoustic sensing elements are employed to provide enhanced physiological monitoring. For example, multiple acoustic sensing elements can be included in one or more sensor packages coupled to a patient and/or at various other locations in the monitoring environment, such as on one or more sensor packages or other components not coupled to the patient.

In some configurations, a plurality of acoustic sensing elements are advantageously arranged in a single acoustic sensor package. In some such embodiments, physical and/or electrical symmetry between the sensing elements can be exploited. In some cases, for example, the electrical poles of two or more sensing elements are connected so as to provide improved electrical shielding, enhanced signal to noise ratio, reduced design complexity and associated cost. In one such configuration, multiple sensing elements are arranged in stack on a sensor frame or other support structure. Generally, shielding can be beneficially achieved using one or more portions that are integral to the sensing elements rather than using physically separate components.

Systems and methods described herein achieve noise compensation in a variety of ways. For example, sensing elements (or groups thereof) can be arranged such that a physiological signal sensing element provides a physiological signal having both a component indicative of a target physiological signal (e.g., respiratory, heart or digestive sounds) and an interfering noise component. At least one other sensing element, on the other hand, provides a reference signal. The reference signal may include a significant noise component, but not a significant target physiological component, for example, and can advantageously be used to produce a physiological signal having a reduced noise component. For example, certain embodiments employ adaptive filtering techniques to attenuate the noise component. In various embodiments, the noise component can come from a variety of sources, an can include, without limitation, ambient noise, interfering bodily sounds emanating from the patient (e.g., respiratory, heart or digestive sounds), noise coming from skin-coupled devices (e.g., surgical or other medical equipment), etc., further specific examples of which are provided herein.

Moreover, according certain aspects, the sensing elements are selectively configurable in a plurality of modes. For example, the sensing elements can be configured as either physiological signal sensing elements or noise sensing elements, as desired. As one illustrative example, a first sensor is used to detect respiratory sounds, while a second sensor used to detect heart sounds. In a first monitoring mode, the system uses the first sensor to detect the target respiratory sounds, and uses the second sensor as a noise reference sensor to minimize the effect of heart sounds (and/or other interfering noise) on the respiratory signal. Conversely, the system can switch to a second mode where the first sensor is used as the reference sensor to reduce the effect of respiratory sounds (and/or other interfering noise) on the signal produced by the second sensor. A wide variety of embodiments incorporating selective sensing element configurations are described herein.

Additionally, sensing elements (or groups thereof) can be arranged with respect to one another such that components of their output signals resulting from a common source (e.g., the patient's body) will be correlated or otherwise generally similar. The signal components from interfering noise sources, on the other hand, can be expected to be uncorrelated or otherwise have certain dissimilarities (e.g., phase or time shift). In these cases, the output signals from the first and second acoustic sensing elements can be combined in ways that accentuate commonalities between the two signals while attenuating differences.

According to yet another aspect of the disclosure, an acoustic sensor includes one or more sensing elements supported by a frame or other support structure. The sensing elements contact the frame at certain locations and are spaced from the frame at others. The sensing elements and frame define a cavity in which the sensing elements vibrate in response to acoustic signals received from a medical patient. However, skin elasticity and the force used to attach the acoustic sensor to the medical patient's skin can affect the volume and/or air pressure within the cavity defined by the sensing elements and frame. Variability in skin elasticity or attachment force can lead to variability in cavity resonance, which can cause unwanted variability in sensor performance. For example, an acoustic sensor that is attached to very elastic skin may provide a different output signal than an acoustic sensor that is attached to firmer or tighter skin. Similarly, an acoustic sensor loosely attached to patient's skin may provide a different output signal than an acoustic sensor tightly attached a patient's skin.

To compensate for skin elasticity and attachment variability, in one embodiment the acoustic sensor support includes one or more pressure equalization pathways. The pathways provide an air-flow channel from the cavity defined by the sensing elements and frame to the ambient air pressure. By equalizing pressure within the cavity with ambient during sensing, variability in sensor performance may be reduced and/or eliminated. In some embodiments, the pressure equalization pathways include one or more holes, notches, ports, or channels that extend from within the sensor's cavity to a location in communication with ambient air pressure.

In certain embodiments, a medical device is provided for non-invasively outputting a reduced noise signal responsive to acoustic vibrations indicative of one or more physiological parameters of a medical patient. In some embodiments, the medical device includes a first acoustic sensing element configured to be acoustically coupled to the body of a patient, the first acoustic sensing element being configured to output a first signal comprising a physiological signal component and a noise component. The medical device can also include a second acoustic sensing element being configured to output a second signal comprising at least a noise component. The medical device of some embodiments includes a noise attenuator configured to produce a reduced noise signal in response to the first and second signals. The reduced noise signal can include a physiological signal component and a noise component. In certain embodiments, the ratio of the physiological signal component of the reduced noise signal to the noise component of the reduced noise signal is greater than the ratio of the physiological signal component of the first signal to the noise component of the first signal.

According to certain aspects, a method of providing a reduced noise signal responsive to acoustic vibrations indicative of one or more physiological parameters of a medical patient is provided. The method can include outputting a first signal using first acoustic sensing element coupled to the body of a patient. The signal may comprise a physiological component and a noise component. The method can further including outputting a second signal using the second acoustic sensing element, the second signal comprising at least a noise component. In certain embodiments, the method further includes processing the first and second signals using a noise attenuator to produce a reduced noise signal in response to the first and second signals. The reduced noise signal can include a physiological signal component and a acoustic noise component. In certain embodiments, the ratio of the physiological signal component of the reduced noise signal to the noise component of the reduced noise signal greater than the ratio of the physiological signal component of the first signal to the noise component of the first signal.

In certain embodiments, a medical device is provided for non-invasively generating a reduced noise signal responsive to acoustic vibrations indicative of one or more physiological parameters of a medical patient. The medical device can include at least one first acoustic sensing element configured to generate a first signal in response to acoustic vibrations. The medical device of certain embodiments also includes at least one second acoustic sensing element configured to generate a second signal in response to acoustic vibrations. In certain embodiments, the medical device further includes a noise attenuation module configured to generate a reduced noise signal indicative of one or more physiological parameters of a medical patient in response to at least one of the first and second signals.

A medical sensor is provided in some embodiments for non-invasively outputting signals responsive to acoustic vibrations indicative of one or more physiological parameters of a medical patient. The medical sensor can include a first acoustic sensing element for generating a first signal.

The medical sensor can also include a second acoustic sensing element for generating a second signal. The first and second signals in some embodiments are configured to be provided to a noise attenuator adapted to reduce a noise component of the first or second signal.

In certain embodiments, an acoustic sensor is provided for non-invasively outputting signals responsive to acoustic vibrations indicative of one or more physiological parameters of a medical patient. In certain embodiments, the acoustic sensor includes a sensor support. The acoustic sensor can also include a first acoustic sensing element at least partially supported by the sensor support and configured to output a first signal responsive to acoustic vibrations. The acoustic sensor of some embodiments includes a second acoustic sensing element at least partially supported by the sensor support and configured to output a second signal responsive to acoustic vibrations. In some embodiments, the first and second acoustic sensing elements are configured to provide the first and second signals to a noise attenuator configured to output a reduced noise signal having a higher signal to noise ratio than either of the first and second signals.

In certain embodiments, a method is provided of non-invasively outputting signals responsive to acoustic vibrations indicative of one or more physiological parameters of a medical patient. The method can include providing a sensor comprising a sensor support, a first acoustic sensing element at least partially supported by the sensor support, and a second acoustic sensing element at least partially supported by the sensor support. The method can further include outputting a first signal using the first acoustic sensing element. In certain embodiments, the first signal is responsive to acoustic vibrations, and the first acoustic sensing element is coupled to a medical patient. The method can include outputting a second signal using the second acoustic sensing element. In certain embodiments, the second signal responsive to acoustic vibrations, and the second acoustic sensing element coupled to the medical patient. In certain embodiments, the method includes providing the first signal and the second signal to a noise attenuator configured to output a reduced noise signal having a higher signal to noise ratio than either of the first and second signals.

In certain embodiments, an acoustic sensor is provided for non-invasively outputting signals responsive to acoustic vibrations indicative of one or more physiological parameters of a medical patient. The acoustic sensor can include a sensor support, and a first piezoelectric film at least partially supported by the sensor support and comprising a first electrode and a second electrode. In certain embodiments, the sensor includes a second piezoelectric film at least partially supported by the sensor support and comprising a first electrode and second electrode. In some embodiments, the first electrode of the first piezoelectric film and the first electrode of the second piezoelectric film are coupled to a common potential, and the second electrode of the first piezoelectric film and the second electrode of the second piezoelectric film are coupled to a noise attenuator.

In certain embodiments, an acoustic sensor is provided for non-invasively outputting signals responsive to acoustic vibrations indicative of one or more physiological parameters of a medical patient. In some embodiments, the acoustic sensor includes a sensor support. In some embodiments, the acoustic sensor includes a first acoustic sensing element at least partially supported by the sensor support and comprising an inner portion and an outer portion. In some embodiments, the acoustic sensor includes a second acoustic sensing element at least partially supported by the sensor support and comprising an inner portion and an outer portion. In certain embodiments, the acoustic sensor is configured such that the inner portions are positioned between the outer portions, the outer portions forming an electrical shielding barrier around the inner portions.

In certain embodiments, a method is provided of manufacturing an acoustic sensor for non-invasively outputting signals responsive to acoustic vibrations indicative of one or more physiological parameters of a medical patient. The method can include providing a first acoustic sensing element comprising an inner portion and an outer portion. The method can also include providing a second acoustic sensing element comprising an inner portion and an outer portion. In certain embodiments, the method includes attaching the first acoustic sensing element to a sensor support. The method in some embodiments includes attaching the second sensing element to the sensor support over the first acoustic sensing element. In certain embodiments, the inner portions of the first and second acoustic sensing elements are disposed between the outer portions of the first and second acoustic sensing elements, and the outer portions form an electrical shielding barrier around the inner portions.

An acoustic sensor is provided in some embodiments that is configured to non-invasively detect acoustic vibrations associated with a medical patient, the acoustic vibrations indicative of one or more physiological parameters of the medical patient. The sensor can include a sensor support and first and second sensing membranes supported by the sensor support, each of said first and second sensing membranes comprising first and second surfaces on opposite sides of each of said first and second sensing membranes. In some embodiments, the first and second sensing membranes are aligned such that said first surfaces face each other. The first surfaces in some embodiments are configured to provide an electrical signal indicative of a physiological parameter of a medical patient, and said second surfaces are configured to provide electrical shielding around said first surfaces.

In some embodiments, an acoustic sensor is provided that is configured to non-invasively detect acoustic vibrations associated with a medical patient. The acoustic vibrations can be indicative of one or more physiological parameters of the medical patient. In certain embodiments, the sensor includes at least one sound-sensing membrane is configured to detect acoustic vibrations associated with a medical patient when the acoustic sensor is attached to the medical patient. The sensor can also include a sensor support defining an acoustic cavity and configured to support the at least one sensing membrane over the acoustic cavity. The sensor support may include at least one pressure equalization pathway formed in a wall of the sensor support, the at least one pressure equalization pathway extending from the acoustic cavity to ambient air pressure.

In certain embodiments, an acoustic sensor is configured to non-invasively detect acoustic vibrations associated with a medical patient, the acoustic vibrations indicative of one or more physiological parameters of the medical patient. The sensor can include at least one sound-sensing membrane configured to detect acoustic vibrations associated with a medical patient when the acoustic sensor is attached to the medical patient. The sensor can further include a sensor support configured to support the at least one sensing membrane against the medical patient's skin. In some embodiments, the sensor is configured to provide an electrical signal in response to acoustic vibrations detected by the at least one sound-sensing membrane substantially independent of a force used to attach the sensor to the medical patient's skin.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIG. 1C is a top perspective view illustrating portions of a sensor system in accordance with an embodiment of the disclosure.

DETAILED DESCRIPTION

Various embodiments will be described hereinafter with reference to the accompanying drawings. These embodiments are illustrated and described by example only, and are not intended to be limiting.

Overview

In various embodiments, an acoustic sensor configured to operate with a physiological monitoring system includes an acoustic signal processing system that measures and/or determines any of a variety of physiological parameters of a medical patient. For example, in an embodiment, the physiological monitoring system includes an acoustic monitor. The acoustic monitor may be an acoustic respiratory monitor which can determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases the acoustic signal processing system monitors other physiological sounds, such as heart rate to help with probe off detection, heart sounds (S1, S2, S3, S4, and murmurs), and change in heart sounds such as normal to murmur or split heart sounds indicating fluid overload. Moreover, the acoustic signal processing system may (1) use a second probe over the chest for additional heart sound detection; (2) keep the user inputs to a minimum (example, height); and/or (3) use a Health Level 7 (HL7) interface to automatically input patient demography.

In certain embodiments, the physiological monitoring system includes an electrocardiogramar EKG) that measures and/or determines electrical signals generated by the cardiac system of a patient. The ECG includes one or more sensors for measuring the electrical signals. In some embodiments, the electrical signals are obtained using the same sensors used to obtain acoustic signals.

In still other embodiments, the physiological monitoring system includes one or more additional sensors used to determine other desired physiological parameters. For example, in some embodiments, a photoplethysmograph sensor determines the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In other embodiments, a capnograph determines the carbon dioxide content in inspired and expired air from a patient. In other embodiments, other sensors determine blood pressure, pressure sensors, flow rate, air flow, and fluid flow (first derivative of pressure). Other sensors may include a pneumotachometer for measuring air flow and a respiratory effort belt. In certain embodiments, these sensors are combined in a single processing system which processes signal output from the sensors on a single multi-function circuit board.

Figures 1A, 1B:
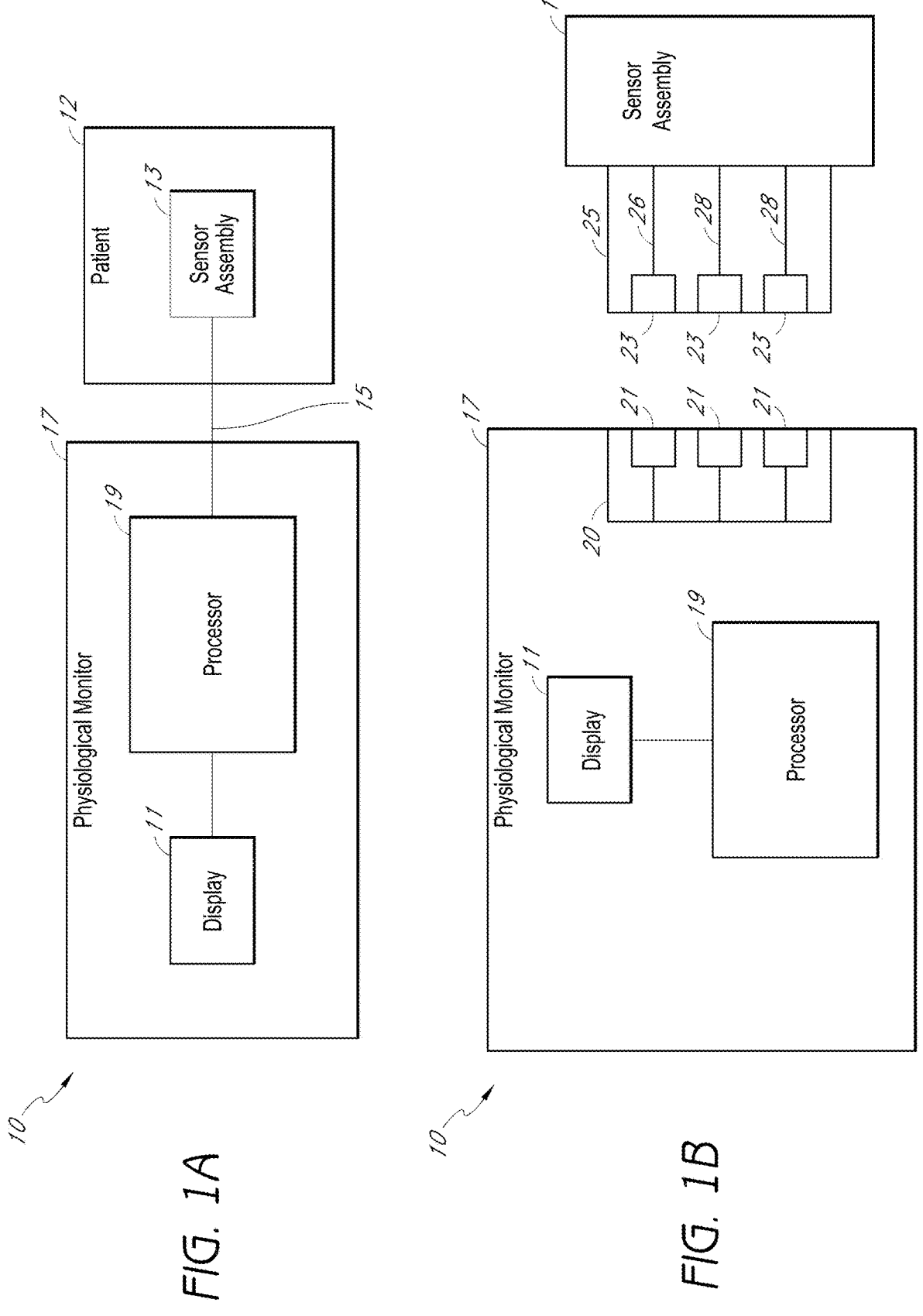
FIGS. 1A-B are block diagrams illustrating physiological monitoring systems in accordance with embodiments of the disclosure.

Referring to the drawings, FIGS. 1A through IC illustrate example patient monitoring systems, sensors, and cables that can be used to provide acoustic physiological monitoring of a patient, such as respiratory monitoring. FIGS. 2A-18 illustrate embodiments of sensors and systems, such as those incorporating multiple acoustic sensing elements to provide certain beneficial results, including enhanced signal-to-noise ratio (SNR), electrical shielding and noise compensation, for example. Embodiments of FIGS. 2A-18 can be implemented at least in part using the systems and sensors described in FIGS. 1A through IC. FIGS. 19A-23E show additional acoustic sensors and associated components compatible with embodiments described herein.

Turning to FIG. 1A, an embodiment of a physiological monitoring system 10 is shown. In the physiological monitoring system 10, a medical patient 12 is monitored using one or more sensor 13, each of which transmits a signal over a cable 15 or other communication link or medium to a physiological monitor 17. The physiological monitor 17 includes a processor 19 and, optionally, a display 11. The one or more sensors 13 include sensing elements such as, for example, acoustic piezoelectric devices, electrical ECG leads, pulse oximetry sensors, or the like. The sensors 13 can generate respective signals by measuring a physiological parameter of the patient 12. The signals are then processed by one or more processors 19. The one or more processors 19 then communicate the processed signal to the display 11. In an embodiment, the display 11 is incorporated in the physiological monitor 17. In another embodiment, the display 11 is separate from the physiological monitor 17. In one embodiment, the monitoring system 10 is a portable monitoring system. In another embodiment, the monitoring system 10 is a pod, without a display, that is adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include at least two acoustic sensors. In still another embodiment, the one or more sensors 13 include at least two acoustic sensors and one or more ECG sensors, pulse oximetry sensors, bioimpedance sensors, capnography sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13.

As shown in FIG. 1B, the acoustic sensor 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors 103, one or more additional cables 115 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly.

Figure 1C:
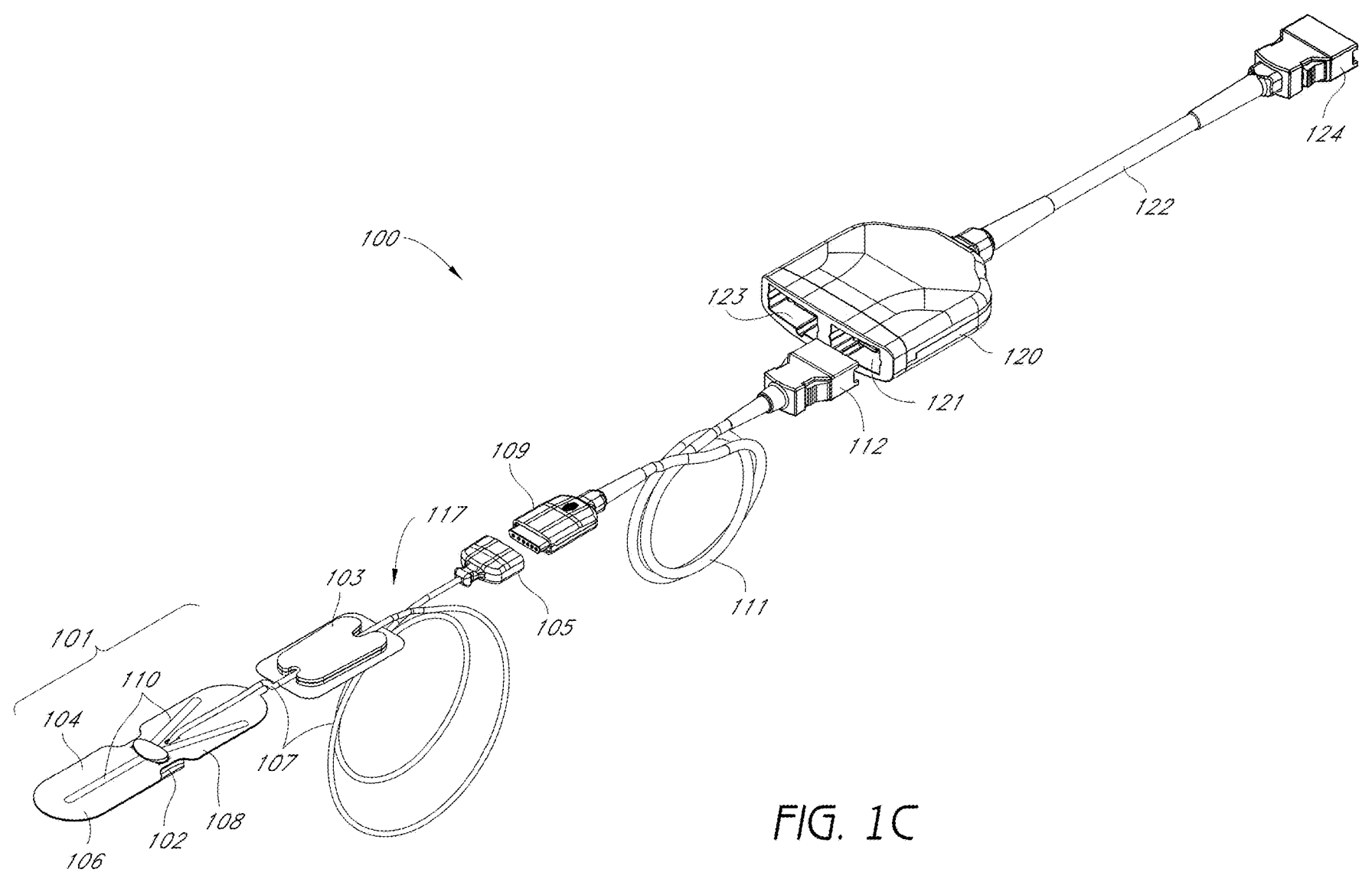

FIG. 1C illustrates an embodiment of a sensor system 100 including a sensor 101 suitable for use with any of the physiological monitors shown in FIGS. 1A and 1B. The sensor system 100 includes a sensor 101, a sensor cable 117, a patient anchor 103 attached to the sensor cable 117, and a connector 105 attached to the sensor cable 117. The sensor 101 includes a shell 102 configured to house certain componentry of the sensor 101, and an attachment subassembly 104 positioned the sensor 101 and configured to attach the sensor 101 to the patient.

The sensor 101 can be removably attached to an instrument cable 111 via an instrument cable connector 109. The instrument cable 111 can be attached to a cable hub 120, which includes a port 121 for receiving a connector 112 of the instrument cable 111 and a second port 123 for receiving another cable. In certain embodiments, the second port 123 can receive a cable connected to a pulse oximetry or other sensor. In addition, the cable hub 120 could include additional ports in other embodiments for receiving additional cables. The hub includes a cable 122 which terminates in a connector 124 adapted to connect to a physiological monitor (not shown). In another embodiment, no hub is provided and the acoustic sensor 101 is connected directly to the monitor, via an instrument cable 111 or directly by the sensor cable 117, for example.

The component or group of components between the sensor 101 and the monitor in any particular embodiment may be referred to generally as a cabling apparatus. For example, where one or more of the following components are included, such components or combinations thereof may be referred to as a coupling apparatus: the sensor cable 117, the connector 105, the cable connector 109, the instrument cable 111, the hub 120, the cable 122, and/or the connector 124. It should be noted that one or more of these components may not be included, and that one or more other components may be included between the sensor 101 and the monitor, forming the cabling apparatus.

The acoustic sensor 101 can further include circuitry for detecting and transmitting information related to biological sounds to the physiological monitor. These biological sounds can include heart, breathing, and/or digestive system sounds, in addition to many other physiological phenomena. The acoustic sensor 101 in certain embodiments is a biological sound sensor, such as the sensors described herein. In some embodiments, the biological sound sensor is one of the sensors such as those described in U.S. patent application Ser. No. 12/044,883, filed Mar. 7, 2008, which is incorporated in its entirety by reference herein (the '883 application). In other embodiments, the acoustic sensor 101 is a biological sound sensor such as those described in U.S. Pat. No. 6,661,161 or U.S. patent application Ser. No. 12/643, 939, filed on Dec. 21, 2009 (the '939 application), both of which are incorporated by reference herein in their entirety. Other embodiments include other suitable acoustic sensors. For example, in certain embodiments, compatible acoustic sensors can be configured to provide a variety of auscultation functions, including live and/or recorded audio output (e.g., continuous audio output) for listening to patient bodily or speech sounds. Examples of such sensors and sensors capable of providing other compatible functionality can be found in U.S. patent application Ser. No. 12/905,036 embodiment, the sensing elements 920, 921 can be configured to sense and process ultrasonic signals (e.g., for ultra-sonic imaging). Examples of sensors capable of various types, entitled PHYSIOLOGICAL ACOUSTIC MONITORING SYSTEM, filed on Oct. 14, 2010, which is incorporated by reference herein in its entirety.

In an embodiment, the acoustic sensor 101 includes one or more sensing elements (not shown), such as, for example, a piezoelectric device or other acoustic sensing device. Where a piezoelectric membrane is used, a thin layer of conductive metal can be deposited on each side of the film as electrode coatings, forming electrical poles. The opposing surfaces or poles may be referred to as an anode and cathode, respectively. Each sensing element can generate a voltage potential across the electrical poles that is responsive to vibrations generated by the patient.

The shell 102 according to certain embodiments houses a frame (not shown) or other support structure configured to support various components of the sensor 101. The one or more sensing elements can be generally wrapped in tension around the frame. For example, the sensing elements can be positioned across an acoustic cavity disposed on the bottom surface of the frame. Thus, the sensing elements according to some embodiments are free to respond to acoustic waves incident upon them, resulting in corresponding induced voltages across the poles of the sensing elements.

Additionally, the shell 102 can include an acoustic coupler not shown), which advantageously improves the coupling between the source of the signal to be measured by the sensor (e.g., the patient's body) and the sensing element. The acoustic coupler of one embodiment includes a bump positioned to apply pressure to the sensing element so as to bias the sensing element in tension. For example, the bump can be positioned against the portion of the sensing element that is stretched across the cavity of the frame.

The attachment sub-assembly 104 in some embodiments includes first and second elongate portions 106, 108. The first and second elongate portions 106, 108 can include patient adhesive (e.g., in some embodiments, tape, glue, a suction device, etc.). The adhesive on the elongate portions 106, 108 can be used to secure the sensor subassembly 102 to a patient's skin. One or more resilient backbone members 110 included in the first and/or second elongate portions 106, 108 can beneficially bias the sensor subassembly 102 in tension against the patient's skin and/or reduce stress on the connection between the patient adhesive and the skin.

While an example sensor system 100 has been provided, embodiments described herein are compatible with a variety of sensors and associated components. For example, compatible acoustic couplers, support frames, attachment subassemblies, sensing elements, and other components are described with respect to FIGS. 19-23 below and in the '939 application.

Improving Signal-to-Noise Ratio Using Multiple Sensors

Figure 2A:
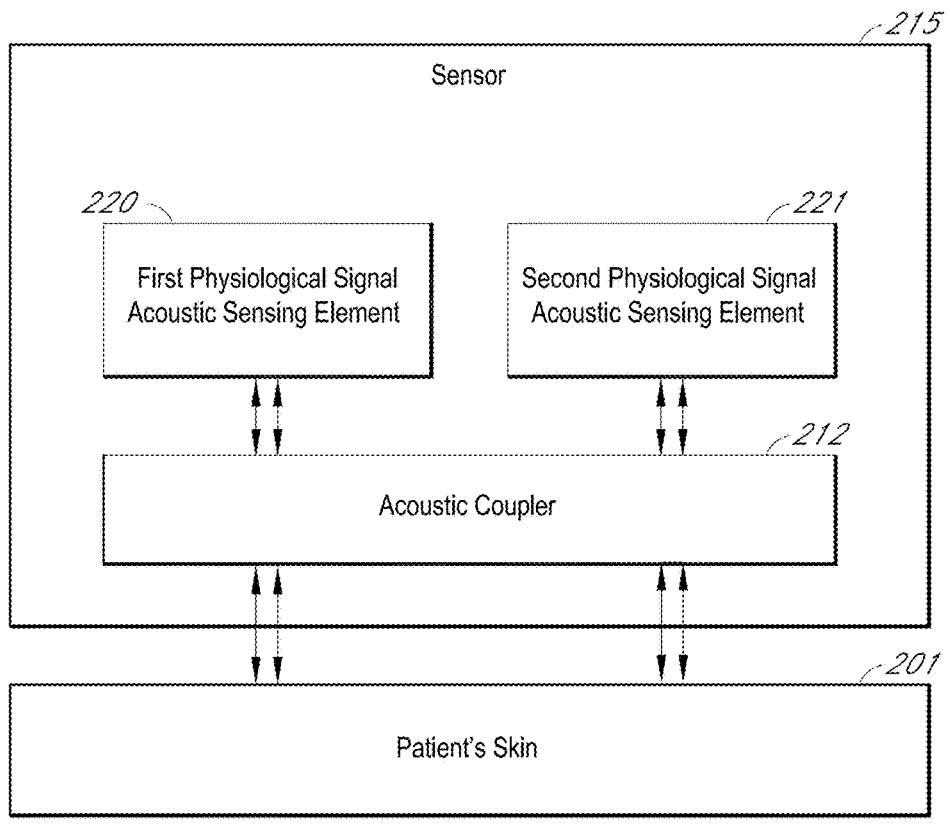
FIGS. 2A-2B are block diagrams of example embodiments of patient sensors that including first and second physiological signal acoustic sensing elements and at least one acoustic coupler for acoustically coupling both of the first and second physiological signal acoustic sensing elements to a patient's body.

FIG. 2A is a block diagram of an embodiment of a patient sensor 215 that includes first and second physiological signal acoustic sensing elements 220, 221. The sensing elements 220, 221 are generally adapted to detect physiological sounds from a patient 201, and can be any of the sensing elements described herein, such as piezoelectric membranes.

The patient sensor 215 can also include at least one acoustic coupler for acoustically coupling the first and second physiological signal acoustic sensing elements 220, 221 to a patient's body 201. In FIG. 2, both acoustic sensing elements 220, 221 are acoustically coupled to the patient. As shown in FIG. 1C, the acoustic coupling can be achieved using a single acoustic coupler 212 for both sensing elements.

According to one configuration, the acoustic sensing elements 220, 221 are supported in a stacked configuration on a sensor frame (not shown) or other support. Example stacked configurations are described below with respect to FIGS. 3B, 4A-4B and 6A-6B.

Figure 2B:
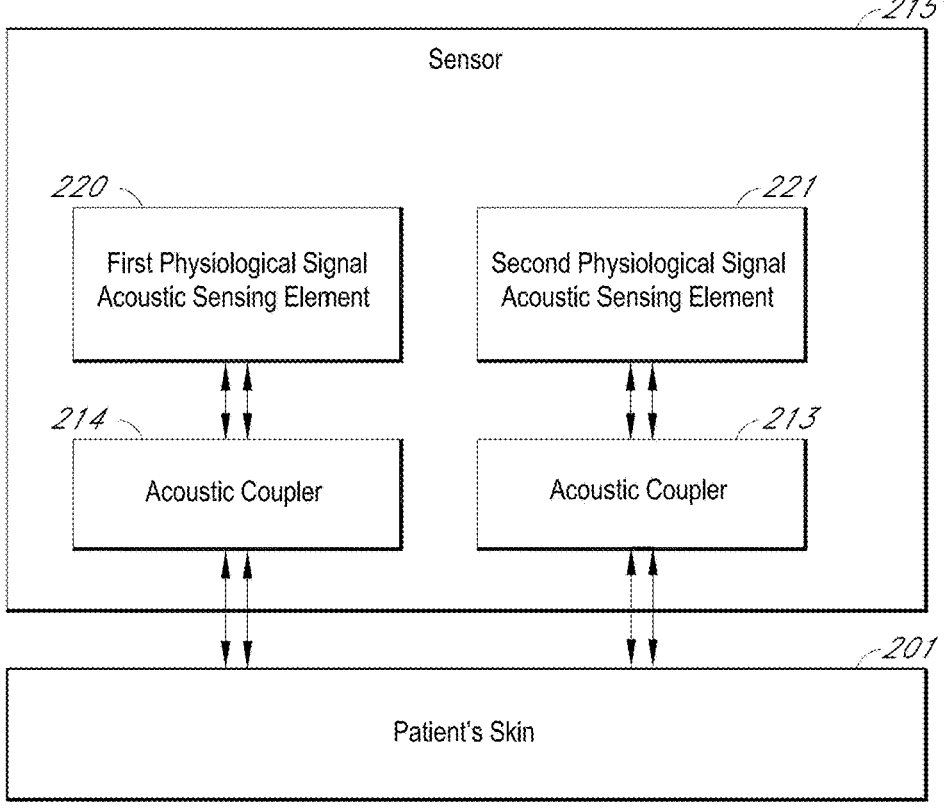
Figure 14:
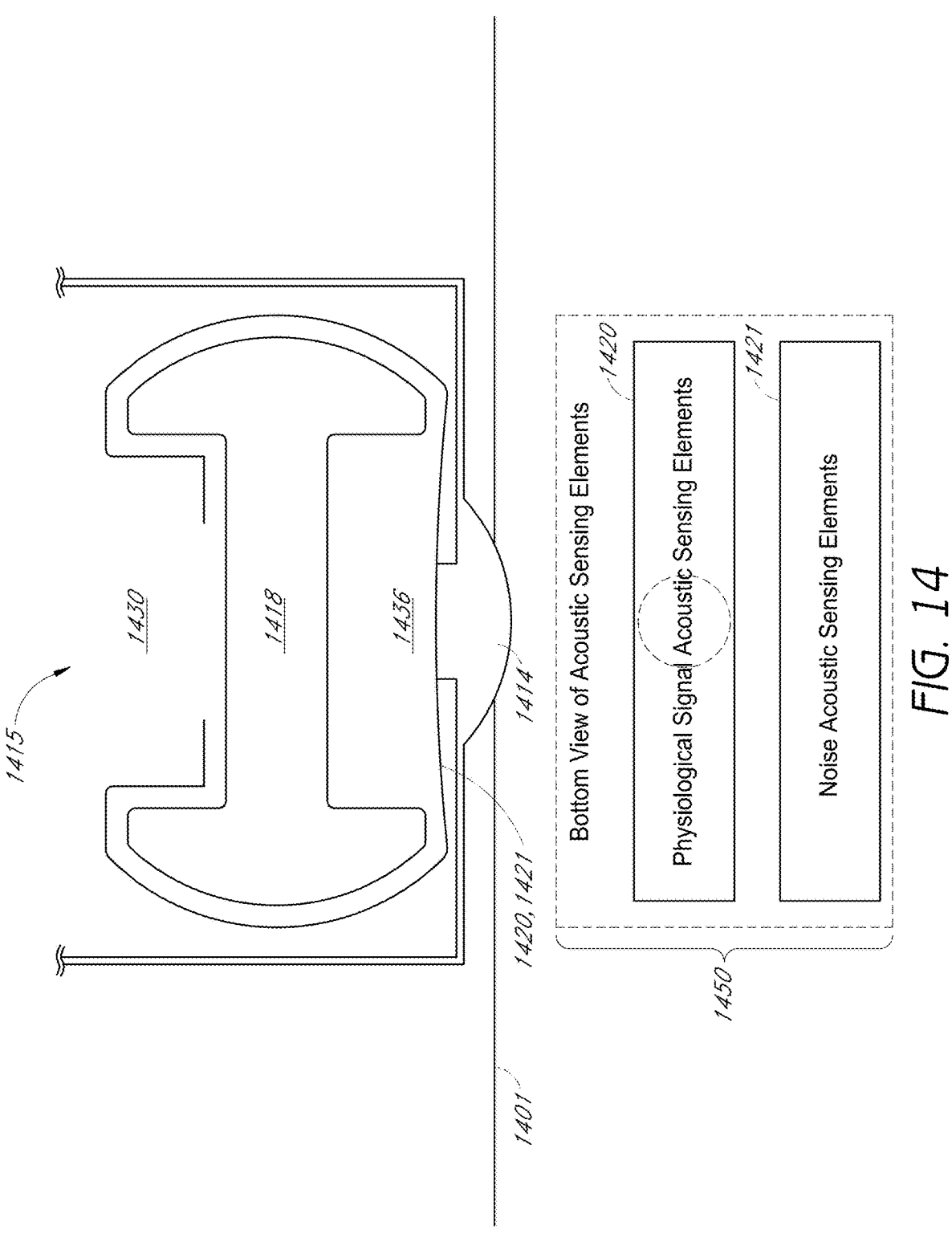
FIG. 14 is a cross-sectional schematic drawing of another embodiment of an acoustic sensor that includes a physiological signal acoustic sensing element and a noise acoustic sensing element.

As shown in FIG. 2B, first and second acoustic couplers 213, 214 can be used in alternative embodiments. The acoustic couplers 213, 214 can be similar, for example, to the others described herein. In some embodiments, the acoustic sensing elements 220, 221 are supported in a side-by-side configuration on a frame, similar to what is illustrated in FIG. 14 below (except that both sensing elements 220, 221 are acoustically coupled to the body of the patient, whereas only one of the sensing elements 1420, 1421 is coupled to the body in FIG. 14). In other embodiments, no acoustic coupler is included.

In some embodiments, the acoustic coupler, or couplers, 213, 214 are designed to provide a substantially equal amount of coupling between each of the sensing elements 220, 221 and the patient's body 201, though this is not required. Example acoustic couplers compatible with the sensor 215 are described in greater detail throughout the disclosure.

As described, the first and second physiological signal acoustic sensing elements 220, 221 can be specially adapted to detect physiological sounds from a patient. However, the signals output by the acoustic sensing elements 220, 221 may also include noise (e.g., random noise, white Gaussian noise, etc.) from a variety of sources, which decreases the signal-to-noise ratio (SNR) of the signals.

The SNR of these signals can be improved, however, by collecting the desired physiological signal from more than one acoustic sensing element, and then combining (e.g., summing, subtracting, averaging, etc.) the respective outputs from the acoustic sensing elements in a manner that tends to reinforce the physiological signal components of the signals while tending to cancel or reduce the noise components of the signals. For example, the sensor 215, monitor, or other intermediate component, can include a noise attenuator which performs the combining of the signals from the sensing elements 220, 221 to achieve the improved SNR signal. Some embodiments of this approach are illustrated in FIGS. 3A-3B, 4A-4B and 6A-6B.

Generally, where sensors, sensing elements, couplers, etc., are described throughout the disclosure as being coupled to the patient's body, this may mean that one or more of the acoustic couplers are directly coupled to the patient's skin or other body part, such as where an acoustic coupler 212 is directly coupled to the skin 201 and transmits acoustic signals to one or more sensing elements 220, 221 as shown in FIG. 2A. However, this is not necessarily the case. For example, in some embodiments, the entire sensor, including couplers, where used, and/or sensing elements may be spaced from the patient's body and still receive acoustic signals emanating from the patient.

Figures 3A, 3B:
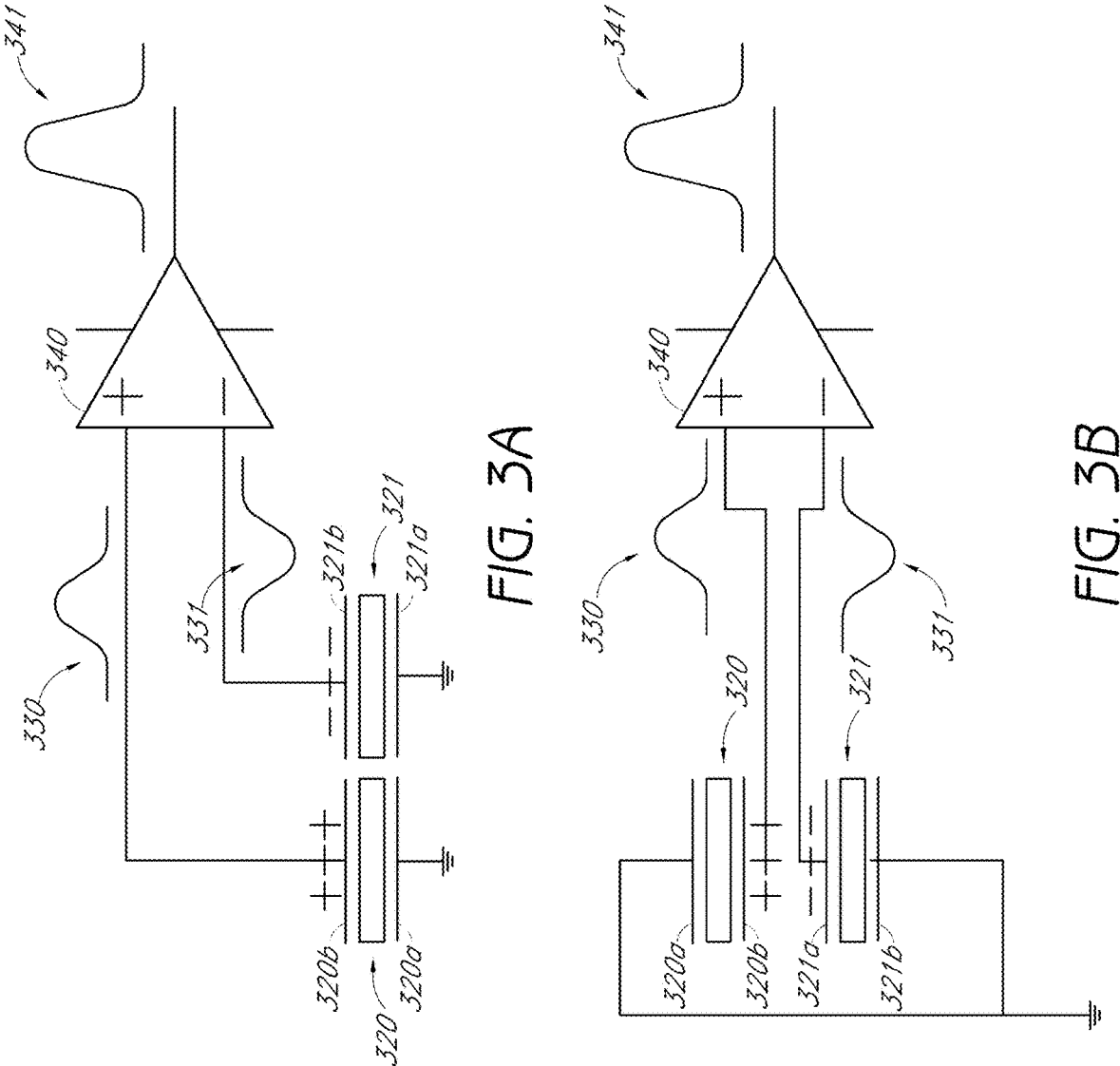
FIG. 3A is a schematic illustration of an embodiment of a circuit for improving signal-to-noise ratio by combining physiological signals from two or more acoustic sensing elements.
FIG. 3B is a schematic illustration of an embodiment of a circuit for improving signal-to-noise ratio by combining physiological signals from two or more acoustic sensing elements arranged in a stacked configuration.

FIG. 3A is a schematic illustration of an embodiment of a circuit for improving signal-to-noise ratio by combining physiological signals from two or more acoustic sensing elements 320, 321. The two acoustic sensing elements 320, 321 may be acoustically coupled to the patient's body. In some embodiments, each of the first and second physiological signal acoustic sensing elements 320, 321 is a piezoelectric film, each having an anode and a cathode. The acoustic sensing elements 320, 321 detect physiological sounds from the patient's body and generate electrical waveforms corresponding to the physiological sounds.

Example compatible piezoelectric films are described herein, with respect to FIGS. 4A-4B, 5A-5D, 6A-6B and 20A-20C, for example.

In FIG. 3A, the piezoelectric films 320, 321 are configured so as to generate output signals where the physiological signal components are 180° or approximately 180° out of phase. For example, in FIG. 3, the acoustic sensing elements 320, 321 generate voltage waveforms 330, 331 in response to physiological sounds from the patient. In the figure, the voltage waveform 330 is a positive pulse, while the voltage waveform 331 is a negative pulse, 180° out of phase from the positive pulse 330. Each of the physiological signal acoustic sensing elements 320, 321 is communicatively coupled to a sensing circuit 340. For example, the sensing circuit 340 may comprise or be referred to as a noise attenuator. Other example noise attenuators are described below with respect to FIGS. 7, 8, 9, and/or 17, for example. In the illustrated embodiment, the sensing circuit 340 is a difference amplifier, though other sensing circuits 340 can be used.

In some embodiments, the 180° phase shift between the outputs from the two piezoelectric films 320, 321 is achieved by differentially connecting the piezoelectric films to the difference amplifier 340. For example, the cathode 320b of the first piezoelectric film 320 can be connected to the non-inverting terminal of the difference amplifier, while the anode 321a of the second piezoelectric film 321 can be connected to the inverting terminal of the difference amplifier 340. The anode 320a and the cathode 321b of the first and second films 320, 321, respectively, can be connected to ground (or be otherwise operatively coupled or coupled to a common potential). In some embodiments, the 180° phase shift is facilitated by mounting the two piezoelectric films 320, 321 such that one is flipped with respect to the other. For example, the two piezoelectric films 320, 321 can be mounted such that the cathode of one of the films faces toward the patient's body, while the anode of the other film faces toward the patient's body.

Since, in some embodiments, the physiological signal component of the second voltage waveform 331 is substantially a negative copy of the physiological signal component of the first voltage waveform 330, when these two waveforms 330, 331 are subtracted by the sensing circuit 340, they combine constructively, as indicated by the output waveform 341 from the sensing circuit 340. However, the outputs from the first and second piezoelectric films 320, 321 may also each include a noise component (not illustrated in the waveforms 330, 331). If the noise in the outputs from the piezoelectric films is random or otherwise uncorrelated, then at least a portion of the noise will tend to be combined destructively by the sensing circuit 340. Thus, the sensing circuit 340 can amplify the physiological signal component from the first and second piezoelectric films 320, 321 while attenuating random noise. The result in certain embodiments is that the physiological signal is emphasized while the random noise component of the output signals from the piezoelectric films 320, 321 is deemphasized.

For example, in one embodiment, the physiological signal is at least approximately doubled while the noise component is increased but less than doubled. The noise component might not double due to the random or uncorrelated nature of the noise, resulting in some portions of the noise combining additively while others combine negatively. Because the increase in the physiological signal can be greater than the increase in the noise, the sensor assembly configuration shown in FIG. 3A can improve signal to noise ratio (SNR).

While the configuration of FIG. 3A shows sensing elements 320, 321 in a side-by-side configuration, other configurations are possible. For example, FIG. 3B illustrates an embodiment of a circuit for improving signal-to-noise ratio where the sensing elements 320, 321 are in a stacked configuration with respect to one another. As described in further detail below with respect to FIGS. 4A-5B, the first sensing element 320 may be wrapped around a frame, and the second sensing element 321 may be wrapped around the first sensing element 320 and the frame.

Similar to the sensor configuration of FIG. 3A, the cathode 320b of the first piezoelectric film 320 can be connected to the non-inverting terminal of the sensing circuit 340, while the anode 321a of the second piezoelectric film 321 can be connected to the inverting terminal of the sensing circuit 340. Thus, in the illustrated embodiment the inner electrodes 320b, 321a of the first and second sensing elements 320, 321 generally face one another in the stacked configuration. The inner electrodes 320b, 321a are shown connected to the terminals of the sensing circuit 340, while the outer electrodes 320a, 321b are connected to ground.

Depending on the embodiment, the configuration shown in FIG. 3B can provide similar improved SNR advantages as described above with respect to FIG. 3A. In addition, as described herein (e.g., with respect to FIGS. 4A-6B), such a configuration can also provide enhanced electrical shielding. For example, the outer electrodes 320a, 321b of the sensing elements 320, 321, respectively, can be used to shield the inner electrodes 320b, 321a from electrical noise. As used herein, the terms "shield," "shielding," and the like, in addition to having their ordinary meaning, can mean reducing or attenuating noise, rather than completely eliminating noise. However, in some embodiments, the terms "shield," "shielding," and the like can also mean completely eliminating noise.

Generally, a variety of different sensing circuits 340 can be used in the embodiments of FIGS. 3A-3B and in generally any of the embodiments described herein where appropriate. Moreover, depending on the sensing circuit 340 used, the electrodes can be connected in a number of arrangements to achieve a similar SNR improvement. For example, a similar result could be obtained by connecting either both anodes or both cathodes, of the piezoelectric films 320, 321 to the inputs of a summing amplifier instead of a sensing circuit. In such embodiments, the physiological signal components of the outputs from the piezoelectric films can be approximately in phase and, therefore, can combine constructively when added by the summing amplifier. Still, at least a portion of random noise from the two output signals from the piezoelectric films 320, 321 will combine destructively, thereby attenuating noise and improving SNR. In some embodiments, more than two physiological signal acoustic sensing elements are used, and their inputs are summed together by, for example, a summing amplifier, a digital signal processor, etc. In some embodiments, one or more of the outer electrodes 320a, 321b can be operatively coupled to the sensing circuit 340, and one or more of the inner electrodes 320b, 321a are connected to ground. In yet other embodiments, the sensing circuit 340 comprises a coupling junction coupling together one or more of the electrodes of the respective sensing elements 320, 321.

Moreover, the number and arrangement of the sensing elements 320, 321 can vary according to certain aspects. For example, in some embodiments, more than two physiological signal acoustic sensing elements 320, 321 are used, and their inputs are summed together by, for example, a summing amplifier, a digital signal processor, etc. A variety of configurations including more than two sensing elements are possible. For example, in one embodiment a pair of stacked sensing elements is arranged in a side-by-side configuration on a frame with respect to another pair of stacked sensing elements. In other embodiments, more than two sensing elements (e.g., 3, 4, 5 or more) are arranged in a stacked configuration. In yet other embodiments, more than two sensing elements (e.g., 3, 4, 5 or more) are arranged side-by-side with respect to one another.

Figure 4A:
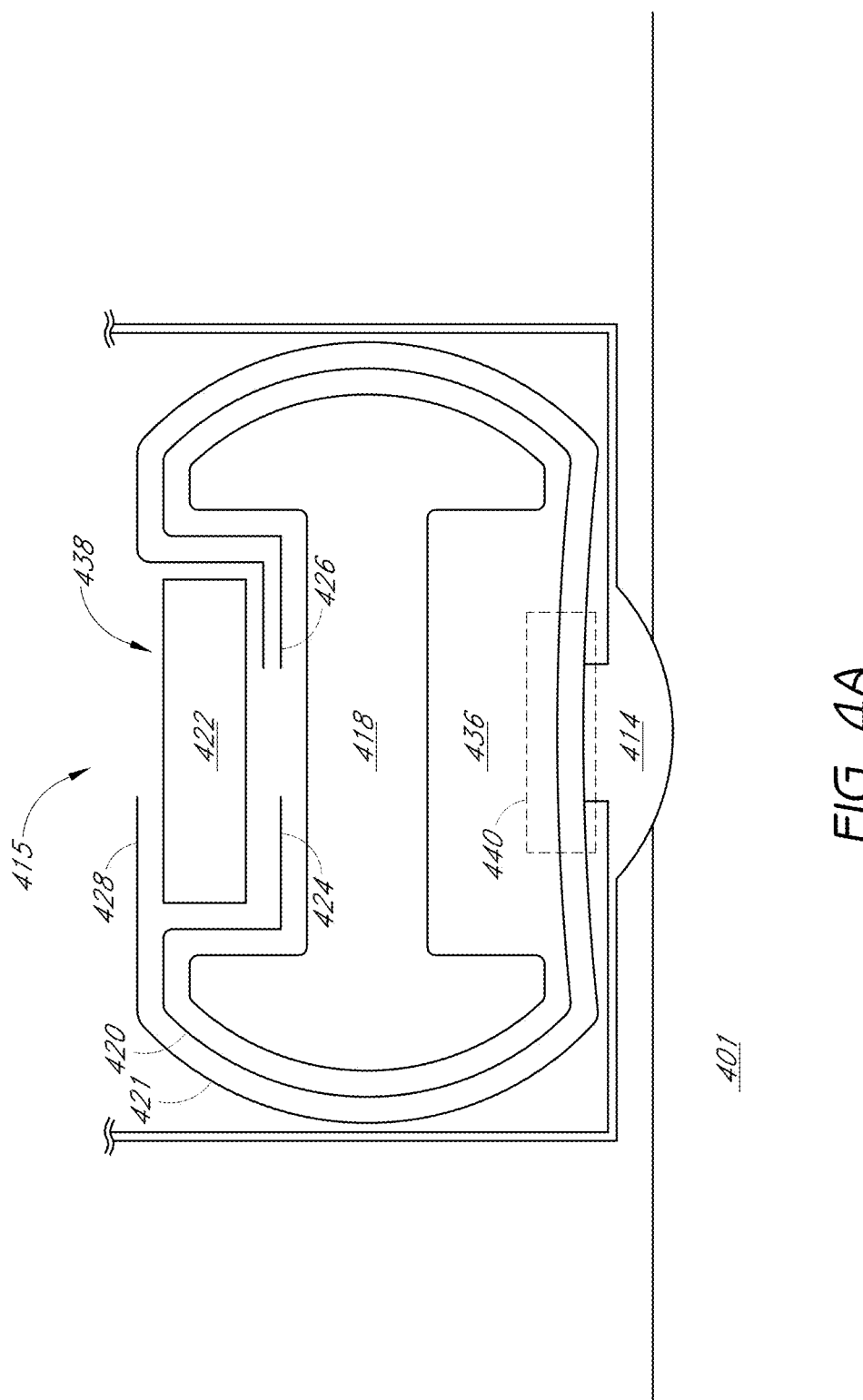
FIG. 4A is a cross-sectional schematic drawing of an embodiment of an acoustic sensor that includes first and second acoustic sensing elements in a stacked configuration.

FIG. 4A is a cross-sectional schematic drawing of an embodiment of an acoustic sensor 415 that includes first and second acoustic sensing elements 420, 421 in a stacked configuration. When connected to a sensing circuit (not shown, e.g., a difference amplifier) in the manner described above with respect to FIG. 3B, the acoustic sensor 415 can advantageously provide improved signal-to-noise ratio.

In the depicted embodiment, the first acoustic sensing element 420 is wrapped around a portion of the frame 418 and the second acoustic sensing element 421 is generally wrapped around the first acoustic sensing element 420 and also supported by the frame. In the illustrated embodiment, the physiological signal acoustic sensing elements 420, 421 are piezoelectric films. An acoustic coupler 414 acoustically couples the sensing elements 420, 421 to the patient's body 401, and can be aligned with both the first and second sensing elements 420, 421, as shown. In some other embodiments, an acoustic coupler 414 is not used. In the embodiment of FIG. 4A, the two piezoelectric films 420, 421 both extend over the acoustic cavity 436 of the frame 2118. Thus, the films 420, 421 are free to respond to acoustic waves incident upon them, resulting in induced voltages.

In the depicted embodiment, a PCB 422 is disposed in the upper cavity 438 of the frame 418, and is in electrical contact with one or more of the electrodes of the first and second sensing elements 420, 421. For example, the PCB 422 can be in electrical contact with the anode and cathode of each of the sensing elements 420, 421. While other configurations are possible, first and second ends 424, 426 of the first sensing element 420 can generally extend underneath opposite sides of the PCB 422. A first end 428 of the second sensing element 421 extends underneath the PCB 422, while a second end 430 of the second sensing element 421 extends over the opposing side of the PCB 422.

The upper side of the first ends 424, 428 of the first and second sensing elements 420, 422 can include contacts (not shown) corresponding to both electrodes of the respective sensing elements 420, 421. These contacts can be coupled to corresponding contacts on the underside of the PCB 422. One or more through holes or vias may be used to extend the electrodes on the underside of the ends 424, 428 of the sensing elements 420, 421 up to the upper side, enabling contact with appropriate PCB 422 contacts. Example first and second sensing elements compatible with the arrangement of FIG. 4 are described with respect to FIGS. 5A-6B. Additionally, another example piezoelectric membranes including through holes or vias are described below with respect to FIGS. 20A-20C.

While not shown for the purpose of clarity, in one embodiment, at least one additional layer (not shown) can be disposed between the sensing elements 420, 421. The additional layer can include an adhesive that adhesively couples the sensing elements 420, 421 together. This adhesive coupling can help ensure that the sensing elements 420, 421 move uniformly together in response to vibrations, reducing losses and improving the response of the sensor. The adhesive coupling can also at least partially maintain tension of one or more of the sensing elements 420, 421.

The additional layer can further be configured to insulate the sensing elements 420, 421 from one another, preventing shorts, noise and/or other undesirable electrical behavior. For example, the additional layer can include a dielectric material. In an embodiment, the adhesive described above acts as a dielectric material. Additional adhesive layers are described below with respect to FIGS. 6A-6B, 19D-19E and 6D-6E, for example.

The ends of the sensing elements 420, 422 may be configured to provide improved sensor performance, reliability, etc. For example, the additional layer may extend to the ends of one or more of the sensing element 420, 422. In one embodiment, the additional layer is an adhesive layer extending to the under side of the second end 430 of the second sensing element 420, helping secure the connection between the second sensing element 422 and the PCB 422. Moreover, in such embodiments, the second end 430 may be generally stretched across the top of the PCB 422, biasing one or more of the sensing elements 420, 421 in tension and thus providing an improved piezoelectric response.

Depending on the embodiment, one or more of the ends of the sensing elements 420, 421 can also include a dielectric material. For example, in one embodiment, the underside of the second end 430 of the second sensing element 421 includes a dielectric material, thereby insulating the second end 430 and the PCB 422. Additionally, the electrode coatings can be configured to reduce the possibility of electrical shorts or other undesirable behavior. In one embodiment, for example, the electrode coating on the underside of the second sensing element 421 does not extend to the second end 430, thereby reducing the risk of undesirable electrical contact between the second end 430 and the top surface of the PCB 422. In another embodiment, a dielectric material is placed on the underside of the PCB 422 instead of or in addition to providing a dielectric material on the end of the sensing element 420 or 421.

A variety of other configurations are possible for the arrangement of the sensing elements 420, 421. For example, in one embodiment, the ends of the sensing elements 420, 421 which are not connected to the PCB 422 do not extend over or under the PCB 422. In another embodiment, each end of the sensing elements 420, 421 includes one electrode contact, and all four ends are thus in electrical contact with corresponding contacts on the PCB 422. This is in contrast with the arrangement described above, in which the upper side of the first ends 424, 428 each include both anode and cathode electrode contacts for the respective sensing elements 420, 421.

As discussed, and as with many of the embodiments described herein, the piezoelectric films 420, 421 are shown in FIG. 4A spaced apart for clarity and ease of illustration. However, in addition to the additional layers described above, the two piezoelectric films 420, 421 can be separated by one or more mechanical supports, acoustic decouplers, shielding layers, or other layers or components. Additionally, any of these layers may be disposed between the frame 418 and the first piezoelectric film 420 and/or wrapped around the outside of the second sensing element 421.

Shielding Using Multiple Sensing Elements

In certain embodiments, multiple sensing elements can be employed to form an electrical noise shielding barrier, providing electrical shielding. Moreover, using the sensing elements or portions thereof to form the barrier can simplify the design of the sensor, reducing costs. For example, one or more stacked sensing elements can be configured to electrically shield the sensor. In some configurations, where the stacked sensing elements are piezoelectric films, the inner, facing electrodes of the films in the stack are used to communicate voltage signals generated by the piezoelectric elements to the sensing circuitry of the sensor (and/or monitor). The outer electrodes of the films in the stack can advantageously be configured to shield the inner electrodes from electrical noise. Generally, throughout the disclosure, the term "inner" refers to the sensing element surface and/or electrode coating which is facing the other sensing element in the active region of the stack (e.g., across the acoustic cavity). Conversely, the term "outer" refers to the sensing element surface and/or electrode which is facing away from the other sensing element in the active region of the stack.

The electrical noise shielding barrier can electrically shield the electrical poles of the sensing element from external electrical noises. In some embodiments the outer portions of the sensing element form a Faraday cage or shield around the inner portions. Thus, the outer portions can distribute external electrical noise substantially equally to the electrical poles of the piezoelectric sensing element. The shield can act to reduce the effect of noise on the sensing element from sources such as external static electrical fields, electromagnetic fields, and the like.

Using a second sensing element to form an electrical shielding barrier can also help to reduce costs by reducing the complexity involved in constructing the sensor and reducing material costs. For example, such embodiments may not include one or more shielding layers which are physically separate from the sensing elements (e.g., copper shielding layers), reducing manufacturing costs associated with purchasing and handling such components. However, certain aspects of shielding barriers formed from multiple sensing elements described herein are compatible with shielding barriers formed from separate layers and aspects thereof. Example shielding barriers including those formed from separate shielding layers are described with respect to FIGS. 2D-2E below and throughout the '939 application, including, without limitation, paragraphs [0120]-[0146] and FIGS. 2D-2E of the '939 application which are incorporated by reference herein.

Figure 4B:
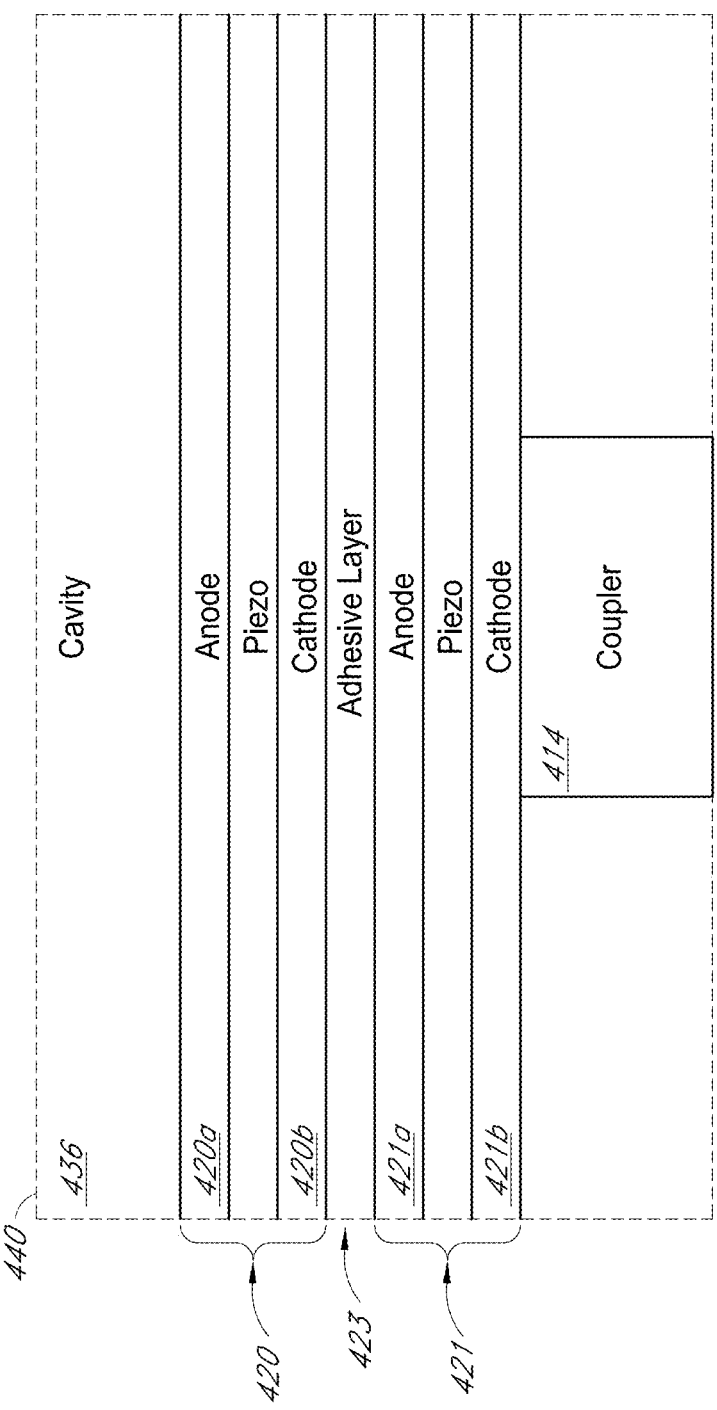
FIG. 4B shows a cross-sectional schematic drawing of a portion of the first and second stacked sensing elements of FIG. 4A.

FIG. 4B shows a partial cross-sectional schematic drawing of a portion 440 of the first and second stacked piezoelectric films 420, 421 of FIG. 4A. As shown, each of the first and second piezoelectric films 420, 421 respectively include an anode 420a, 421a and a cathode 420b, 421b on opposing sides of the films 420, 421. In some embodiments, the films 420, 421 include one of the piezoelectric films described with respect to FIGS. 2B-E or 3A-C, for example.

As shown, the films 420, 421 are disposed with respect to each other in a stacked configuration such that the cathode 420b of the first film 420 is facing the anode 421a of the second film 421. Thus, these two inner electrodes 420b, 421a of the stack are generally sandwiched between the anode 420a of the first film 420 and the cathode 421b of the second film 421, which form the outer electrodes of the stack. The inner electrodes 420b, 421a can be operationally coupled to a sensing circuit (e.g., a differential amplifier) in the manner shown in FIG. 20B, advantageously providing improved signal-to-noise-ratio in some embodiments.

In addition, the outer electrodes 420a, 421b of the films 420, 421 can be configured to form layers of an electrical noise shielding barrier, providing the additional benefit of electrically shielding the sensor from external electrical noises. The electrical noises shielded (or at least partially shielded) can include electromagnetic interference (EMI) from various sources, such as 50 or 60 Hz (AC) noise, noise from other medical devices, and so forth. In some embodiments for example, the outer electrodes 420a, 421b of the first and second films 420, 421 form a barrier around the inner electrodes 420*b*, 421*a* of the first and second films 420, 421. Thus, a significant amount of external electrical noise is not directly incident on the inner electrodes 420*b*, 421*a*. The outer electrodes 420*a*, 421*b* can, for example, distribute at least a portion of the external electrical noise substantially equally to the inner electrodes 420*b*, 421*a*, which form the electrical poles of the sensor. For example, because the outer electrodes 420*a*, 421*b* may share a common potential (e.g., ground), noise incident on either of the outer electrodes 420*a*, 421*b* can be distributed equally to each electrode 420*a*, 421*b*. The equally distributed noise can then be capacitively coupled to the inner electrodes 420*b*, 421*a*.

Thus, in certain embodiments, because the noise is equally distributed, the noise signal components on the inner electrodes 420*b*, 421*a* will be substantially in phase. The physiological signal components can be substantially out of phase, on the other hand, due to the differential orientation of the inner electrodes 420*b*, 421*a* with respect to one another in some implementations. The noise signals can advantageously be removed or substantially removed, such as through a common-mode rejection technique as described herein. In certain embodiments, at least some of the external electrical noise is shunted or otherwise directed to ground instead of, or in addition to, being equally distributed to the inner electrodes 420*b*, 421*a*.

A variety of alternative configurations are possible. For example, more than two sensing elements (e.g., 2, 3, 4, 5 or more) may be arranged to provide electrical shielding and/or improved signal-to-noise ratio in some embodiments. Moreover, the particular polarities of the sensing elements 420, 421 of FIG. 4 are not intended to be limiting. In another embodiment, one or more of the sensing elements 420, 421 are flipped. For example, the sensing elements 420, 421 are flipped such that the anode 420*a* of the first sensing element 420 faces the cathode 421*b* of the second sensing element 421.

Additionally, shielding barriers formed using stacked sensing elements 420, 421 can provide improved coupling of bodily sounds to the sensor, improving sensor operation (e.g., sensor sensitivity, measurement reliability, etc.). Generally, portions of both the shielding barrier and the sensing element will tend to vibrate in response to the patient sounds. Thus, an uneven mechanical response between the shielding barrier and the sensing element may result in lost signal, affecting sensor performance. For example, shielding barriers including layers that are physically separate from the sensing element can be, in some cases, relatively stiffer than the sensing element. This can limit movement of the sensing element in response to vibrations, producing a corresponding limiting affect on sensor sensitivity. In contrast, where electrodes of the sensing elements are used as shielding layers, the shielding barrier and the sensing element are generally formed from the same type material and integrally connected. Thus, the sensor may be relatively more responsive to vibrations, improving sensor operation.

Moreover, each of the outer electrode shield layers in the stacked configuration can be evenly spaced from the respective inner electrode sensor poles, particularly across the mechanically active portions of the sensor (e.g., across the frame cavity 436 of FIG. 4A). The capacitance between the shield layer and sensor pole on a first side of the sensing element stack can be very highly matched (e.g., substantially equal to) with the capacitance between the shield layer and sensor pole on the opposing side of the stack. Thus, a stacked sensing element configuration can provide a more even distribution of external electrical noise to the poles of the sensing element, improving noise rejection.

According to certain aspects, the physical configuration of the electrodes of the first and second films 420, 421 can be tailored to provide improved electrical shielding. For example, the outer electrodes 420*b*, 421*a* can be plated using a material selected to provide enhanced shielding. Although other materials may be used, in one embodiment, the outer electrodes 420*b*, 421*a* are plated with silver ink. Moreover, in certain embodiments, the outer electrode coatings of the piezoelectric stack cover a greater portion of the surface area of the respective piezoelectric films than the inner electrode coatings. For example, the outer electrode coatings may cover a significantly larger portion of the surface area of the respective piezoelectric films than the inner electrode coatings. In certain embodiments, for example, the outer electrodes generally envelope or surround the inner electrodes or a substantial portion thereof when the films 420, 421 are in a stacked configuration. Thus, the amount of surface area of the inner electrodes which is exposed to electrical noise is reduced due to the mechanical and/or electrical barrier created by the surrounding outer electrodes.

Figure 5A:
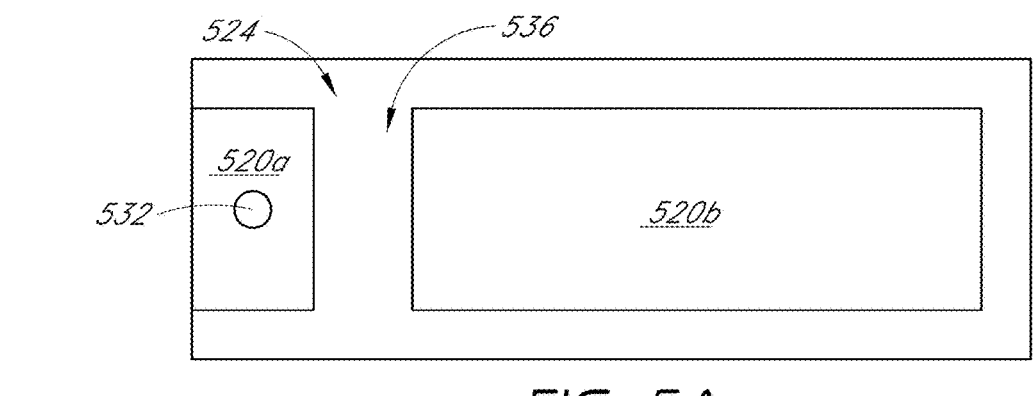
FIGS. 5A-5D show views of example acoustic sensing elements having electrode coating configurations tailored for use in a stacked configuration.
Figure 5B:
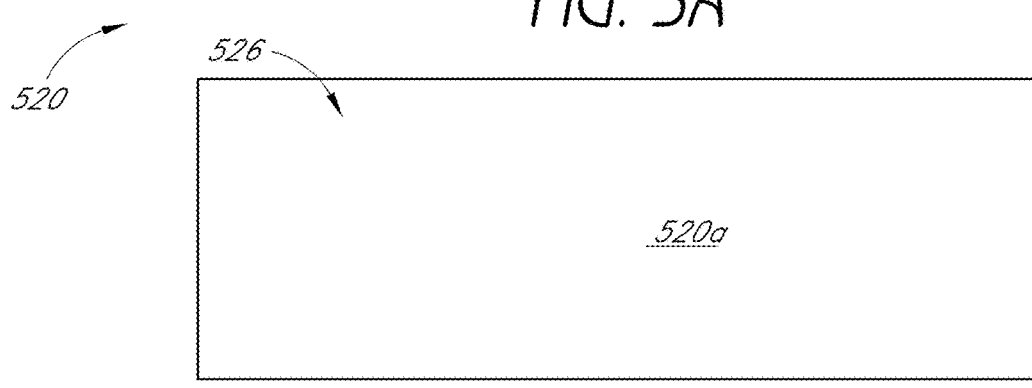
Figure 5C:
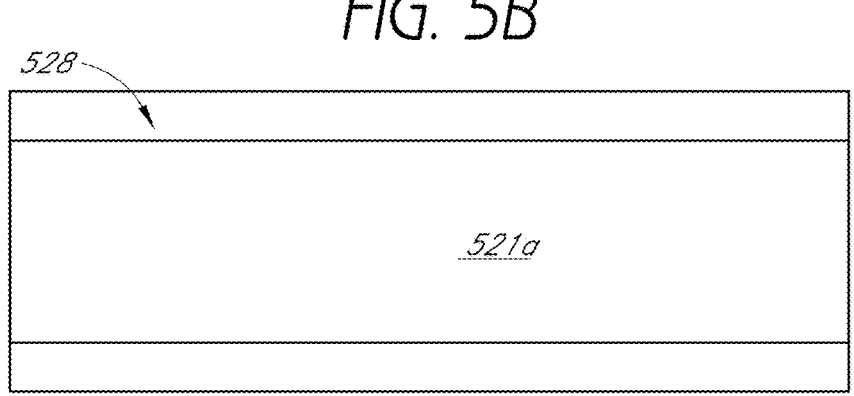
Figure 5D:
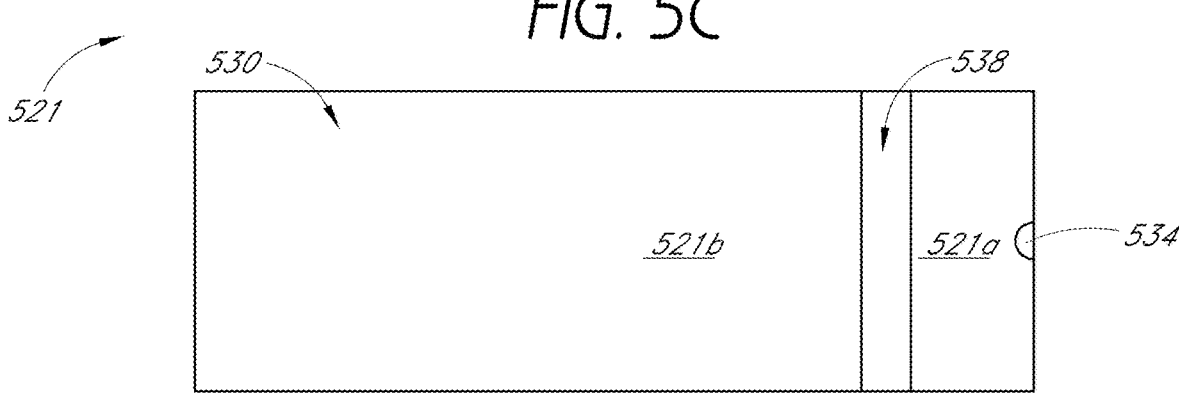

FIGS. 5A-5D illustrate example sensing elements 520, 521 having electrode coating configurations tailored for use in a stacked configuration. FIGS. 5A-5B show example first and second (e.g., inner and outer) surfaces 524, 526 of a first example acoustic sensing element 520. FIGS. 5C-5D show example first and second (e.g., inner and outer) surfaces 528, 530 of a second acoustic sensing element 521. While the films 520, 521 are shown in an unfolded configuration for the case of illustration, the second sensing element 521 may be wrapped around the first sensing element 520 on a frame as shown in FIGS. 4A-4B. Thus, the sensing elements 520, 521 are also referred to as the interior and exterior sensing elements, respectively.

The interior sensing element 520 includes an anode electrode coating 520*a* on the outer surface 526 which extends via a through hole 532 to a portion on one end the end of the inner surface 524. The inner surface 524 of the first sensing element 520 also includes a cathode coating 520*b*. The exterior sensing element 521 includes an anode electrode coating 521*a* on the inner surface 528 which extends via a through hole 534 to a portion on one end of the outer surface 530. The outer surface of the exterior sensing element 521 also includes a cathode electrode coating 521*b*.

As shown in FIG. 5B, the outer electrode surface of the first (interior) film 520 covers a substantially greater percentage of the surface area of the outer surface 526 of the film 520 than do the inner electrode surfaces on the opposing, inner surface 524 of the film 520, shown in FIG. 5A. For example, in the illustrated embodiment, the outer electrode coating shown on FIG. 5B covers substantially the entire outer surface 526 area of the film 520, while the electrode coatings on the inner surface 524 form a pair of generally rectangular strips covering only a portion of the inner surface 524 area of the film 520. Similarly, as shown in FIGS. 5C-D, the outer electrode coatings on the outer surface 530 of the second (exterior) film 521 covers a substantially greater surface area of the outer surface 530 of film 521 than the inner electrode coating on the inner surface 528 of the film 521. For example, in certain embodiments, the electrode coating on the exterior surface of one or more of the films 520, 521 covers at least 2 percent more of the film surface area than the do the interior electrodes. In other embodiments, the exterior electrodes cover at least 1, 5, 10, 15 or greater percent more of the exterior surface area than the do the interior electrodes. Additionally, the exterior electrode can cover at least 90 percent of the exterior film surface in some embodiments. In other embodiments, the exterior electrode covers at least 70, 75, 80, 85, 95 or more percent of the exterior film surface.

As described with respect to FIGS. 4A-4B, the through holes 532, 534 facilitate electrical contact between the respective electrodes and one or more components of the sensor (e.g., a PCB contact). Moreover, the electrode which is extended to the opposing side through the at least one through hole 540 can be electrically isolated from the other electrode on the respective film the by gaps 536, 538 in the electrode coatings.

In such embodiments, where an electrode coating covers substantially the entire surface area of the piezoelectric film, or otherwise covers a significantly larger portion of the surface area of the piezoelectric film than the electrode coating on the opposing side, the electrode coating may be referred to as "flooded." Thus, the configuration of FIG. 5 generally includes un-flooded inner electrodes generally sandwiched between flooded outer electrodes. Such configurations can reduce surface area of the inner electrodes that is exposed to electrical noise, improving electrical shielding.

A wide variety of flooded electrode configurations are possible. For example, in some embodiments, the sizes and shapes of the electrode coatings may differ from the illustrated embodiment. The relative sizes of the inner electrode coatings versus the outer electrode coatings can also vary. For example, the inner electrode coatings are much smaller in relation to the outer electrode coatings than is shown.

In some alternative embodiments, the outer and inner electrode coatings are both flooded or otherwise cover about the same surface area, or the electrode coating on the inner electrode coating covers more surface area than the outer electrode. Such embodiments may, in some cases, provide relatively less shielding than embodiments where the outer electrode coatings cover more surface area than the inner electrodes, but nonetheless provide some significant amount of electrical shielding.

Example Sensor

Figure 6A:
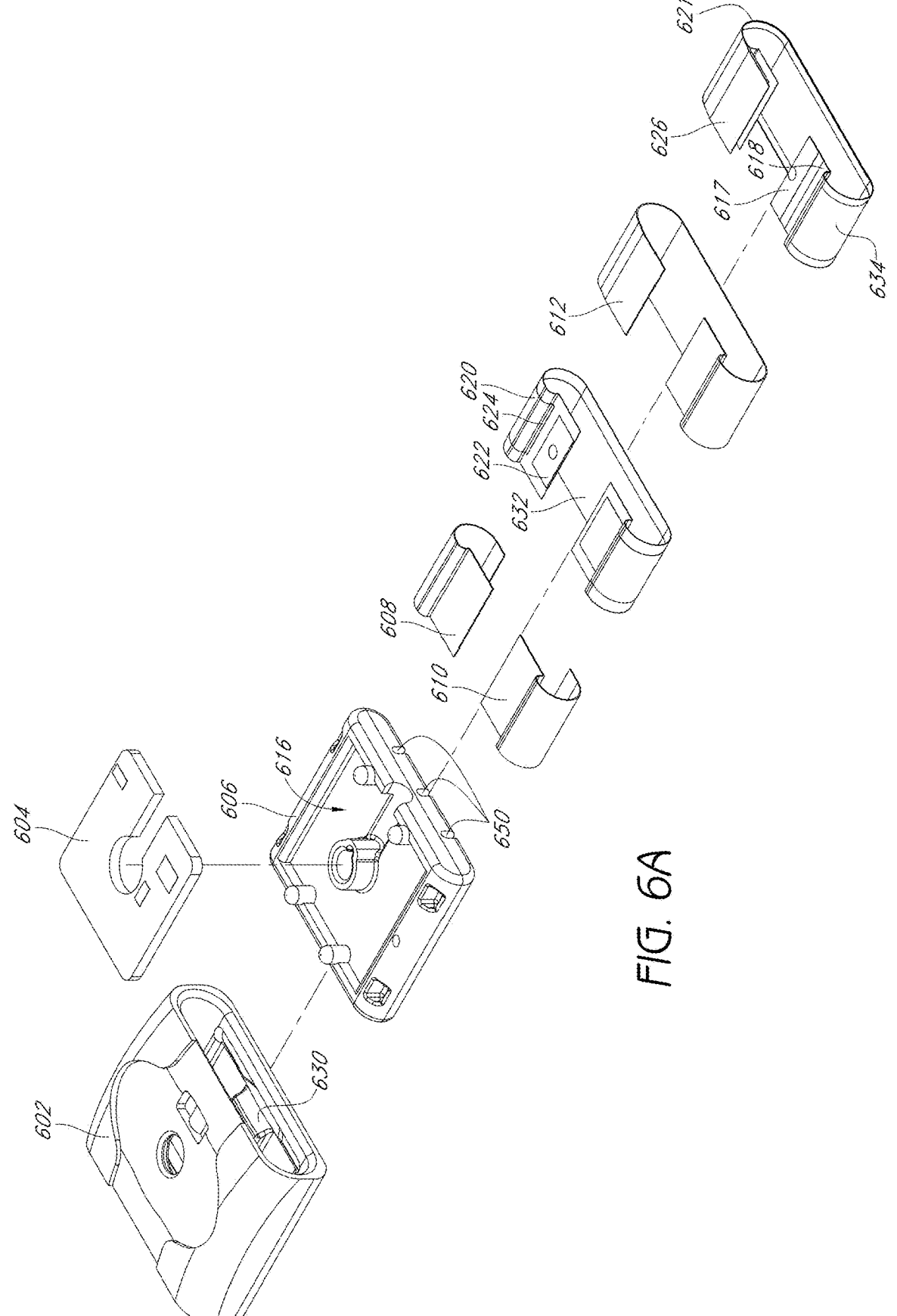
FIGS. 6A-6B are top and bottom exploded, perspective views, respectively, of a sensor incorporating multiple sensing elements in accordance with embodiments described herein.
Figure 6B:

FIGS. 6A-6B illustrate an exploded view of an example sensor 600 configured to detect acoustic physiological sounds from the patient incorporating certain beneficial aspects described herein. For example, the sensor 600 provides improved SNR using multiple sensing elements according to techniques described above with respect to FIGS. 2A-4B. Moreover, the sensor 600 includes a stacked, multiple sensing element configuration providing enhanced shielding, compatible with the techniques described above with respect to FIGS. 4A-5D.

The sensor 600 is generally attachable to a patient and can be coupled to a patient monitor. For example, the sensor 600 can be used with the system 10 of FIGURES IA-1B. Additionally, the sensor 600 may be compatible with the sensor system 100 of FIG. 1C. For example, the sensor 600 may be the sensor 101 of FIG. 1C, and can include an attachment mechanism (not shown) for attaching the sensor to a patient, such as the attachment subassembly 104 of FIG. 1C.

Referring to FIG. 6A, the sensor 600 of certain embodiments includes an acoustic coupler shell 602, a printed circuit board (PCB) 604, a frame 606, first and second acoustic sensing elements 620, 621, and multiple adhesive layers 608, 610, 612. The coupler shell 602 houses the frame 606, which is generally configured to support various components of the sensor 600 in an assembled state, including the PCB 604, sensing elements 620, 621, and adhesive layers 608, 610, 612. The sensing elements 620, 621 are piezoelectric films in the illustrated embodiment, although other types of sensing elements can be used.

The components of the sensor 600 can be assembled similarly to the sensor 415 of FIG. 4A. For example, the first piezoelectric film 620 is wrapped around a portion of the frame 606 and extends across an acoustic cavity 614 (FIG. 6B) of the frame 606 in tension. When assembled, the adhesive portions 608, 610 are positioned between interior opposing sides of the first film 620 and corresponding sides of the sensor frame 606, thereby adhering the first film 620 in place with respect to the frame 606.

The adhesive layer 612 is wrapped around the first sensing element 621, and the second sensing element 621 is in turn wrapped around the adhesive layer 612, generally forming a piezoelectric stack. As discussed with respect to FIG. 4A, the active portions of the films 620, 621 that extend across the acoustic cavity 614 are thus generally free to move in response to received vibrations, enabling detection of a physiological signal when the sensor 600 is attached to the patient. In certain embodiments, the acoustic cavity 614 or a portion thereof extends all the way through the frame 606. For example, the cavity may form one or more holes in the interior portion of the frame 606.

The PCB 604 is positioned in the cavity 616 (FIG. 6A) such that the underside of the PCB 604 comes into contact with the regions 617, 618 of the second film 621 and the regions 622, 624 of the first film 620. The flap 626 of the second film 621 rests on top of the PCB 604 in the illustrated embodiment, allowing electrical coupling of the first sensing element 620 to the PCB 604 and associated circuitry.

The coupler shell 602 is generally configured to transmit vibrations received from the patient to the films 620, 621 in the piezoelectric stack. The acoustic coupler 602 can include a lower protrusion or bump 628 (FIG. 6B) configured to press against the patient's body when the acoustic sensor 600 is fastened into place on the patient. The acoustic coupler 602 can also include a protrusion 630 (FIG. 6A) designed to abut against the films 620, 621 and to bias them in tension across the acoustic cavity 614. The coupler shell 602 can be similar to any of the acoustic couplers described herein, such as those described below with respect to FIGS. 19A-19E, 21, and 22A-22B.

Generally, the piezoelectric films 620, 621 can be any of those described herein. In the illustrated embodiment, for example, the films 620, 621 are the piezoelectric films described in FIGS. 5A-5D having flooded electrode surfaces 632, 644, respectively, which form the outer surfaces of the piezoelectric stack. Moreover, the films 620, 621 include one or more vias or through holes extending an electrode from one surface of the film 620, 621 to a corresponding region 622, 617 on the opposing surface of the respective film 620, 621. As discussed above, this configuration enables coupling of the four electrodes (e.g., the anode and cathode for each film 620, 621) to the appropriate contacts on the underside of the PCB 222.

For example, in one embodiment, the region 618 (FIG. 6A) of the flooded cathode coating on the outer surface of the second film 621 touches one or more of the contacts 636 on the underside of the PCB 604 (FIG. 6B). Meanwhile, the through-holed region 617 (FIG. 6A) of the outer surface of the second film 621, which includes an anode coating, touches the contact 638 on the underside of the PCB 604 (FIG. 6B). Regarding the first film 620, the region 624 (FIG. 6A) of the cathode coating on the inner surface touches one or more of the contacts 640 on the underside of the PCB 604 (FIG. 6B). Meanwhile, the through-holed region 622 (FIG. 6A) of the inner surface of the first film 620, which includes an anode coating, touches one or more of the contacts 642 on the underside of the PCB 604 (FIG. 6B).

According to the above-described connection scheme, the films 620, 621 can be coupled to circuitry (not shown) residing on the PCB 222 or other system component (e.g., the hub or monitor) to provide improved SNR and/or electrical shielding. For example, the electrodes of the films 620, 621 can each be coupled to an input of an attenuation circuit (e.g., a differential amplifier) or ground (or other common potential) in the manner illustrated schematically with respect to FIG. 3B above. Specifically, although other connections schemes are possible, in one embodiment, the contact 636 on the PCB 604 couples the flooded, outer cathode of the second, exterior film 621 to ground, and the contact 642 couples the outer, flooded anode of the first, interior film 620 to ground. Moreover, the contacts 642 couple the inner, un-flooded anode of the second, exterior film 621 to a first (e.g., positive) terminal of a difference amplifier or other noise attenuation circuit. Finally, the contacts 638 couple the un-flooded, inner cathode of the first, interior film 620 to a second (e.g., negative) terminal of the difference amplifier.

The frame 606 can include one or more pressure equalization pathways 650. The pressure equalization pathways 650 provide an air communication pathway between the lower acoustic cavity 614 and ambient air pressure. The pressure equalization pathways 650 allow the sensor's membrane(s) or film(s) 621, 622 to vibrate within the cavity 614 independent of skin elasticity or the force used to attach the sensor to a patient's skin.

Indeed, variability in skin elasticity or the force used to attach the acoustic sensor to the medical patient's skin can affect the volume and/or air pressure within the cavity 614 defined by the sensing elements 621, 622 and frame 606. Variability in skin elasticity or attachment force can lead to variability in cavity resonance, which can cause unwanted variability in sensor 600 performance. For example, an acoustic sensor 600 that is attached to very elastic skin may provide a different output signal than an acoustic sensor 600 that is attached to firmer or tighter skin. Similarly, an acoustic sensor 600 that is loosely attached to patient's skin may provide a different output signal than an acoustic sensor 600 that is tightly attached to a patient's skin.

To compensate for attachment variability, in one embodiment the acoustic sensor frame 606 includes one or more pressure equalization pathways 650. The pathways 650 provide an air-flow channel from the cavity 614 to the ambient air pressure. By equalizing pressure within the cavity 614 with ambient during sensing, variability in sensor performance may be reduced and/or eliminated. In some embodiments, the pressure equalization pathways 650 include one or more holes, notches, ports, or channels that extend from within the sensor's cavity 614 to a location in communication with ambient air pressure.

In one embodiment, the pressure equalization pathways 650 are provided on opposite sides of the frame 606 portion that defines an acoustic cavity 614. Symmetrically arranging the pressure equalization pathways 650 can further improve sensor 600 performance. In another embodiment the pressure equalization pathways 650 are provided in portions of the sensor frame 606 which do not contact the sensor's sensing elements, membranes, and/or films 621, 622. By preventing contact between the pressure equalization pathways 650 and the sensor's sensing membrane, sensor 600 performance may be further improved.

In one embodiment, the sensor frame 606 includes one, two, three, four, or five pressure equalization pathways 650 on each of two opposite sides of the sensor frame 606. In another embodiment, the sensor frame 606 includes at least one pressure equalization pathway 650 on each of its sides. In one embodiment, each pressure equalization pathway 650 is formed as a notch. A frame 606 that includes notches as its pressure equalization pathways 650 may be easier to fabricate than a frame that includes other pressure equalization pathways 650 (e.g., holes). For example, when the frame 606 is made by molding plastic, creating notches in the frame's 606 side wall requires less complicated tooling than forming holes.

Aspects of some of the components of the sensor 600 are described in greater detail herein with respect to other embodiments. For example, one or more of the coupling shell 602, PCB 604, frame 606, sensing elements 620, 621, adhesive layers 608, 610, 612, or portions or aspects thereof are compatible with the corresponding components shown in FIGS. 19A-23E and described in the accompanying text.

Noise Compensation Overview

Embodiments of systems generally including at least first and second acoustic sensing elements and configured to provide noise compensation will now be described with respect to FIGS. 7-18. As will be described, according to some aspects, one of the sensing elements is used as a physiological signal sensing element, and another is used as a noise sensing element for generating a noise reference signal. The noise reference signal can be used to generate a physiological signal have a reduced noise component according to a variety of techniques described in further detail herein (e.g., adaptive filtering techniques). Moreover, according yet other embodiments, the sensing elements are selectively configurable for use as either physiological signal sensing elements or noise sensing elements, as desired, as described in further detail herein.

According to various aspects, the multiple acoustic sensing elements can be beneficially arranged in a variety of configurations. For example, the first and second sensing elements can be incorporated into the same sensor package, as shown in the embodiments illustrated in FIGS. 8 and 10-15. In some embodiments, the first and second sensing elements are included in separate sensor packages, or can otherwise be strategically positioned at a variety of locations in the monitoring environment. For example, such sensors can be positioned at multiple locations on the patient, as is shown in and described with respect to FIG. 9A. Moreover, one or more sensing elements can be positioned at the physiological monitor or some other appropriate location in monitoring environment, as is disclosed in FIG. 9B and the accompanying text.

Generally speaking, the interfering noise signals described herein (e.g., with respect to FIGS. 7-18) can include any acoustic signal, and can include vibrational, sonic, infrasonic, or ultrasonic waves. Such signals can be transmitted in gases, liquids and/or solids. For example, depending on the physiological signal being monitored, the interfering noise can include patient sounds generated from physiological processes, such as breathing sounds, heart sounds, digestive sounds, combinations of the same and the like. Interfering noise can further include speech sounds, snoring, coughing, gasping, etc., and can emanate from the patient or other individuals in the monitoring environment. Further sources of noise can also include humming or other acoustic noise coming from computers or other electronic equipment in the operating environment, ambient traffic or airplane noise, combinations thereof and the like.

Interfering noise can additionally emanate from one or more noisy devices that are coupled to the patient, such as medical devices that are coupled to the patient during use. Examples of such devices can include, without limitation, powered surgical equipment (e.g., electrosurgical tools for cauterizing, coagulating, welding, cutting, etc.), ventilation equipment (e.g., continuous positive airway pressure (CPAP) machines), nebulizers, combinations of the same and the like.

Particularly where a noise source is readily identifiable, the noise sensing element according to certain aspects may be positioned in physical proximity to the noise source, so as to obtain a signal including a relatively clean noise reference signal, allowing for improved noise compensation according to techniques described herein. Specific example cases are provided below with respect to FIGS. 9A-9B, for example.

According to yet other described embodiments, it can be expected that the components of their output signals resulting from one source (e.g., the patient's body) will be generally similar while signal components from other sources (e.g., noise components) can be expected to have certain dissimilarities (e.g., phase or time shift). In these cases, the output signals from the first and second acoustic sensing elements can be advantageously combined in ways that accentuate commonalities between the two signals while attenuating differences between the two output signals, or vice versa, producing a reduced noise output signal.

Moreover, while shown and described as first and second sensing elements with respect to many of the embodiments described below, there may be more than two (e.g., 3, 4, 5 or more) sensing elements in certain embodiments. Additionally, while described as individual sensing elements for the purposes of illustration, in certain embodiments one or more of the first and second sensing elements each include multiple acoustic transducers or other types of sensing elements. In some embodiments, for example, the first and/or second sensing elements each include at least two piezoelectric films arranged in a stacked configuration, wrapped around a support frame, as described above with respect to FIGS. 3B-4B and 6A-6B.

Figure 7:
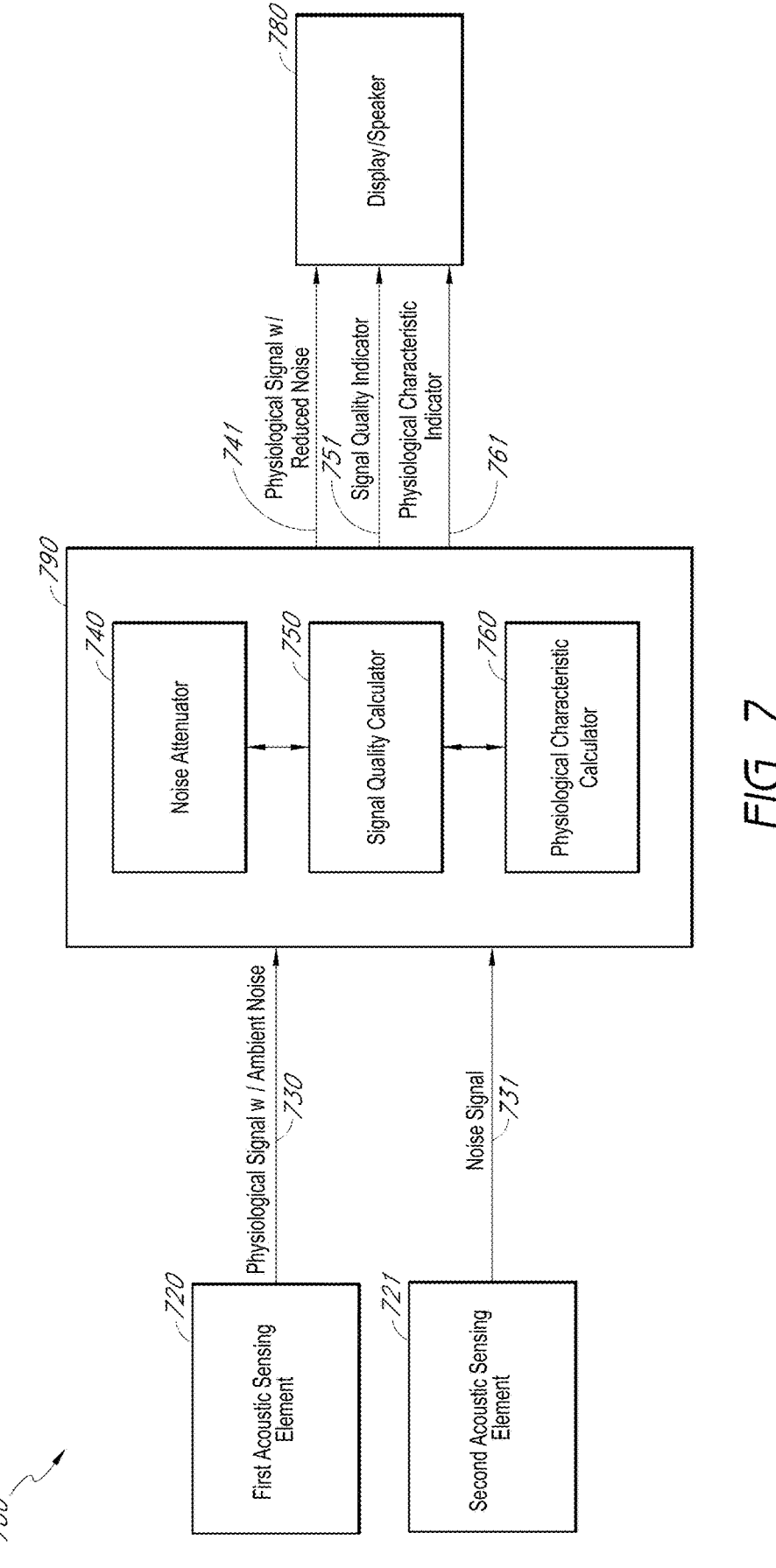
FIG. 7 is a block diagram of an example acoustic physiological monitoring system having noise compensation features.

FIG. 7 is a block diagram of an embodiment of an acoustic physiological monitoring system 700 having noise compensation features. The noise compensation features can be useful for reducing any deleterious effect of acoustic noise on the accuracy of physiological characteristics determined using the monitoring system 700.

The acoustic physiological monitoring system 700 includes a first acoustic sensing element 720 and a second acoustic sensing element 721. In some embodiments, these acoustic sensing elements are passive devices. In some embodiments, the first acoustic sensing element 720 is used to produce a physiological signal 730 that is indicative of one or more physiological sounds (e.g., sounds resulting from physiological processes) emanating from a patient's body. For example, the first acoustic sensing element 720 may be used to produce a physiological signal 730 that is indicative of a particular type of physiological sound, which is sometimes referred to herein as the target physiological sound. A variety of target physiological sounds are possible, including breathing sounds, heart sounds, digestive sounds, and the like. For example, the sensing elements 720, 721 can be piezoelectric films. In general, this physiological signal 730 can include unwanted noise as a result of interfering noise in the patient's surroundings being picked up by the first acoustic sensing element 720. The physiological component and the noise component of the signal 730 can overlap in time and/or frequency content. Devices for detecting primarily physiological sounds emanating from the patient's body are disclosed more fully herein.

In some embodiments, the second acoustic sensing element 721 is used to produce a noise signal that is substantially representative of, or otherwise meaningfully correlated with, any noise picked up by the first acoustic sensing element 720. The noise signal 731 may not necessarily duplicate the noise component of the physiological signal 730. For example, the signal strength of the noise in the two signals 730, 731 can differ. Other differences between the noise signal 731 and the noise component of the physiological signal 730 are also possible. However, it can be advantageous for the second acoustic sensing element to be positioned and designed such that the noise signal 731 has some degree of commonality with the noise present in the physiological signal 730. In this way, the noise signal 731 can provide useful information to meaningfully reduce, remove, filter, cancel, separate out, etc. the noise from the physiological signal 730. Devices for detecting primarily noise sounds are disclosed more fully herein.

In addition, the second acoustic sensing element 721 can also be positioned and designed such that the noise signal 731 is substantially free of the physiological sounds picked up by the first acoustic sensing element 720, or such that such physiological sounds are a less-significant component of the noise signal 731 than they are of the physiological signal 730. While illustrated as producing a noise signal 731, in other embodiments discussed more fully herein the second acoustic sensing element is positioned and designed to provide a second physiological signal rather than a noise reference signal. For example, like the first sensing element 720, the second acoustic sensing element 721 may include both a significant physiological signal component and an interfering noise component. In such embodiments, the first and second physiological signals can be combined in certain ways so as to reinforce the physiological components of the two signals while reducing any noise components that can exist in the two physiological components. In other embodiments, this can be carried out using more than two acoustic sensing elements.

In some embodiments, the physiological signal mixed with noise 730 and the noise signal 731 are input to a processing unit 790. In some embodiments, the processing unit 790 includes a noise attenuator 740, a signal quality calculator 750, and a physiological characteristic calculator 760. The processing unit 790 can be implemented as one or more digital signal processors, one or more analog electric processing components, combinations of the same or the like, etc.

In some embodiments, the noise attenuator 740 reduces the amount of noise present in the physiological signal 730 based on information gleaned from the noise signal 731, as discussed in more detail herein. For example, the noise attenuator 740 can reduce the signal energy of the noise component of the physiological signal 730. Alternatively, or in addition, the noise attenuator 740 can reduce or remove a portion of the noise component of the physiological signal 730 over a particular frequency range. In some embodiments, the processing unit 790 outputs a physiological signal with reduced noise 741 using the noise attenuator 740. The signal 741 can also be provided to other sub-blocks of the processing unit 790 (e.g., the physiological characteristic calculator 760).

The signal quality calculator 750 is a device that is used to determine, for example, an objective indicator of the quality of the physiological information obtained from one or more acoustic sensing elements. This can be done, for example, by comparing the physiological signal 730 with the noise signal 731, as discussed further herein. The signal quality calculator 750 can also output an objective indicator of the degree of confidence in the accuracy of a physiological characteristic (e.g., respiratory rate) determined based on the physiological information collected from one or more acoustic sensors. The signal quality calculator 750 can also output a binary confidence indicator that selectively indicates low confidence and/or high confidence in the accuracy of the physiological characteristic. The processing unit 790 then outputs one or more signal quality indicators 751.

The physiological characteristic calculator 760 is used to determine, for example, one or more values or signals that are indicative of a physiological characteristic of the patient. For example, the physiological characteristic can be respiratory rate, expiratory flow, tidal volume, minute volume, apnea duration, breath sounds, riles, ronchi, stridor, and changes in breath sounds such as decreased volume or change in airflow. In some embodiments, a physiological characteristic is calculated using a processing algorithm applied to the physiological signal with reduced noise 741 that is outputted by the noise attenuator 740.

The physiological signal with reduced noise 741, the signal quality indicator 751, and the physiological characteristic indicator can be output to a display and/or speaker 780 to be viewed or heard by a caregiver. For example, in some embodiments, the physiological signal with reduced noise 741 is converted back to an audible sound by way of a speaker or other acoustic transducer so that it can be heard by a doctor and used for diagnosis of the patient. In some embodiments, the signal quality indicator 751 and the physiological characteristic indicator 761 are displayed on a screen. This information can take the form of a numerical value, a plotted signal, an icon, etc.

Although both the noise attenuator 740 and the signal quality calculator 750 are included in the example processing unit 790 shown, the processing unit 790 could include either the noise attenuator 740 or the signal quality calculator 750 in some embodiments.

In various embodiments, the first and second acoustic sensing elements 720, 721 can be either the same or different types of acoustic sensing elements. For example, in one embodiment, both of the sensing elements are piezoelectric films such as any of the films described herein. In such a configuration, each of the sensing elements 720, 721 may be housed in a separate sensor packaging. As an example where different types of sensing elements are used, the first sensing element 720 in one embodiment is a piezoelectric film, while the second sensing element is a microphone, vibrational sensor or other type of acoustic pickup device. Such an embodiment is described with respect to FIG. 15 below.

Additionally, the sensing elements 720, 721 may be physically separate from one another. For example, the sensing elements 720, 721 can be physically separated within a single wearable sensor package. In other embodiments, the first sensing element 720 may be located on a wearable sensor package, such as any of those described herein, while the second sensing element 721 may be located at some other location, such as, for example, on a cable, hub, monitor, or in another wearable sensor package at a different location on the patient, etc. Further embodiments of sensors including physically separate sensing elements are discussed herein, with respect to FIGS. 8-9B, for example.

While embodiments described herein advantageously employ multiple sensing elements to achieve noise compensation, in certain embodiments, noise compensation is achieved using a single sensing element. For example, the sensing element may be coupled to the patient and thus produce a signal including both physiological and noise components. However, in such embodiments, the noise reference signal may be extracted during periods when the physiological signal is inactive (e.g., in between patient breaths, heart beats, etc.). The extracted reference signal can then be used in accordance with techniques described herein to provide noise compensation.

Figure 8:
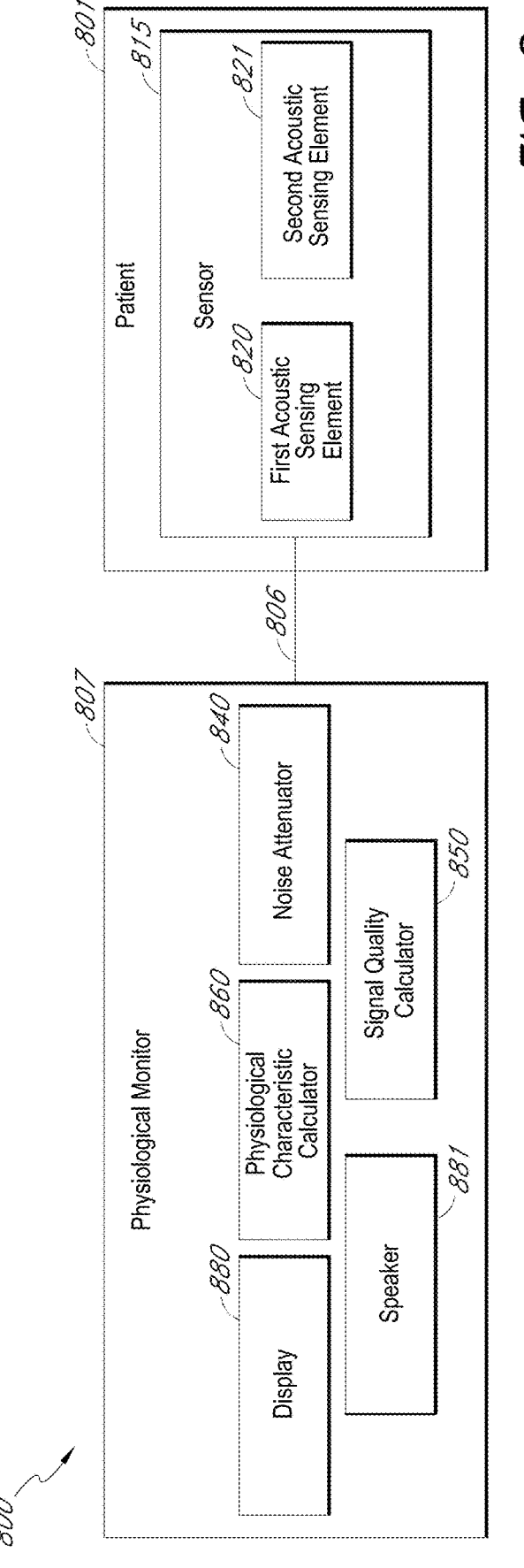
FIG. 8 is a block diagram of an embodiment of an acoustic physiological monitoring system with an acoustic sensor that includes first and second acoustic sensing elements.
Figures 9A, 9B:
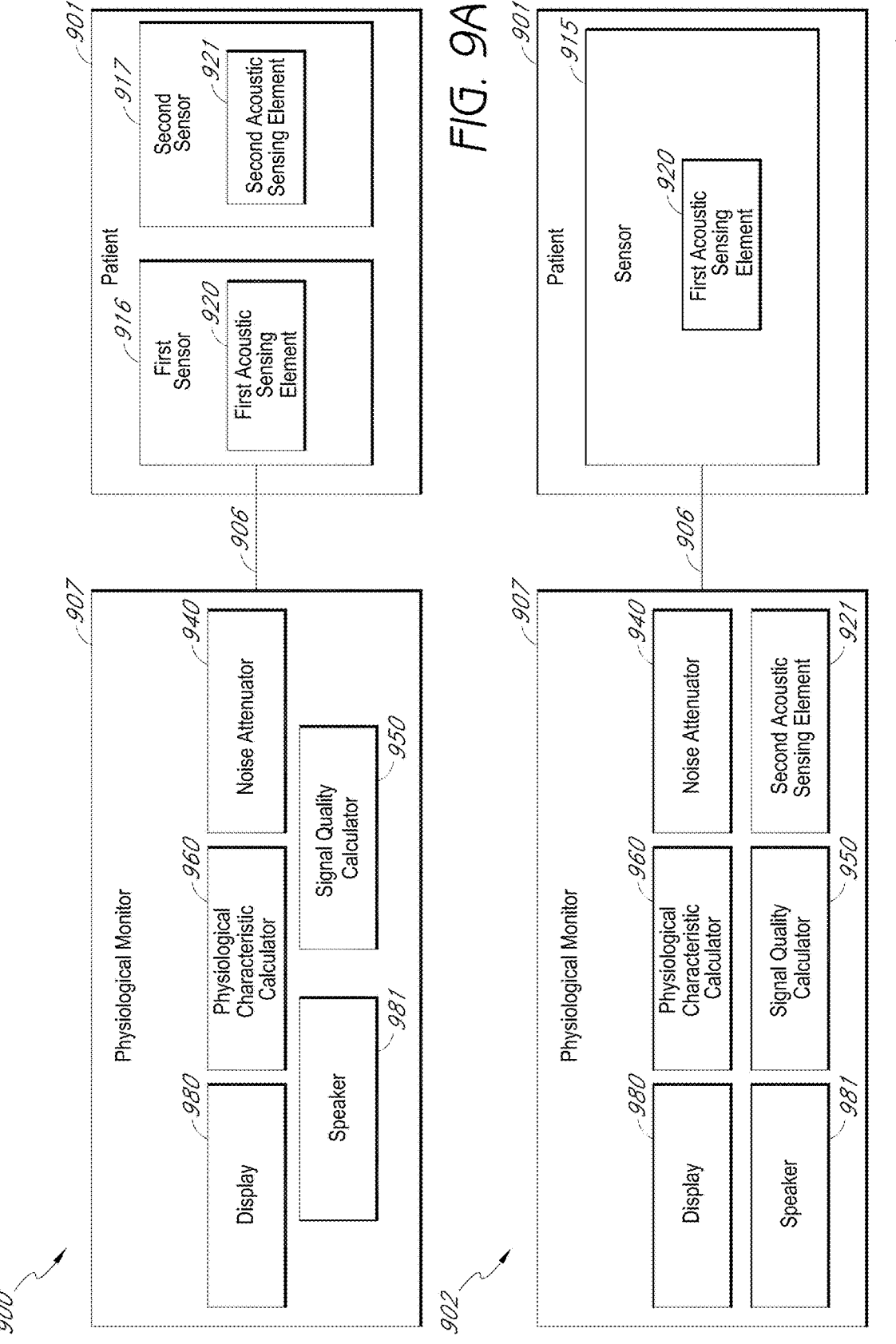
FIG. 9A is a block diagram of an embodiment of an acoustic physiological monitoring system with first and second acoustic sensing elements disposed in separate acoustic sensors.
FIG. 9B is a block diagram of an embodiment of an acoustic physiological monitoring system with an acoustic sensor that includes a first acoustic sensing element, and a physiological monitor unit that includes a second acoustic sensing element.

FIG. 8 is a block diagram of an embodiment of an acoustic physiological monitoring system 800 with a wearable acoustic sensor 815 that includes first and second acoustic sensing elements 820, 821. The first and second acoustic sensing elements 820, 821 are, for example, transducers for converting sound waves into some other form of energy (e.g., electrical voltage or current signals) to be processed, measured, etc. The first and second acoustic sensing elements 820, 821 can be packaged in a common housing as shown in FIG. 8, or in separate housings, as shown in FIG. 9A, described below. In some embodiments, the first and second acoustic sensing elements 820, 821 are both the same type of acoustic transducer. For example, in some embodiments, the first and second acoustic sensing elements 820, 821 are both piezoelectric films.

Even in cases where the first and second acoustic sensing elements 820, 821 are generally the same type of acoustic transducer, they need not be identical. For example, in the case where both of the first and second acoustic sensing elements 820, 821 are piezoelectric films, the material properties of the two films can be separately adapted based on known characteristics of the aural signals they are intended to sense. The first and second acoustic sensing elements 820, 821 can be made of different piezoelectric materials, they can have different shapes and thicknesses, they can have different support/mounting structures, and they can have different packaging. For example, in a given application (e.g., a medical sensing application), system designers can have foreknowledge regarding the characteristics of the sought-after acoustic signals.

As described herein, in some embodiments, the first acoustic sensing element 820 is used to primarily sense physiological signals, while the second acoustic sensing element 821 is used primarily to sense noise. In such cases, the type of piezoelectric material, and its shape, thickness, its mounting and packaging, etc. can be adapted for each of the acoustic sensing elements 820, 821 based on unique characteristics (e.g., frequency range, amplitude, etc.) of the physiological signals and the expected noise, respectively, if such unique characteristics exist and are identifiable.

In other embodiments, it is advantageous for the properties (e.g., material properties, mounting, packaging, etc.) of the first and second acoustic sensing elements 820, 821 to be substantially similar or even identical. This can be the case, for example, where the acoustic signals to be sensed by the two acoustic sensing elements 820, 821 have no important pre-identifiable differing characteristics.

It can also be advantageous for the first and second acoustic sensing elements 820, 821 to be substantially similar or even identical in terms of material properties, mounting, and packaging so that their signal outputs will likewise have shared characteristics in response to excitation of the acoustic sensing elements by a common source. This can be the case where the outputs of the first and second acoustic sensing elements 820, 821 are to be combined using techniques for selecting or rejecting signal components from the two sensing element outputs based on their common or distinguishing features. Examples of such techniques are described in further detail herein.

In other embodiments, the first and second acoustic sensing elements 820, 821 are different types of acoustic transducers. For example, the first and second acoustic sensing elements 820, 821 can be independently selected from a group including, but not limited to, piezoelectric acoustic transducers, condenser acoustic transducers, MEMS acoustic transducers, and electromagnetic induction acoustic transducers. Other types of acoustic transducers can also be used.

The first and second acoustic sensing elements 820, 821 can exhibit directionality or not. In cases where both of the first and second acoustic sensing elements 820, 821 exhibit directionality, they can be aimed at a common location (e.g., the patient's skin) or a different location (e.g., the first acoustic sensing element 820 could be aimed at the patient's skin to detect physiological sounds, while the second acoustic sensing element could be directed away from the patient's skin so as to detect ambient noise). In addition, in some embodiments, one of the acoustic sensing elements can exhibit directionality while the other does not. For example, in some embodiments the first acoustic sensing element 820 can exhibit directionality and be aimed at the patient's skin for detecting physiological sounds, while the second acoustic sensing element 821 does not exhibit directionality so as to detect noise from all directions.

As described herein (e.g., with respect to acoustic sensor 201), the acoustic sensor 815 can include a cable 806, or other communication link, for communicating with a physiological monitor 807. For example, one or more connectors, hubs, or other cables may be included as described herein. The acoustic sensor can also include one or more devices (e.g., electrical circuits) for detecting, processing, and transmitting the outputs from the first and second acoustic sensing elements 820, 821. The sensor can also include a fastener for fastening the sensor to the body of a patient. In some embodiments, the fastener is specially adapted to attach to the patient's neck or chest region in order to sense breathing sounds. The acoustic sensor 815 can also include other features described with respect to acoustic sensor 201.

In some embodiments, the acoustic sensor 815 is adapted to be communicatively coupled with a separate physiological monitor 807 that is not worn by the patient 801. (The physiological monitor 807 can include, for example, a display 880, a physiological characteristic calculator 860, a noise attenuator 840, a speaker 881, and a signal quality calculator 850, as described herein.) Thus, in some embodiments, the first and second acoustic sensing elements 820, 821 are disposed on or in an acoustic sensor 815 that is adapted to be worn by the patient 801, while the signal outputs from the first and second acoustic sensing elements 820, 821, which can include the raw signals directly from the acoustic sensing elements 820, 821 as well as processed signals derived therefrom, are transmitted to a separate physiological monitor 807 that is not worn by the patient 801. In other embodiments, however, the acoustic sensor 815 and the physiological monitor 807 can both be wearable by the patient 801.

As discussed herein, in some embodiments the first acoustic sensing element 820 is designed and used primarily to sense an acoustic physiological signal emanating from a patient's body, while the second acoustic sensing element 821 is used primarily to sense the acoustic noise. The first acoustic sensing element 820 can, however, also detect acoustic noise. In this case, the noise signal from the second acoustic sensing element 821 can be used as a noise reference to yield information that can be used to reduce or remove the presence of the acoustic noise from the physiological signal at the output of the first acoustic sensing element 820.

In cases where the second acoustic sensing element 821 is used to produce a noise reference signal, it can be advantageous for the first and second acoustic sensing elements 820, 821 to be designed and positioned with respect to one another such that the noise reference signal produced by the second acoustic sensing element 821 shares one or more characteristics with the noise component of the physiological signal output by the first acoustic sensing element. For example, the noise reference signal can be meaningfully correlated with the noise component of the physiological signal. In some embodiments, the noise reference signal from the second acoustic sensing element 821 and the noise component of the physiological signal from the first acoustic sensing element 820 are related by, for example, a scalar factor, a time shift, a phase shift, or combinations of the same. Other relationships between the noise reference signal and the noise component of the physiological signal are also possible.

In some embodiments, clinically meaningful correlation between the noise reference signal and the noise component of the physiological signal is achieved, at least in part, by placing the first and second acoustic sensing elements 820, 821 in proximity to one another. For example, as illustrated in FIG. 8, the first and second acoustic sensing elements 820, 821 can be commonly located on a wearable acoustic sensor 815. Disposing the first and second acoustic sensing elements 820, 821 in proximity to one another can improve correlation between the noise reference signal and the noise component of the physiological signal by reducing differences in, for example, the amplitude, frequency content, and phase between the noise sensed at the first acoustic sensing element 820 as compared to the noise sensed at the second acoustic sensing element 821.

The physical distance between the first and second acoustic sensing elements 820, 821 can vary from embodiment to embodiment depending upon, for example, the expected frequency content of the noise, the presence of acoustically dispersive materials, acoustic reflectors or absorbers, or the like, that are located, for example, between the two sensing elements. For example, a physiological monitoring system 800 operated in an environment with relatively lower frequency noise (e.g., ambient noise) can be able to tolerate larger physical distances between the first and second acoustic sensing elements since such distances will be smaller relative to the wavelength of the noise than in the case of noise with higher frequency content. Thus, even despite a relatively larger physical separation between the first and second acoustic sensing elements, the noise sensed by the second acoustic sensing element can still be reasonably indicative of, or related to, the noise sensed by the first acoustic sensing element.

In some embodiments, the actual tolerable physical distance between the first and second acoustic sensing elements 820, 821 can depend upon the particular application and/or noise-reducing requirements imposed by the application. In some embodiments, the first and second acoustic sensing elements 820, 821 can be physically disposed in close enough proximity to one another such that an noise reference signal detected by the second acoustic sensing element 821 contains a sufficient amount of information regarding the noise component of the physiological signal detected by the first acoustic sensing element 820 so as to provide a clinically significant reduction in the noise component of the physiological signal. This can be manifested, for example, by a clinically significant improvement in the accuracy of a physiological characteristic (e.g., respiratory rate) determined by the physiological monitoring system from a noise-reduced version of the physiological signal detected by the first acoustic sensing element 820.

In some embodiments, the first and second acoustic sensing elements are physically located within a 1 m radius of one another. In some embodiments the first and second acoustic sensing elements are physically located within a 0.1 m radius of one another. In some embodiments the first and second acoustic sensing elements are physically located within a 0.01 m radius of one another. In some embodiments the first and second acoustic sensing elements are physically located within a 0.001 m radius of one another.

In some embodiments, the first and second sensing elements 820, 821 can be disposed in separate sensor packages or otherwise be disposed at different locations throughout the operating environment. For example, FIG. 9A is a block diagram of an embodiment of an acoustic physiological monitoring system 900 with first and second acoustic sensing elements 920, 921 disposed in or otherwise being associated with separate first and second sensors 916, 917. While shown as being coupled to the physiological monitor 907 via a single communication link 906, a separate communication link 906 may be used for each sensor 916, 917 in certain embodiments. In some embodiments, each communication link 906 includes one or more cables, hubs, and/or connectors as described herein. FIG. 9B is a block diagram including a first sensing element 920 disposed on a patient and a second sensing elements 920, 921 disposed on a physiological monitor 907.

Referring to FIG. 9A, the first and second sensors 816, 817 can be positioned at a variety of locations on the patient 901. For example, in certain embodiments, one or both of the sensing elements 920, 921 (and their associated sensors 916, 917) can be positioned on or around sources of sounds generated by physiological processes. Such areas can include those associated respiratory or vocal sounds including for example, the throat, back of the neck, mouth, or some other portion of the head or neck, on the back or chest around the lungs, combinations of the same and the like. Other sensing element locations can include those generally associated with heart sounds, such as on the chest around the heart, on the throat, on the wrist, etc. Yet other locations can include those typically associated with digestive sounds such as near the stomach or on some other portion of the abdomen. Moreover, while the above examples are provided for the purposes of illustration, depending on the application, the sensors 916, 917 can additionally be positioned at generally any location on the patient's body 901 including, for example, a hand, finger, arm, foot, leg, etc.

Figures 9C, 9D:
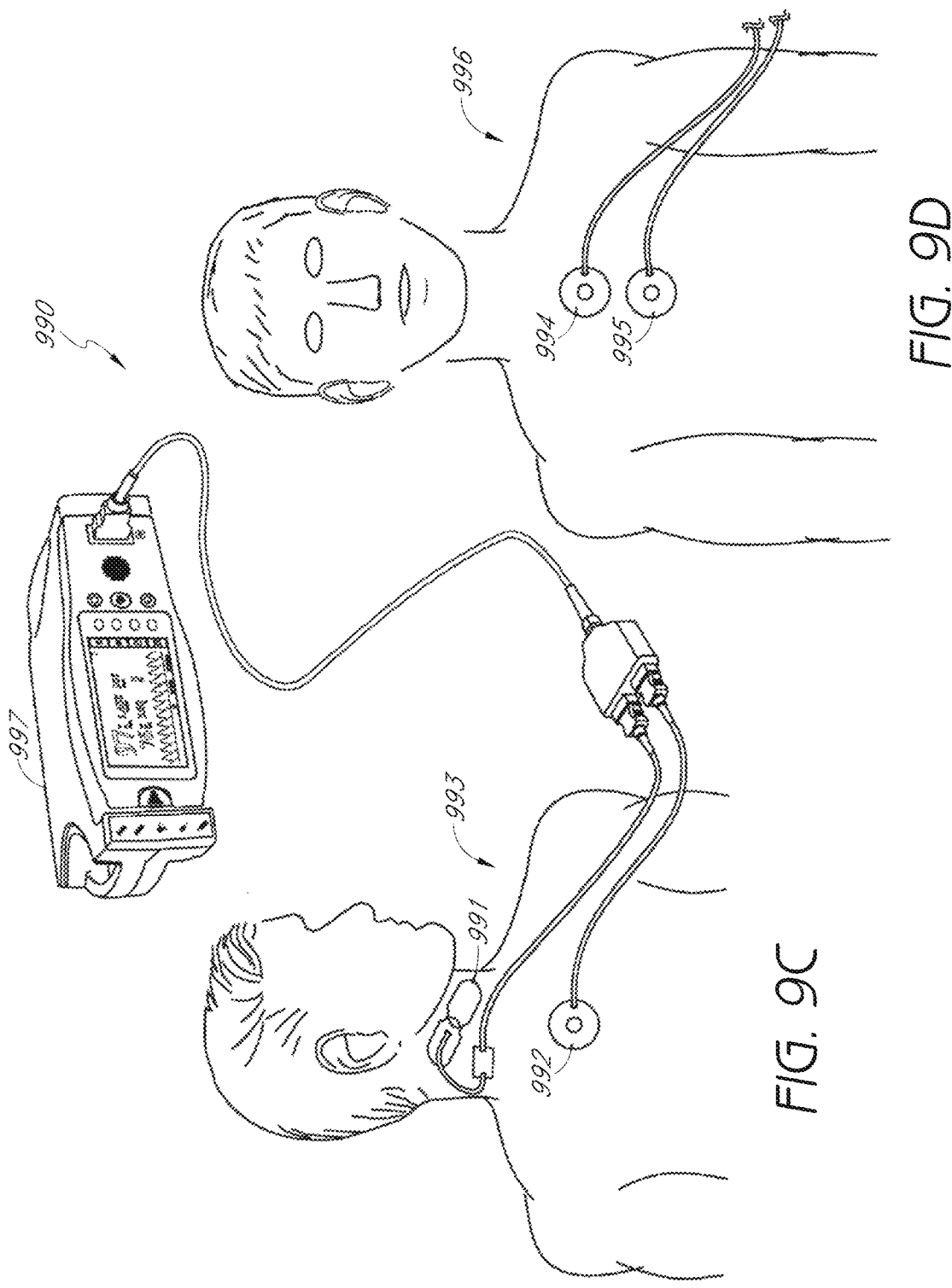
FIGS. 9C-9D illustrate example systems including dual acoustic sensors applied to a patient according to certain embodiments.

FIG. 9C illustrates an example system 990 including dual acoustic sensors 991, 992 applied to a patient's 993 throat and chest, respectively. FIG. 9D illustrates a second example where sensors 994, 995 are applied to different regions of a patient's 996 chest. The dual acoustic sensors 991, 992, 994, 995 can be coupled to a physiological monitor 997 via a hub and a plurality of cables, as shown. The sensors 991, 992, 994, 995, monitor 997, cables, hub, etc., can be any of those described herein or incorporated by reference, or can be some other acoustic sensors. Where multiple sensors are attached to the patient or are otherwise spatially separated throughout the operating environment, such an arrangement may be referred to as a stereo body sound monitoring environment that allows for stereo body sound monitoring.

The sensing elements 920, 921 and, where present, associated sensor packages, can additionally be positioned at one or more locations in the operating environment not on the patient's body. For example, FIG. 9B is a block diagram of an embodiment of an acoustic physiological monitoring system 902 with a wearable acoustic sensor 915 that includes a first acoustic sensing element 920, and a physiological monitor unit 907 that includes a second acoustic sensing element 921. The physiological monitor unit 907 is adapted to be communicatively coupled with the wearable acoustic sensor 915 via, for example, a cable 906. In some embodiments, the physiological monitor unit 907 is a non-wearable unit with one or more devices for processing signal outputs from the first and second acoustic sensing elements 920, 921. The physiological monitoring system 902 of FIG. 9B is similar to the physiological monitoring systems 800, 900 except that the second acoustic sensing element 921 is physically located at the non-wearable physiological monitor 907 instead of at the wearable acoustic sensor 915.

While shown on the monitor 907, the second sensing element 921 can be positioned at a variety of other locations. For example, in cases where the physiological monitor 907 and the acoustic sensor 915 are communicatively coupled using a physical cable 906, the cable 906 can be useful in placing a limit on the distance between the first and second acoustic sensing elements 920, 921 to ensure that they remain in close enough proximity with one another to provide for meaningful noise reduction for a given medical sensing application. In other embodiments, the second acoustic sensing element 921 can be at any intermediate location between the monitor and the sensor, such as on or in the cable 906, a connector, or a hub (not shown) such as the hub 120 of FIG. 1C, or generally at any separate location independent of the physiological monitor 907 or the acoustic sensor 915. Where the second sensing element 921 is used to generate a noise reference, positioning the second sensing element 921 on or in the monitor 907, hub, or at another intermediate location, rather than on the sensor 915 can advantageously reduce the wiring overhead in the system. On the other hand, it can be beneficial to locate the second sensing element 921 near the first sensing element 920 so as to generate a noise reference signal that is substantially correlated with the noise component of the signal detected by the first sensing element 920. Thus, in certain cases, a trade off generally exists between locating the second sensing element 921 in proximity to the first sensing element 920 to improve noise rejection on the one hand, and locating the second sensing element remote from the first sensing element 920 to reduce wiring overhead on the other. Thus, in circumstances, locating the second sensing element 921 at the hub or at another intermediate location between the monitor 907 and the first sensing element 920 provides the desired balance between reduced wiring overhead and adequate noise rejection.

As mentioned, where a noise source is readily identifiable, the second sensing element 921 can be positioned in physical proximity to the noise source. In this manner, the second sensing element 921 can be used to produce a signal including a relatively clean noise reference signal, allowing for improved noise compensation. Such noise sources can be those generating any of the interfering noise described herein such as non-target physiological sounds emanating from the patient (e.g., heart, breathing or digestive sounds), ambient noise (e.g., traffic, ambient speech sounds, computer humming, and the like), or vibrations or other noise emanating from skin-coupled devices (e.g., electrosurgical devices, CPAP machines, nebulizers, etc.).

Several example scenarios incorporating multiple sensing elements 920, 921 strategically located at separate locations in the operating environment will now be described. These examples are provided for the purposes of illustration, and are not intended to be limiting. As a first illustrative example, referring to FIG. 9A, the first sensor 916 is a physiological signal sensor and is positioned on or around a source of breathing sounds (e.g., the neck), while the second sensor 917 is a noise sensor and is positioned on or around the heart to detect heart sounds and/or other noise components. Thus, the signal from the second sensor 917 can be used to cancel or otherwise attenuate any residual heart sounds (and/or ambient or other noise) that may bleed into the signal produced by the first sensor 916.

In another example scenario, a CPAP machine or other medical device is coupled to the patient. The first sensor 916 is a physiological signal sensor positioned on the patient's heart to detect heart sounds, and the second sensor 917 is a noise sensor positioned on the CPAP machine or other medical device. Thus, the signal produced by the second sensor 917 can be used to cancel any residual noise from the CPAP machine (and/or ambient or other noise) that bleeds into the signal detected by the first sensor 916.

In yet another illustrative example, the first sensor 916 is a physiological signal sensor positioned to detect breathing sounds, and the second sensor 917 is a noise sensor positioned on the patient near a planned electrosurgical site (or on an electrosurgical device itself). The second sensor 917 can be used in such a situation to cancel noise generated by the electrosurgical device (and/or ambient or other noise) that bleeds into the signal detected by the first sensor 916.

Selective Configuration of Multiple Sensing Elements

Depending on the desired application, the multiple sensing elements can be selectively configured in a plurality of modes. For example, referring still to FIGS. 9A-9B, the sensing elements 920, 921 can be configured as either physiological signal sensors or noise sensors in some embodiments. In addition to physiological sensing and noise modes, the sensing elements can be configured in a variety of other modes. For example, in one embodiment, one or more of the sensing elements 920, 921 is configurable in an auscultation mode. For example, the sensing elements 920, 921 can be configured in a listening mode in which an operator can generally continuously listen to audio output indicative of patient bodily or voice sounds. In yet another embodiment, the sensing elements 920, 921 can be configured to sense and process ultrasonic signals (e.g., for ultrasonic imaging). Examples of sensors capable of various types of audio output, ultrasonic sensing, and other compatible functionality are provided in U.S. patent application Ser. No. 12/905,036, entitled PHYSIOLOGICAL ACOUSTIC MONITORING SYSTEM, filed on Oct. 14, 2010, incorporated by reference herein in its entirety.

As one example, the first sensor 916 is positioned on or around a source of breathing sounds (e.g., on the throat), while the second sensor 917 is positioned on or around the heart to detect heart sounds. In a first mode, the first sensor 916 is configured in a physiological sensing mode and the second sensor 917 is configured in a noise sensing mode, while in a second mode, the roles of the sensors are generally switched. In this manner, breathing sounds are monitored and the effect of heart sounds (and/or other noise) is reduced according to noise cancelling techniques described herein. Moreover, in the second mode, heart sounds are monitored, and the effect of any residual breathing sounds (and/or other noise) is reduced. Thus, according to such techniques, a user can flexibly and efficiently switch between monitoring reduced noise versions of a wide variety of physiological signals.

Moreover, the sensing elements can be configured for use in more than one mode at a time in certain embodiments. For example, each of the sensing elements 920, 921 can be configured simultaneously as both physiological signal sensing elements and noise sensing elements. In the above example scenario, the first sensing element 920 can be used to monitor breathing sounds and also generally simultaneously provide a noise reference to the second sensing element 921. Conversely, the second sensing element 921 can be used to monitor heart sounds and also generally simultaneously provide a noise reference to the first sensing element 920. While other modes are possible, in various embodiments, the sensing elements 920, 921 can be configured generally simultaneously for two or more of physiological signal sensing, noise sensing, auscultation, and ultrasonic sensing.

The configuration of the sensing elements 920, 921 may be manually selectable by a user, or can be automatically configurable by the system. For example, one or more user-actuatable inputs (e.g., buttons, switches, keypad inputs, etc.) may be provided to the user for setting the sensing element 920, 921 modes. Such inputs may be located on the monitor 907, in proximity to the sensing elements 920, 921 themselves, such as on the respective sensor packaging, or at some other appropriate location.

Moreover, the modes of the sensing elements 920, 921 can be configurable either as a group or individually in various embodiments. For example, referring to the above example where the first sensing element 920 is positioned to detect breathing sounds and a second sensing element 921 is positioned to detect heart sounds, the system may allow the user to select either of a breathing sound monitoring mode or a heart sound monitoring mode. Based on the selection, the system will appropriately automatically configure each sensing element 920, 921 mode. In another embodiment, the user sets each of the respective sensing element 920, 921 modes separately.

Where multiple sensing elements are present and are configured or selectively configurable for use as noise sensing elements, the system according to some embodiments automatically selects which sensing element or group thereof to use in the noise cancellation algorithm. Moreover, the outputs from multiple noise sensing elements or a selected combination thereof can be combined so as to provide improved noise rejection.

As one example, a first sensing element 920 is disposed on a wearable acoustic sensor 915 positioned on the patient's neck and is configured to receive a signal including physiological signal components and noise components. Second, third and fourth acoustic sensing elements are disposed on the cable, at the hub, and in the monitor, respectively, and are configured to receive noise signals.

In such embodiments, the physiological monitor 907 or other system component can generally use signals received from at least one of the noise acoustic sensing elements to perform noise reduction. For example, in the above example, each of the signals from the second, third and fourth sensing elements can be combined or otherwise used to perform noise compensation. In other cases, only a subset of one or more of the signals may be used as desired.

The system 900 can allow for manual selection of the noise acoustic sensing element(s) to use during monitoring, or can alternatively automatically select which of the noise acoustic sensors (e.g., the second third, or fourth sensing elements or a combination thereof) to use. Automatic selection can be performed in a variety of ways.

For example, in one embodiment, the system 900 evaluates the signals from each of the noise acoustic sensors, such as by assessing the magnitude or quality of the respective noise signals, and selects one or more of the signals to use based on the evaluation. For example, in some embodiments, the noise sensing element or combination of noise sensing elements that provides one or more of the highest amplitude noise reference signal or the cleanest noise reference signal is selected. In another embodiment, the system 900 assesses the degree of noise compensation achieved using the different noise acoustic sensing elements and/or combinations thereof, and selects the noise acoustic sensing element or combination thereof that provides the highest (or otherwise desirable) level of noise compensation to use during monitoring.

Noise Compensation Using Signal or Noise Correlation Between Sensing Elements

As described, it can be advantageous in certain embodiments for the first and second acoustic sensing elements to be substantially similar or even identical in terms of material properties, mounting, and packaging so that their signal outputs will likewise have shared characteristics in response to excitation of the acoustic sensing elements by a common source. This can be the case where the outputs of the first and second acoustic sensing elements are to be combined using techniques for selecting or rejecting signal components from the two sensing element outputs based on their common or distinguishing features.

For example, referring to FIGS. 9A-9B for the purposes of illustration, in some applications it can be expected that, owing to similarities in the design and placement of the first and second acoustic sensing elements 920, 921 or other factors, the components of their output signals resulting from a common source (e.g., the patient's body) will be generally similar while signal components from other sources (e.g., noise components) can be expected to have certain dissimilarities (e.g., phase or time shift). In these cases, the output signals from the first and second acoustic sensing elements 920, 921 can be combined in ways that accentuate commonalities between the two signals while attenuating differences between the two output signals.

In one example scenario, referring to FIG. 9A, the first and second acoustic sensing elements 920, 921 are substantially the same type and are included in separate sensor packages each placed on the patient. As described, the physiological signal components produced by the sensing elements 920, 921 are substantially correlated with respect to one another. In some cases, the correlation can be enhanced via strategic placement of the sensing elements 920, 921 with respect to one another. For example, the sensor packages can be placed generally symmetrically about the signal source (e.g., the throat or chest). In contrast, the noise signal components produced by the sensing elements 920, 921 are substantially uncorrelated with respect to one another.

In such a scenario, the components can be uncorrelated for a variety of reasons. For example, noise signals emanating from external sources may reflect off of the skin or sensor package before reaching the respective sensing element 920, 921. The signal may also propagate through a portion of the sensor package before reaching the respective sensing element 920, 921, causing additional distortions. Moreover, the degree and quality of distortion in the noise signal received by the sensing elements 920, 921 can differ significantly between the sensing elements 920, 921. For example, in addition to other possible reasons, the variation in distortion can be caused by a variation in the respective angle of arrival of the noise signal at each of the sensor packages. This can be due to the difference in the orientation of the noise source from one sensor package to another.

The output signals from the first and second acoustic sensing elements 920, 921 in such a scenario can be combined to accentuate the correlated physiological signal components and attenuate the uncorrelated noise components between the two output signals. For example, while a variety of techniques can be used, the outputs from the sensing elements are summed together in one embodiment. The correlated components will tend to additively combine, while the uncorrelated components will not, resulting in an overall improved SNR. In other embodiments, more than two (e.g., three, four, five or more) sensing elements 820, 821 are used.

In some other embodiments, certain noise components (e.g., ambient noise components) of the signals produced by the first and second sensing elements 920, 921 may be correlated, while the physiological signal components may be uncorrelated. In such cases, additional appropriate techniques can be used to generate a reduced noise signal. Examples of such techniques, including cross-correlation, are described in U.S. application Ser. No. 12/904,789, entitled ACOUSTIC RESPIRATORY MONITORING SYSTEMS AND METHODS, filed on Oct. 14, 2010, the entirety of which is incorporated by reference herein.

Additional Noise Compensation Embodiments

Figure 10:
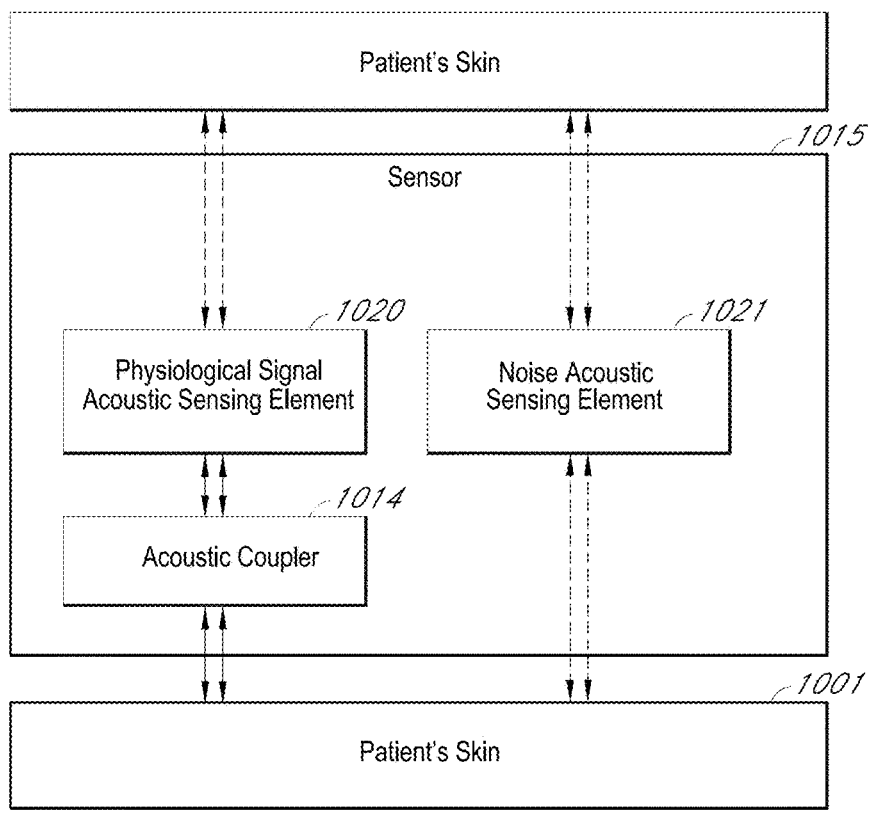
FIG. 10 is a block diagram of an embodiment of an acoustic sensor that includes a physiological signal acoustic sensing element with an acoustic coupler for acoustically coupling it to a patient's body, and a noise acoustic sensing element.

FIG. 10 is a block diagram of an embodiment of an acoustic sensor 1015 that includes a physiological signal acoustic sensing element 1020 with an acoustic coupler 1014 for acoustically coupling it to a patient's body, and a noise acoustic sensing element 1021. In some embodiments, the acoustic coupler 1014 is any device or structure, made using any material, that effectively enhances the transmission of acoustic signals from a patient's body to the physiological signal acoustic sensing element 1020. In the case where the physiological signal acoustic sensing element 1020 is a piezoelectric film, the acoustic coupler 1014 can be a mechanical structure in contact with both the patient's skin 1001 and the acoustic sensing element 1020 so as to transmit vibrations from the patient's body to the physiological signal acoustic sensing element. The acoustic coupler 1014 can be, for example, similar to the acoustic coupler 214 described herein. Other acoustic couplers can also be used. The acoustic sensing elements 1020, 1021 and the acoustic coupler 1014 can be physically supported in a desired spatial relationship with respect to one another using, for example, a suitable frame.

The acoustic coupler 1014 provides an amount of acoustic coupling between the physiological signal acoustic sensing element 1020 and the patient 1001 that is greater than the amount of acoustic coupling that can exist between the noise acoustic sensing element 1021 and the patient. This increased amount of acoustic coupling is illustrated in FIG. 10 by solid double arrows. Of course, the physiological signal from the patient's body 1001 can also be picked up by the noise acoustic sensing element 1021, just as noise can be picked up by both of the acoustic sensing elements 1020, 1021.

However, the strength of the physiological signal present in the output of the noise acoustic sensing element 1021 will typically be less than the strength of the physiological signal present in the output of the physiological signal acoustic sensing element 1020, as a result of the lack of an acoustic coupler between the patient's body 1001 and the noise acoustic sensing element 1021. This is illustrated in FIG. 10 by the dashed double arrows between the patient's skin 1001 and the noise acoustic sensing element 1021. For example, in some embodiments, the strength of the physiological signal in the output of the noise acoustic sensing element 1021 is less than 50% of the strength of the physiological signal in the output of the physiological signal acoustic sensing element 1020. In some embodiments, the signal strength of the physiological signal at the output of the noise acoustic sensing element 1021 is less than 25%, or less than 10%, or less than 5%, of its strength at the output of the physiological signal acoustic sensing element 1020.

In some embodiments, it is advantageous for the strength of the physiological signal in the output of the noise acoustic sensing element 1021 to be significantly less than the strength of the physiological signal in the output of the physiological signal acoustic sensing element 1020. In this way, the output of the noise acoustic sensing element 1021 can be effectively used as a noise reference signal to provide useful information for reducing the amount of noise present in the output of the physiological signal acoustic sensing element 1020.

While in some embodiments it is advantageous for the two acoustic sensing elements 1020, 1021 to be in close proximity so as to improve the degree of correlation between the noise picked up by each acoustic sensing element, it can be likewise advantageous for the noise acoustic sensing element 1021 to be located further away from the patient's body 1001 to reduce the strength of the physiological signal picked up by the noise acoustic sensing element 1021. In some cases, these two design goals can work in opposition to one another. However, in some embodiments, both advantages can be had by the addition of one or more acoustic decouplers or isolators to the acoustic sensor.

Figure 11:
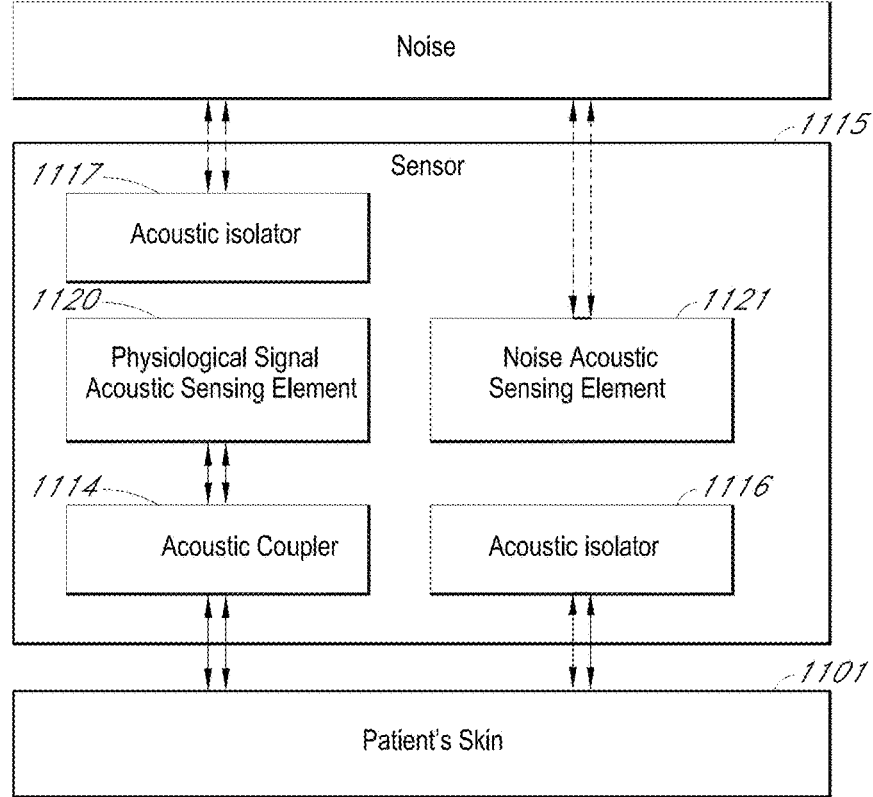
FIG. 11 is a block diagram of an embodiment of an acoustic sensor that includes a physiological signal acoustic sensing element with an acoustic coupler for increasing acoustic coupling between it and a patient's body, and a noise acoustic sensing element with an acoustic decoupler for decreasing acoustic coupling between it and the patient's body.

FIG. 11 is a block diagram of an embodiment of an acoustic sensor 1115 that includes a physiological signal acoustic sensing element 1120 with an acoustic coupler 1114 for increasing acoustic coupling between it and a patient's body, and a noise acoustic sensing element 1121 with an acoustic decoupler 1116 for decreasing acoustic coupling between it and the patient's body 1101. The acoustic decoupler 1116 reduces further the amount of physiological sounds from the patient's body that is picked up by the noise acoustic sensing element 1121. Acoustic decoupling can include, for example, complete acoustic isolation or substantial acoustic isolation of the sensing element 1121 from the patient's skin 1101. Thus, in certain embodiments, the acoustic decoupler 1116 can reduce sounds from being transmitted from the patient's skin 1101 to the sensing element 1121, or prevent the transmission of these sounds entirely.

This can be advantageous since the acoustic decoupler 1116 can provide for a higher degree of certainty that any similarities or correlation between the output of the noise acoustic sensing element 1121 and the output of the physiological signal acoustic sensing element 1120 are more likely to be indicative of the acoustic noise than the target physiological sounds. This can, in turn, allow a noise attenuator device to more accurately or fully reduce the strength of the acoustic noise component from the output of the physiological signal acoustic sensing element 1120.

The acoustic decoupler 1116 can be any device or structure, made using any material, that can effectively acoustically isolate different components. For example, the acoustic decoupler 1116 can be a device or structure that is known to effectively reflect or absorb acoustic waves. In some embodiments, the acoustic sensor 1115 also includes one or more additional acoustic decouplers. For example, an acoustic decoupler 1117 can be physically positioned between the physiological signal acoustic sensing element 1120 and any expected source of noise, thereby reducing the amount of noise picked up by the physiological signal acoustic sensing element. The acoustic sensing elements 1120, 1121 and any acoustic decouplers 1116, 1117 can be physically supported in a desired spatial relationship with respect to one another using, for example, a suitable frame.

Figure 12:
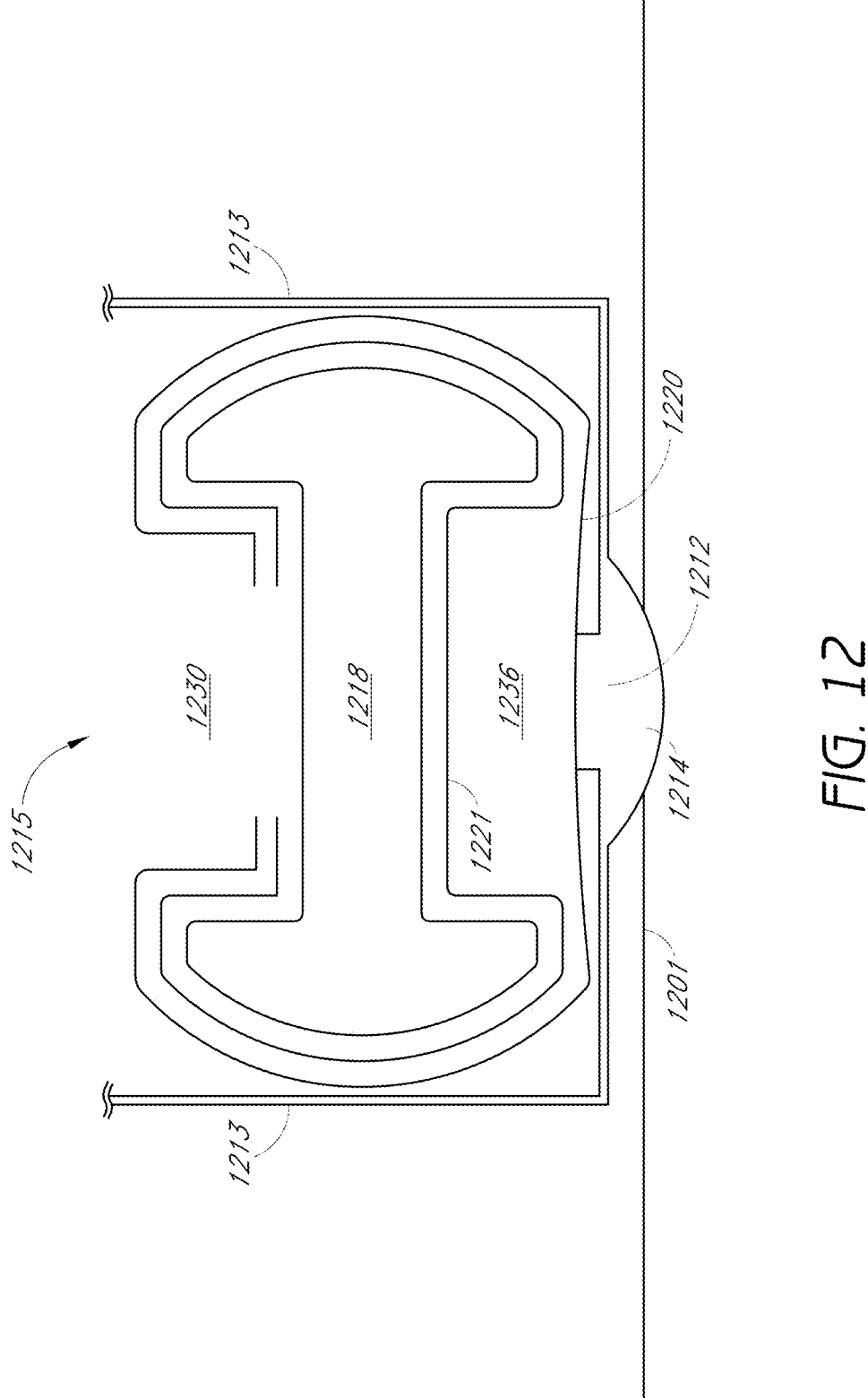
FIG. 12 is a cross-sectional schematic drawing of an embodiment of an acoustic sensor that includes a physiological signal acoustic sensing element and a noise acoustic sensing element.

FIG. 12 is a cross-sectional schematic drawing of an embodiment of an acoustic sensor 1215 that includes a physiological signal acoustic sensing element 1220 and a noise acoustic sensing element 1221. A frame 1218 supports the two acoustic sensing elements 1220, 1221. In some embodiments, the frame 1218 is similar to the frame 218 described herein. For example, the frame 1218 can provide an upper cavity 1230 and a lower cavity 1236. The lower cavity 1236 can be used to form an acoustic cavity for an acoustic sensing element, while the upper cavity 1230 can be used to house printed circuit boards and electrical components.

As discussed herein, in some embodiments, the two acoustic sensing elements 1220, 1221 are piezoelectric films, for example, similar to those illustrated in FIGS. 3A-3C. Each of the piezoelectric films can include electrical poles across which a voltage is induced by acoustic waves in the piezoelectric films, as described herein. In the illustrated embodiment, the physiological signal acoustic sensing element 1220 is a piezoelectric film wrapped around a portion of the frame 1218 and extending across the lower cavity 1236 in tension. Thus, the lower cavity 1236 serves as an acoustic cavity, and the piezoelectric film 1220 stretched in tension across the acoustic cavity 1236 is free to respond to acoustic waves incident upon it.

In some embodiments, the noise acoustic sensing element 1221 is likewise a piezoelectric film wrapped around a portion of the frame 1218. The piezoelectric film 1221 can be bonded to the frame 1218 using, for example, an adhesive layer. In this way, the piezoelectric film 1221 can vibrate in conjunction with the frame 1218 in response to acoustic waves that are incident upon it.

The piezoelectric films 1220, 1221 are shown in FIG. 12 spaced apart for clarity and ease of illustration. It should also be understood that, in some embodiments, other layers can be present, such as any of the additional layers described above. The two piezoelectric films 1220, 1221 can be separated by one or more adhesive layers, electrical insulators, mechanical supports, acoustic decouplers, etc.

The acoustic sensor 1215 also includes an acoustic coupler 1214. In some embodiments, the acoustic coupler 1214 is similar to the acoustic coupler 214 described herein. The acoustic coupler 214 can include a lower protrusion or bump configured to press against the skin 1201 of a patient when the acoustic sensor is fastened into place on the patient. The acoustic coupler 1214 can also include a protrusion 1212 designed to abut against the physiological signal acoustic sensing element 1220 and to bias it in tension across the acoustic cavity 1236. The acoustic coupler 1214 can also include sidewalls 1213 that extend upward and enclose at least a portion of the frame 1218.

For clarity of illustration, not all of the components of the acoustic sensor 1215 are illustrated. The frame 1218, the piezoelectric film 1220, and the acoustic coupler 1214 can all include any of the features described herein or illustrated with respect to FIGS. 2A-6E. In addition, the acoustic sensor 1215 can include any of the features disclosed or illustrated with respect to the same figures, including bonding layers, electrical shielding layers, sealing layers, etc. The acoustic sensor 1215 can also include electrical components (e.g., a voltage detector circuit to detect the electrical voltages induced across the poles of each of the piezoelectric films 1220, 1221), printed circuit boards, cables, patient fasteners, and other features disclosed herein.

While FIG. 12 illustrates that the two acoustic sensing elements 1220, 1221 are layered one on top of the other, they could instead be disposed with other layouts. For example, the two acoustic sensing elements 1220, 1221 could be supported by the frame 1218 side-by-side. In addition, while both acoustic sensing elements 1220, 1221 are illustrated as being supported by a common frame 1218 inside a common housing, they could instead each be supported by a separate frame and/or have separate housings. Of course, the frame 1218 could also take many different shapes than the one illustrated.

Figure 13:
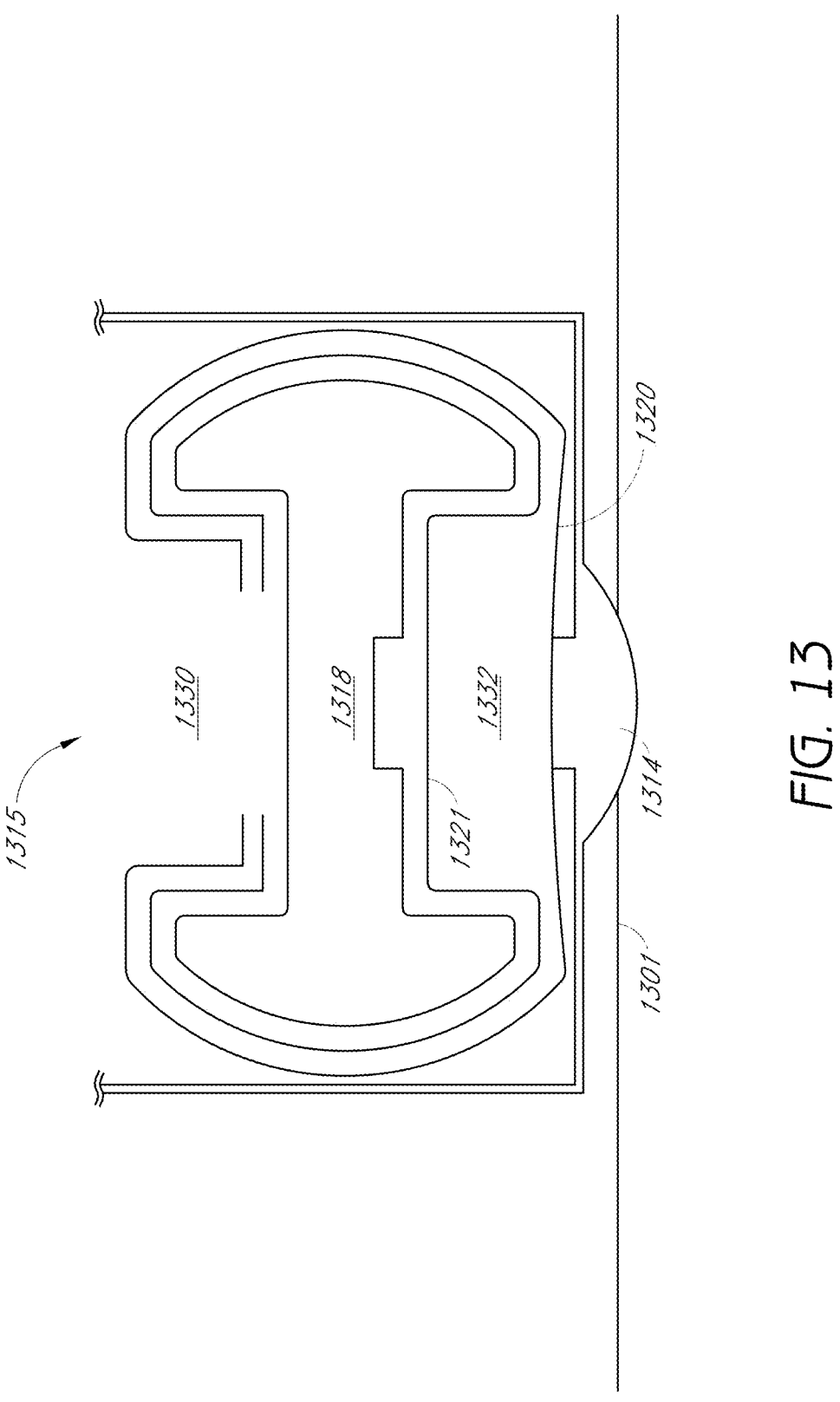
FIG. 13 is a cross-sectional schematic drawing of another embodiment of an acoustic sensor that includes a physiological signal acoustic sensing element and a noise acoustic sensing element.

FIG. 13 is a cross-sectional schematic drawing of another embodiment of an acoustic sensor 1315 that includes a physiological signal acoustic sensing element 1320 and a noise acoustic sensing element 1321. The acoustic sensing elements 1320, 1321 and the acoustic coupler 1314 are as already described with respect to FIG. 12. The frame 1318, however, includes another cavity 1332 in addition to the upper cavity 1330 and the lower cavity 1336. As illustrated, the noise acoustic sensing element 1321, a piezoelectric film, stretches across the cavity 1332 in tension to form an acoustic cavity for the noise acoustic sensing element. The presence of the acoustic cavity 1332 allows the noise acoustic sensing element 1321 greater freedom to vibrate in response to acoustic waves that are incident upon it.

As illustrated in FIG. 13, the acoustic cavity 1332 for the noise acoustic sensing element 1321 can be provided as a depression inside the floor of the acoustic cavity 1336 for the physiological signal acoustic sensing element 1320. The acoustic cavity 1332 could also be formed in one or both of the sidewalls of the acoustic cavity 1336. Alternatively, the acoustic cavity 1332 could be formed in some other portion of the frame 1318 independent of the acoustic cavity 1336 for the physiological signal acoustic sensing element 1320. In some embodiments, all or a portion of the upper cavity 1330 provided by the frame 1318 can serve as an acoustic cavity for the noise acoustic sensing element 1321. For example, the noise acoustic sensing element 1321 could stretch across the upper cavity 1330 in tension. Many other multiple-acoustic-cavity layouts are also possible.

FIG. 14 is a cross-sectional schematic drawing of another embodiment of an acoustic sensor 1415 that includes a physiological signal acoustic sensing element 1420 and a noise acoustic sensing element 1421. Once again, in this embodiment, the physiological signal acoustic sensing element is a piezoelectric film 1420. An acoustic coupler 1414 acoustically couples the piezoelectric film 1420 to the patient's body 1401. The noise acoustic sensing element 1421 is likewise a piezoelectric film. However, the position of the noise acoustic sensing element 1421 differs from that of the embodiment illustrated in, for example, FIG. 13 in that the piezoelectric film 1421 shares the acoustic cavity 1436. In the embodiment of FIG. 14, the two piezoelectric films 1420, 1421 both extend over the acoustic cavity 1436 adjacent to one another. This is shown in the bottom view 1450 of the two piezoelectric films 1420, 1421. Other physical layouts where the two acoustic sensing elements share a common acoustic cavity are also possible.

While in the embodiment of FIG. 14 the two acoustic sensing elements 1420, 1421 both extend over the acoustic cavity 1436, in some embodiments, the acoustic coupler 1414 only acoustically couples the physiological signal acoustic sensing element 1420 two the patient's skin 1401, not the noise acoustic sensing element 1421. For example, the acoustic coupler 1414 can only be in physical contact with the physiological signal acoustic sensing element 1420 without substantially contacting the noise acoustic sensing element 1421. In cases where the acoustic coupler 1414 is a bump such as the one described herein, the bump can only be aligned with the physiological signal acoustic sensing element 1420, as indicated by the dashed circle 1414 in the bottom view 1450 of the acoustic sensing elements 1420, 1421.

Figure 15:
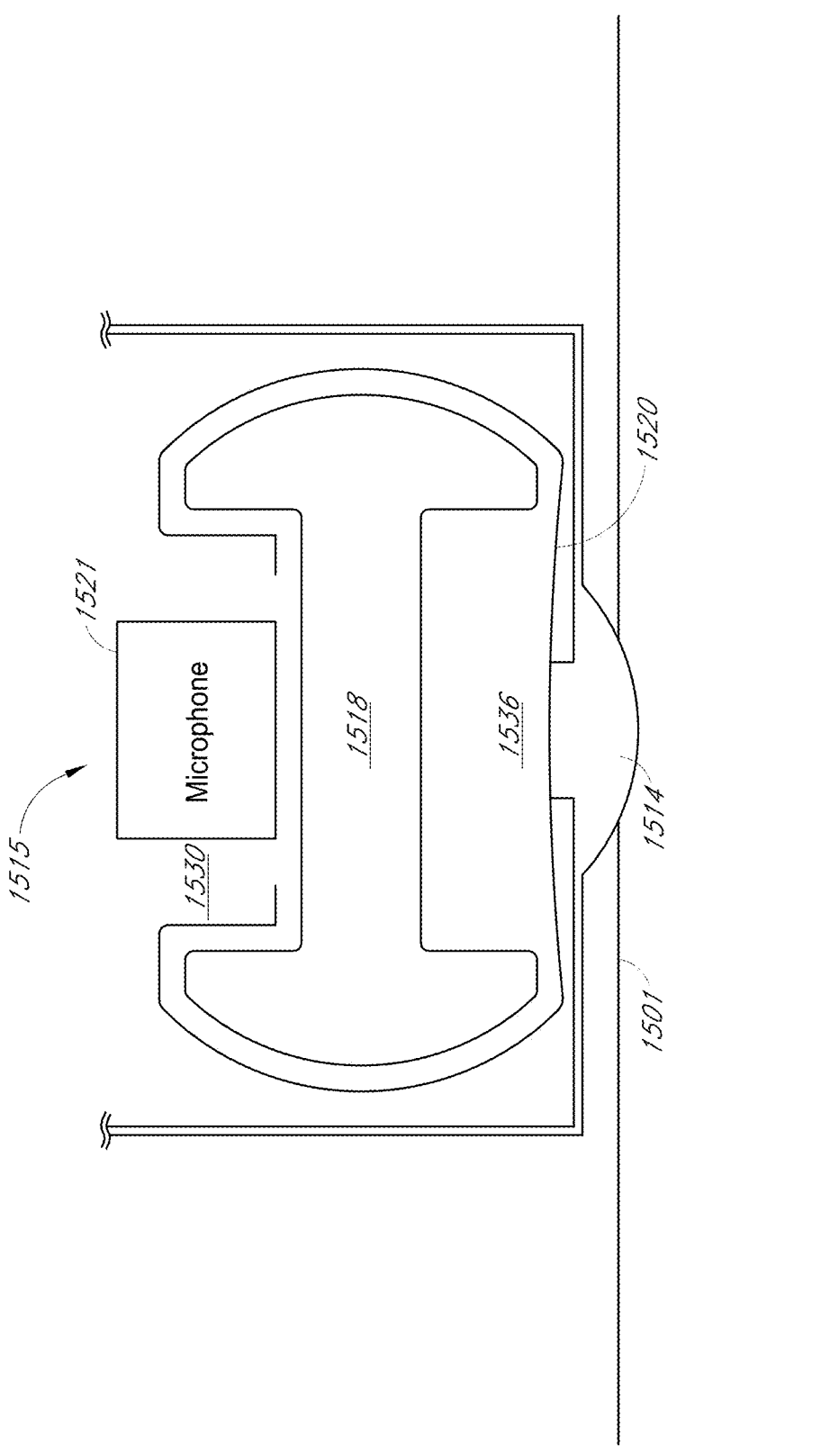
FIG. 15 is a cross-sectional schematic drawing of an embodiment of an acoustic sensor that includes a piezoelectric physiological signal acoustic sensing element and a separate noise microphone.

FIG. 15 is a cross-sectional schematic drawing of an embodiment of an acoustic sensor 1515 that includes a piezoelectric physiological signal acoustic sensing element 1520 and a separate noise microphone 1521. The frame 1518, the piezoelectric film 1520, and the acoustic coupler 1514 are as described and illustrated with respect to, for example, FIG. 13. However, the acoustic sensor 1515 does not include a second piezoelectric film to serve as the noise acoustic sensing element but instead includes a separate microphone 1521. The noise microphone 1521 can be housed, for example, in the upper cavity 1530 of the frame 1518. Other locations can also be suitable. The noise microphone 1521 can be, for example, a condenser microphone, a MEMS microphone, or an electromagnetic induction microphone, a light-modulation microphone, or a piezoelectric microphone. The noise microphone 1521 can exhibit directionality such that it is more sensitive, for example, in the upward direction away from the patient's skin 1501 in order to reduce its sensitivity to the physiological sounds picked up by the physiological signal acoustic sensing element 1520.

Figure 16:
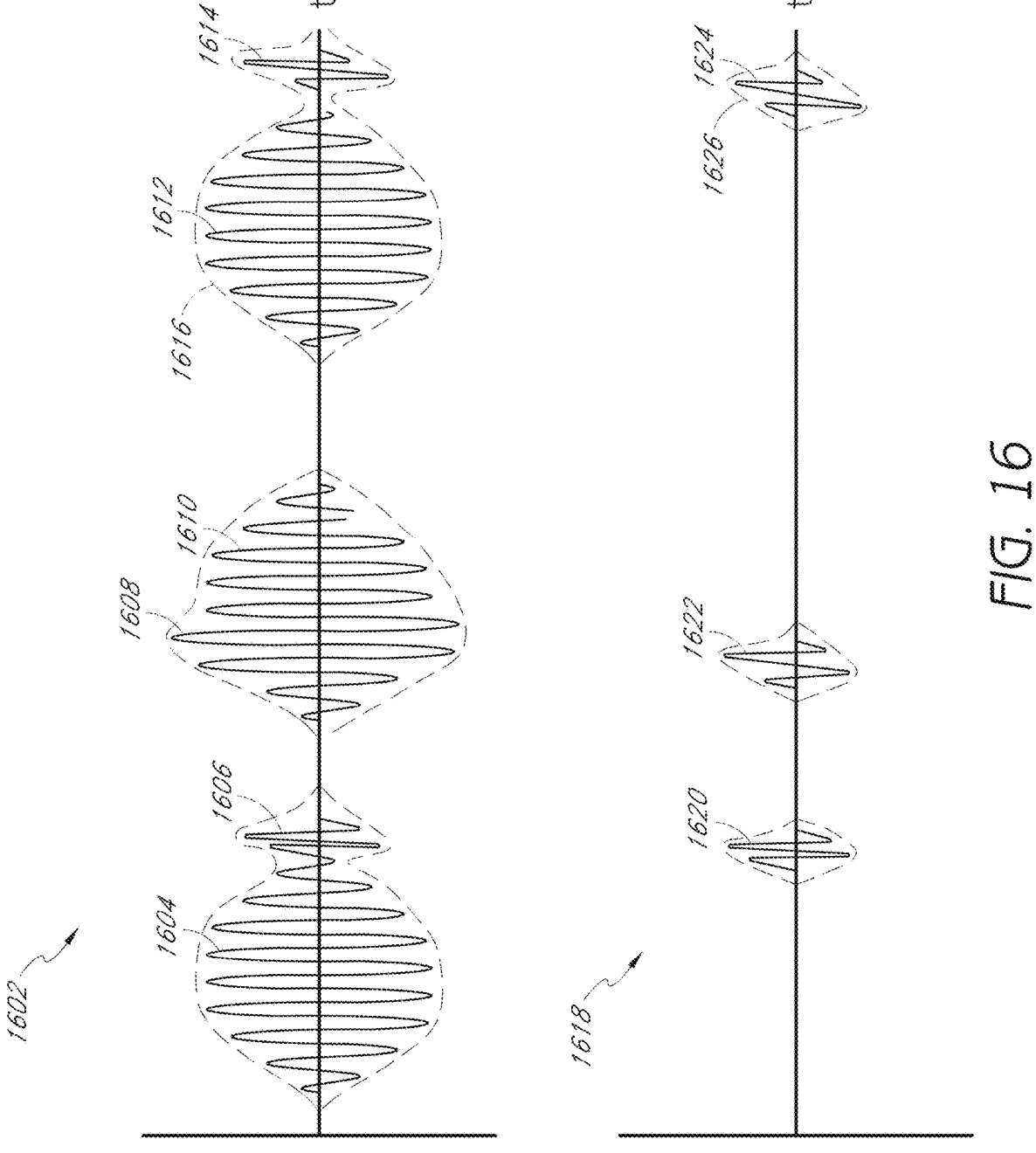
FIG. 16 illustrates a time plot of an acoustic physiological signal corrupted by noise, as well as a time plot of the noise.

FIG. 16 illustrates a time plot 1602 of an acoustic physiological signal corrupted by noise, as well as a time plot 1618 of the noise. The plot 1602 of the acoustic physiological signal corrupted with noise is a simplified representation of a patient breathing. Each of the pulses 1604, 1610, 1612 represents either an inhalation or exhalation. Three bursts of noise 1606, 1608, 1614 are superimposed on the physiological signal. The plot 1602 represents an output from a physiological signal acoustic sensing element (e.g., 1020, 1220, 1320, 1420, 1520), as described herein. The breathing sounds are acoustically coupled to the physiological signal acoustic sensing element via an acoustic coupler, as described herein. However, the physiological signal acoustic sensing element also picks up noise from the patient's surroundings.

The plot 1618 is a simplified representation of noise detected by an noise acoustic sensing element (e.g., 1021, 1221, 1321, 1421, 1521), as described herein. In particular, there are three bursts 1620, 1622, 1624 of noise. In some embodiments, it is advantageous that the bursts of noise 1620, 1622, 1624 in the plot 1618 share certain characteristics, and/or that they be meaningfully correlated with, the bursts of noise 1606, 1608, 1614 in the physiological signal. Generally, this will be dependent upon the positioning and design of both the physiological signal acoustic sensing element and the noise acoustic sensing element. For example, the amplitude of the corresponding noise bursts in the respective plots 1602, 1618 can be related by a scalar factor, a time shift, a phase shift, or in some other way depending upon, for example, the relative placement of the two acoustic sensing elements. The output of the noise acoustic sensing element can also contain a signal component representative of the physiological sounds from the patient, though, in some embodiments, this signal component is weaker in the output from the acoustic sensing element than it is in the physiological signal acoustic sensing element, as a result of the acoustic coupler.

Figure 17:
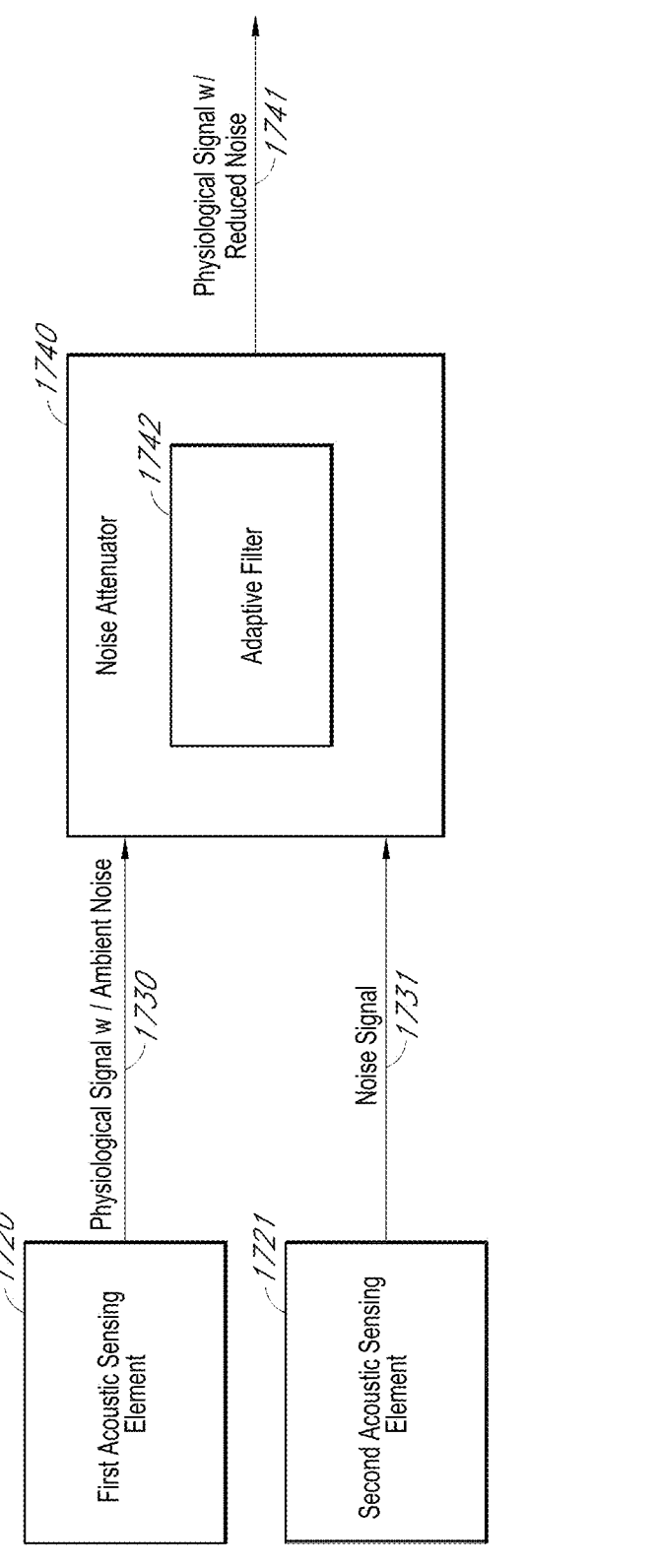
FIG. 17 is a block diagram an embodiment of a noise attenuator of an acoustic physiological monitoring system.

FIG. 17 is a block diagram an embodiment of a noise attenuator 1740 of an acoustic physiological monitoring system. As described herein, the noise attenuator 1740 can be communicatively coupled with first and second acoustic sensing elements 1720, 1721. In some embodiments, the output of the first acoustic sensing element 1720 is a physiological signal with noise 1730, as illustrated in plot 1602 in FIG. 16. In some embodiments, the output of the second acoustic sensing element 1721 is a noise reference signal 1731, as illustrated in plot 1618 in FIG. 16. Each of these signals 1730, 1731 is input to the noise attenuator 1740. The noise attenuator 1740 then reduces or removes the noise component from the physiological signal 1730 based on information regarding the noise component that is gleaned from the noise reference signal 1731.

The noise attenuator 1740 can use any of numerous methods and components for reducing, removing, filtering, canceling, subtracting, or separating out noise in a signal based on a noise reference signal, or combinations of the same or the like. For example, the noise attenuator 1740 may be an adaptive noise filter or an adaptive noise canceler. The noise attenuator 1740 can perform time domain and/or frequency domain operations. In some embodiments, the noise attenuator 1740 employs spectral subtraction methods such as power-based, magnitude-based, or non-linear spectral subtraction techniques. The noise attenuator 1740 can include time shift modules, phase shift modules, scalar and/or complex multiplier modules, filter modules, etc., each of which can be implemented using, for example, hardware (e.g., electrical components, FPGAs, ASICs, general-purpose digital signal processors, etc.) or a combination of hardware and software.

In some embodiments, the noise attenuator 1740 includes a self-adjusting component whose effect on the physiological signal corrupted by noise 1730 continuously varies in response to information derived from the noise reference signal 1731. For example, the self-adjusting component can be an adaptive filter 1742 whose transfer function, or some other characteristic, is iteratively updated based on analysis of the noise reference signal 1731. The adaptive filter 1742 can be implemented, for example, using a digital signal processor with iteratively updated filter coefficients. Other methods of implementing the adaptive filter 1742 can also be used. Filter coefficients can be updated using, for example, a least mean squares algorithm (LMS), or a least squares algorithm, a recursive least squares algorithm (RLS). The noise attenuator 1740 can also use, for example, a Kalman filter, a joint process estimator, an adaptive joint process estimator, a least-squares lattice joint process estimator, a least-squares lattice predictor, a noise canceler, a correlation canceler, optimized time or frequency domain implementations of any of the above, combinations of the same, and the like.

Figure 18:
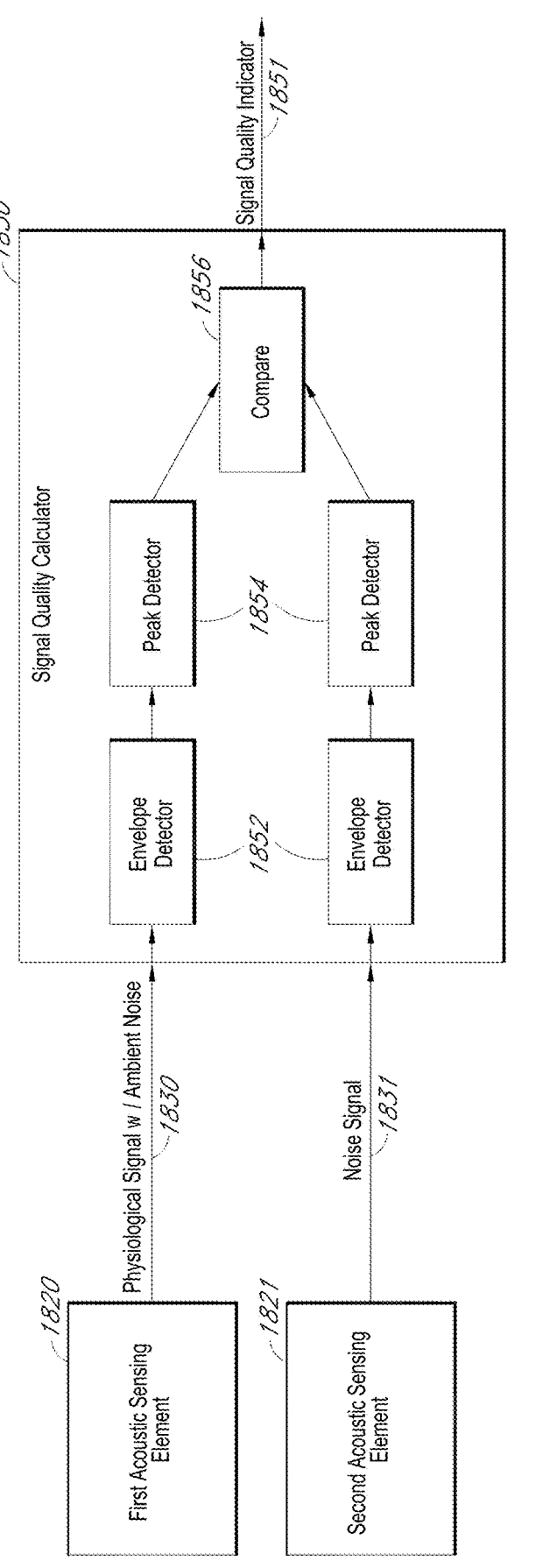
FIG. 18 is a block diagram of an embodiment of a signal quality calculator in an acoustic physiological monitoring system.

FIG. 18 is a block diagram of an embodiment of a signal quality calculator 1850 in an acoustic physiological monitoring system. The signal quality calculator 1850 is communicatively coupled with first and second acoustic sensing elements 1820, 1821. In some embodiments, one input to the signal quality calculator 1850 is a physiological signal corrupted by noise 1830 (e.g., as illustrated in plot 1602 in FIG. 16), while the other input is an noise reference signal 1831 (e.g., as illustrated in plot 1618 in FIG. 16). Based, at least in part, on these input signals, the signal quality calculator 1850 outputs an objective signal quality indicator 1851.

As described herein, the signal quality calculator 1850 is a device that is used to determine, for example, an objective indicator of the quality of the physiological information obtained from one or more acoustic sensing elements. This can be done, for example, by comparing the physiological signal 1830 with the noise signal 1831. The signal quality calculator 1850 can also output an objective indicator of the degree of confidence in the accuracy of a physiological characteristic (e.g., respiratory rate) determined based on the physiological information collected from one or more acoustic sensors.

In some embodiments, the signal quality calculator 1850 includes one or more signal envelope detectors 1852, one or more peak detectors 1854, and a comparator 1856. The envelope detectors 1852 are used, for example, to detect the respective amplitude envelopes 1616, 1626 of the physiological signal 1830 and the noise reference signal 1831, as illustrated in FIG. 16. The envelope detectors 1852 can be implemented in any way known in the art. For example, the envelope detectors 1852 can use squaring and low-pass filtering techniques and/or Hilbert transform techniques for envelope detection. Other techniques or devices can also be used for envelope detection, including analog devices.

Once the amplitude envelopes of the physiological signal 1830 and the noise reference signal 1831 have been identified, peak detectors 1854 can be used to identify different peaks in the amplitude envelopes, the temporal spacing between peaks, the relative maximum amplitude of the peaks, the time width of the peaks, etc. For example, with reference to plot 1618, the peak detector 1854 can identify three separate peaks, one for each illustrated bursts of acoustic noise. With reference to plot 1602, the peak detector 1854 can identify five separate peaks: one corresponding to the first pulse 1604 of breathing sounds, one corresponding to the first burst of acoustic noise 1606, a larger amplitude peak corresponding to the second pulse of breathing sounds with superimposed noise 1610, 1608, one corresponding to the third pulse of breathing sounds 1612, and one corresponding to the third burst of acoustic noise 1614.

Once the peaks of the amplitude envelopes have been detected, possibly along with information regarding the temporal spacing between the peaks, the relative heights of the peaks, their widths etc., this information can then be transmitted to the comparator 1856. In some embodiments, the comparator 1856 is endowed with logic for determining an objective signal quality indicator based, at least in part, on the information from the peak detectors 1854.

In some embodiments, the comparator 1856 can determine whether each of the identified peaks in the amplitude envelope of the physiological signal 1830 has a corresponding peak in the amplitude envelope of the noise signal 1831. For example, with respect to the plots 1602, 1618 in FIG. 16, the comparator 1856 can determine that the first peak in the physiological signal 1830 (the first pulse of breathing sounds 1604) does not have a corresponding peak in the noise signal 1831 at the same time. On this basis, the comparator 1856 could judge that the first peak 1604 can well likely represent physiological information. Upon analyzing the second peak in the physiological signal 1830 (the first burst of noise 1606), the comparator 1856 could note the presence of a corresponding peak 1620 in the noise reference signal 1831 at the same time and having approximately the same height and width. On this basis, the comparator 1856 could judge that the second peak in the physiological signal 1830 can well likely represent acoustic noise.

An analysis of the third peak in the physiological signal 1830 (the second pulse of breathing sounds 1610) can identify a corresponding peak 1622 in the noise reference signal 1831 at the same time but having a smaller width and height than the peak 1610 in the physiological signal. On this basis, the comparator 1856 can determine that it is somewhat likely that the third peak 1610 in the physiological signal 1830 is representative of physiological information. In this way, the signal quality calculator 1850 can identify, for example, individual features of the time domain physiological signal 1830 and noise reference signal 1831, and then determine the likelihood that each feature represents physiological information or noise information.

The signal quality calculator 1850 can then calculate and output an indicator (e.g., a probability value, a percentage, an occurrence indicator, a Boolean or binary value, an alarm or alert, or some other indicator) to express the extent to which the physiological signal 1830 is viewed as being indicative of actual physiological information rather than noise. The signal quality calculator 1850 can also output an indicator to express the confidence in a physiological characteristic calculated from the physiological signal 1830. For example, if the signal quality calculator 1850 determines that the physiological signal 1830 is primarily composed of physiological information, then it can determine a high confidence level in a physiological characteristic (e.g., respiratory rate) determined from the physiological signal 1830. In some embodiments, the physiological signal with reduced noise (e.g., 1741) from the noise attenuator can also serve as an input to the signal quality calculator 1850.

While a time domain method for determining signal quality is illustrated in FIG. 18, signal quality calculations could also be performed in the frequency domain. Also, different signal quality calculation algorithms can be used depending upon the particular type of physiological information being sensed, and the characteristics of the signals that are representative of that physiological information.

Electromagnetic Interference (EMI) Compensation

In some embodiments, the physiological monitoring systems and patient sensors described herein include electromagnetic interference compensation features. The electromagnetic interference compensation features can be useful for reducing any deleterious effect of EMI on the accuracy of physiological characteristics determined using the monitoring systems. One possible source of such EMI could be, for example, 50-60 Hz RF waves generated by the electric power distribution system in a patient care facility.

In some embodiments, the physiological monitoring systems include an electrical conductor for detecting an EMI reference signal that is indicative of EMI that may have corrupted electrical signals used by the physiological monitoring systems (e.g., a physiological signal generated by an acoustic sensing element). The EMI reference signal detector can be, for example, a dedicated antenna that is positioned at a location where the EMI that it detects is in some way representative of, or meaningfully correlated with, the EMI to which an electrical signal within the patient sensor is exposed. The EMI reference signal detector can be located, for example, on or in one or more wearable patient sensors (e.g., 215, 815, 915, etc.), though it may also be located in a separate physiological monitor unit, intermediate location (e.g., cable, connector or hub), at any location described above with respect to acoustic noise reference sensing elements, or at some other location.

In some embodiments, the EMI reference signal detector is a conductive plate or wire, or some other conductive structure. In some embodiments, the EMI reference signal detector is left electrically floating. While in some embodiments, the EMI reference signal detector is a dedicated component, in other embodiments other existing components of, for example, a patient sensor described herein can be used as the EMI reference signal detector. For example, one or more electrical shielding layers (e.g., 226, 228) in a patient sensor can be used to detect EMI and to generate an EMI reference signal. Generally, according to certain aspects, any of the shielding barriers described herein (e.g., with respect to FIGS. 2B-E, 5A-B, 21-22, etc.) can be used to detect EMI and generate an EMI reference signal.

In some embodiments, the EMI reference signal generated by the EMI reference signal detector is transmitted to a noise attenuator or other sensing circuitry. The noise attenuator can also be communicatively coupled to, for example, one or more physiological electrical signals output from the acoustic sensing elements described herein. Such physiological electrical signals can be corrupted by any EMI to which they are exposed.

The noise attenuator or other sensing circuitry reduces or removes the EMI component from the physiological signal based on information regarding the EMI that is gleaned from the EMI reference signal. The noise attenuator or other sensing circuitry can use any of numerous methods and components for reducing, removing, filtering, canceling, subtracting, or separating out EMI in a signal based on the EMI reference signal, or combinations of the same or the like. For example, the noise attenuator may be an adaptive noise filter or an adaptive noise canceler. The noise attenuator can perform time domain and/or frequency domain operations. The noise attenuator can include time shift modules, phase shift modules, scalar and/or complex multiplier modules, filter modules, etc., each of which can be implemented using, for example, hardware (e.g., electrical components, FPGAs, ASICS, general-purpose digital signal processors, etc.) or a combination of hardware and software.

In some embodiments, the noise attenuator or other sensing circuitry includes a self-adjusting component whose effect on the physiological signal corrupted by EMI continuously varies in response to information derived from the EMI reference signal. For example, the self-adjusting component can be an adaptive filter whose transfer function, or some other characteristic, is iteratively updated based on analysis of the EMI reference signal. The adaptive filter can be implemented, for example, using a digital signal processor with iteratively updated filter coefficients. Other methods of implementing the adaptive filter can also be used. Filter coefficients can be updated using, for example, a least mean squares algorithm (LMS), or a least squares algorithm, a recursive least squares algorithm (RLS). The noise attenuator can also use, for example, a Kalman filter, a joint process estimator, an adaptive joint process estimator, a least-squares lattice joint process estimator, a least-squares lattice predictor, a noise canceler, a correlation canceler, optimized time or frequency domain implementations of any of the above, combinations of the same, and the like.

Additional Sensor Embodiments

Figure 19A:
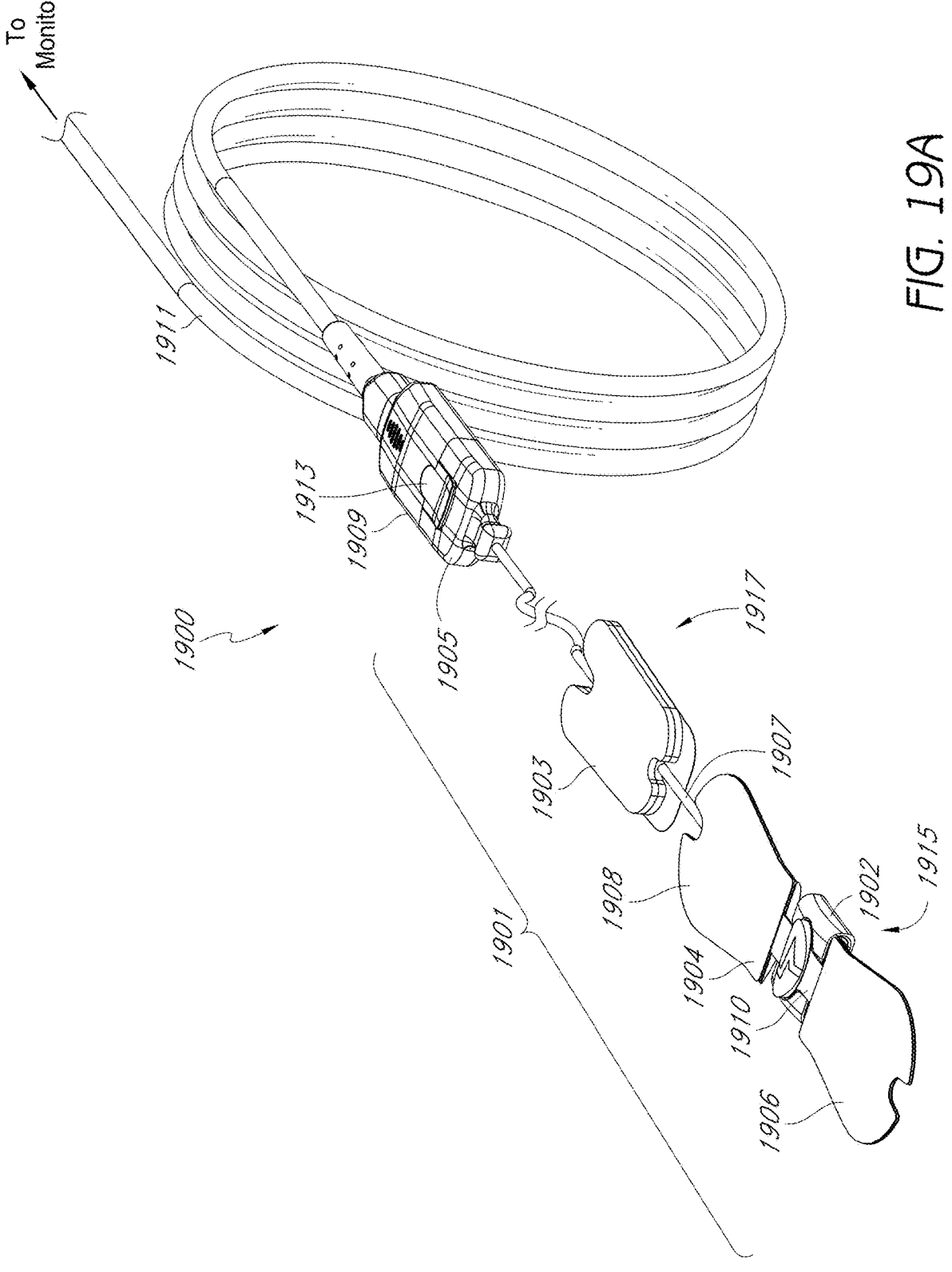
FIG. 19A is a top perspective view illustrating portions of a sensor assembly in accordance with an embodiment of the disclosure.

FIG. 19A is a top perspective of a sensor system 1900 including a sensor assembly 1901 suitable for use with any of the physiological monitors shown in FIGS. 1A-C and a monitor cable 1911. The sensor assembly 1901 includes a sensor 1915, a cable assembly 1917 and a connector 1905. The sensor 1915, in one embodiment, includes a sensor subassembly 1902 and an attachment subassembly 1904. The cable assembly 1917 of one embodiment includes a cable 1907 and a patient anchor 1903. The various components are connected to one another via the sensor cable 1907. The sensor connector subassembly 1905 can be removably attached to monitor connector 1909 which is connected to physiological monitor (not shown) through the monitor cable 1911. In one embodiment, the sensor assembly 1901 communicates with the physiological monitor wirelessly. In various embodiments, not all of the components illustrated in FIG. 19A are included in the sensor system 1900. For example, in various embodiments, one or more of the patient anchor 1903 and the attachment subassembly 1904 are not included. In one embodiment, for example, a bandage or tape is used instead of the attachment subassembly 1904 to attach the sensor subassembly 1902 to the measurement site. Moreover, such bandages or tapes may be a variety of different shapes including generally elongate, circular and oval, for example.

The sensor connector subassembly 1905 and monitor connector 1909 may be advantageously configured to allow the sensor connector 1905 to be straightforwardly and efficiently joined with and detached from the monitor connector 1909. Embodiments of sensor and monitor connectors having similar connection mechanisms are described in U.S. patent application Ser. No. 12/248,856 (hereinafter referred to as "the '856 application"), filed on Oct. 9, 2008, which is incorporated in its entirety by reference herein. For example, the sensor connector 1905 includes a mating feature 1913 which mates with a corresponding feature (not shown) on the monitor connector 1909. The mating feature 1905 may include a protrusion which engages in a snap fit with a recess on the monitor connector 1909. In certain embodiments, the sensor connector 1905 can be detached via one hand operation, for example. Examples of connection mechanisms may be found specifically in paragraphs [0042], [0050], [0051], [0061]-[0068] and [0079], and with respect to FIGS. 8A-F, 13A-E, 19A-F, 23A-D and 24A-C of the '856 application, for example. The sensor system 1900 measures one or more physiological parameters of the patient, such as one of the physiological parameters described above.

The sensor connector subassembly 1905 and monitor connector 1909 may advantageously reduce the amount of unshielded area in and generally provide enhanced shielding of the electrical connection between the sensor and monitor in certain embodiments. Examples of such shielding mechanisms are disclosed in the '856 application in paragraphs [0043]-[0053], and with respect to FIGS. 9A-C, 11A-E, 13A-E, 14A-B, 15A-C, and 16A-E, for example.

As will be described in greater detail herein, in an embodiment, the acoustic sensor assembly 1901 includes a sensing element, such as, for example, a piezoelectric device or other acoustic sensing device. The sensing element generates a voltage that is responsive to vibrations generated by the patient, and the sensor includes circuitry to transmit the voltage generated by the sensing element to a processor for processing. In an embodiment, the acoustic sensor assembly 1901 includes circuitry for detecting and transmitting information related to biological sounds to a physiological monitor. These biological sounds may include heart, breathing, and/or digestive system sounds, in addition to many other physiological phenomena. The acoustic sensor 1915 in certain embodiments is a biological sound sensor, such as the sensors described herein. In some embodiments, the biological sound sensor is one of the sensors such as those described in the '883 application. In other embodiments, the acoustic sensor 1915 is a biological sound sensor such as those described in U.S. Pat. No. 6,661,161, which is incorporated by reference herein. Other embodiments include other suitable acoustic sensors.

The attachment sub-assembly 1904 includes first and second elongate portions 1906, 1908. The first and second elongate portions 1906, 1908 can include patient adhesive (e.g., in some embodiments, tape, glue, a suction device, etc.) attached to a elongate member 1910. The adhesive on the elongate portions 1906, 1908 can be used to secure the sensor subassembly 1902 to a patient's skin. As will be discussed in greater detail herein, the elongate member 1910 can beneficially bias the sensor subassembly 1902 in tension against the patient's skin and reduce stress on the connection between the patient adhesive and the skin. A removable backing can be provided with the patient adhesive to protect the adhesive surface prior to affixing to a patient's skin.

The sensor cable 1907 is electrically coupled to the sensor subassembly 1902 via a printed circuit board ("PCB") (not shown) in the sensor subassembly 1902. Through this contact, electrical signals are communicated from the multiparameter sensor subassembly to the physiological monitor through the sensor cable 1907 and the cable 1911.

Figure 19B:
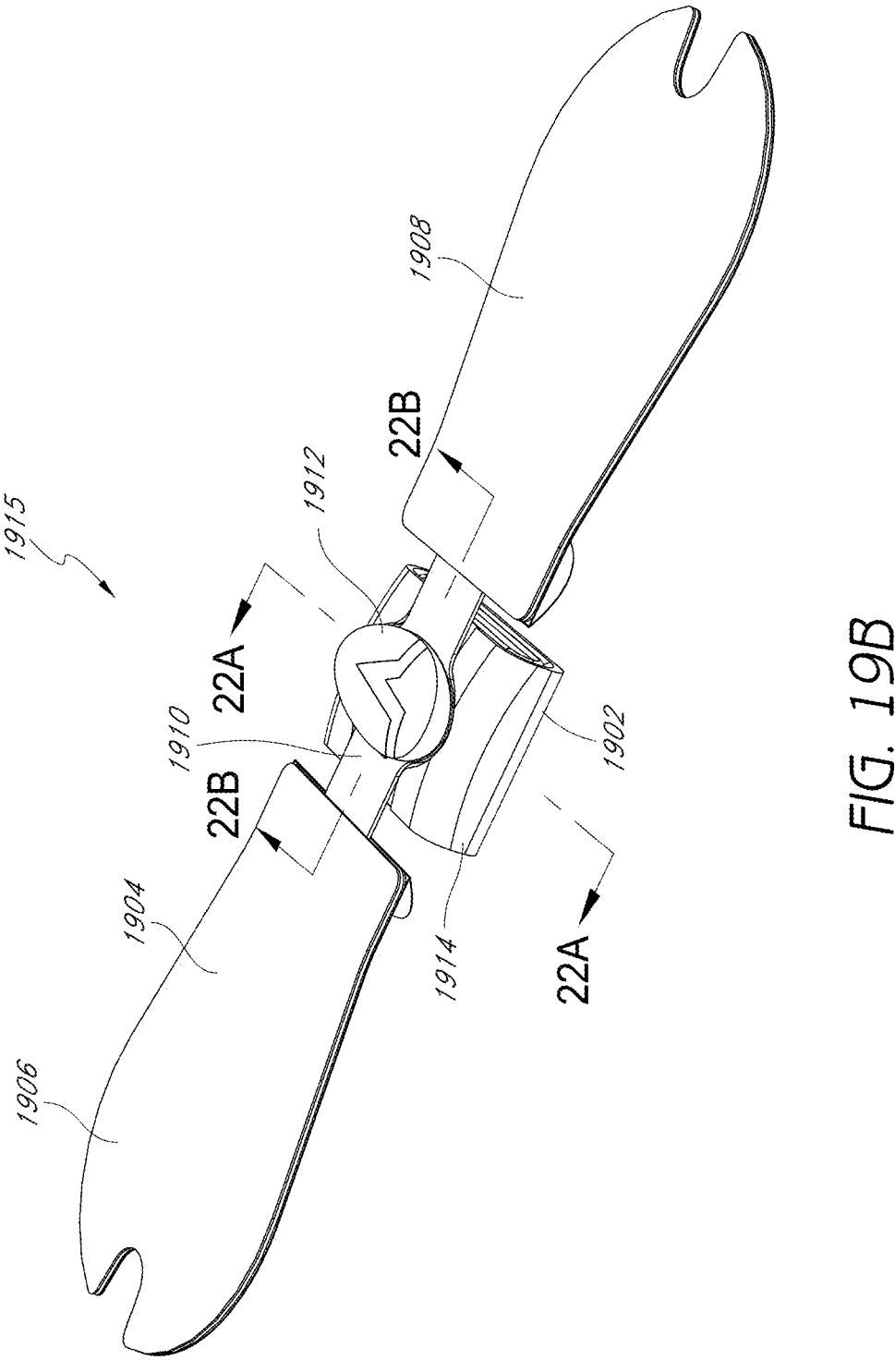
FIGS. 19B-19C are top and bottom perspective views, respectively, of a sensor including a sensor subassembly and an attachment subassembly of FIG. 19A.
Figure 19C:
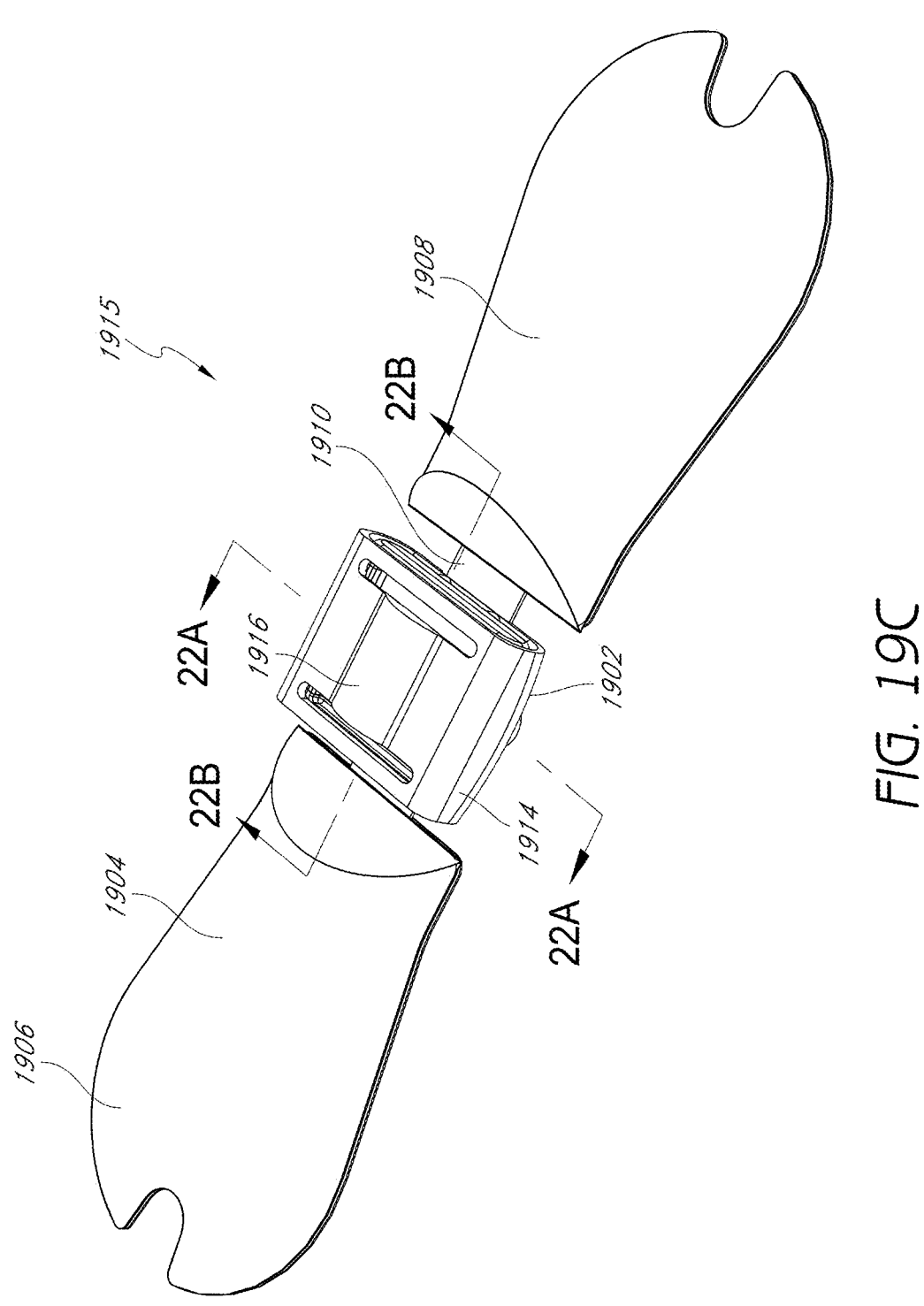

FIGS. 19B-19C are top and bottom perspective views of a sensor including subassembly 1902 and an attachment subassembly 1904 in accordance with an embodiment of the present disclosure. The attachment subassembly 1904 generally includes lateral extensions symmetrically placed about the sensor subassembly 1902. For example, the attachment subassembly 1904 can include single, dual or multiple wing-like extensions or arms that extend from the sensor subassembly 1902. In other embodiments, the attachment subassembly 1902 has a circular or rounded shape, which advantageously allows uniform adhesion of the attachment subassembly 1904 to an acoustic measurement site. The attachment subassembly 1904 can include plastic, metal or any resilient material, including a spring or other material biased to retain its shape when bent. In the illustrated embodiment, the attachment subassembly 1904 includes a first elongate portion 1906, a second elongate portion 1908, an elongate member 1910 and a button 1912. As will be discussed, in certain embodiments the attachment subassembly 1904 or portions thereof are disposable and/or removably attachable from the sensor subassembly 1902. The button 1910 mechanically couples the attachment subassembly 1904 to the sensor subassembly 1902. The attachment subassembly 1904 is described in greater detail below with respect to FIGS. 9A-9D. The attachment subassembly 1904 may also be referred to as an attachment element herein.

In one embodiment, the sensor subassembly 1902 is configured to be attached to a patient and includes a sensing element configured to detect bodily sounds from a patient measurement site. The sensing element may include a piezoelectric membrane, for example, and is supported by a support structure such as a generally rectangular support frame 1918. The piezoelectric membrane is configured to move on the frame in response to acoustic vibrations, thereby generating electrical signals indicative of the bodily sounds of the patient. An electrical shielding barrier (not shown) may be included which conforms to the contours and movements of the piezoelectric element during use. In the illustrated embodiment, additional layers are provided to help adhere the piezoelectric membrane to the electrical shielding barrier 1927. Embodiments of the electrical shielding barrier are described below with respect to FIGS. 3A-B and FIGS. 5A-B, FIGS. 21-22, for example.

Embodiments of the sensor subassembly 1902 also include an acoustic coupler 1914, which advantageously improves the coupling between the source of the signal to be measured by the sensor (e.g., the patient's skin) and the sensing element. The acoustic coupler 1914 of one embodiment includes a bump positioned to apply pressure to the sensing element so as to bias the sensing element in tension.

The acoustic coupler 1914 can also provide electrical isolation between the patient and the electrical components of the sensor, beneficially preventing potentially harmful electrical pathways or ground loops from forming and affecting the patient or the sensor.

The sensor subassembly 1902 of the illustrated embodiment includes an acoustic coupler 1914 which generally envelops or at least partially covers some or all of the components of the sensor subassembly 1902. Referring to FIG. 19C, the bottom of the acoustic coupler 1914 includes a contact portion 1916 which is brought into contact with the skin of the patient. Embodiments of acoustic couplers are described below with respect to FIGS. 19D-19E, 4, and 5A-B, for example.

Figure 19D:
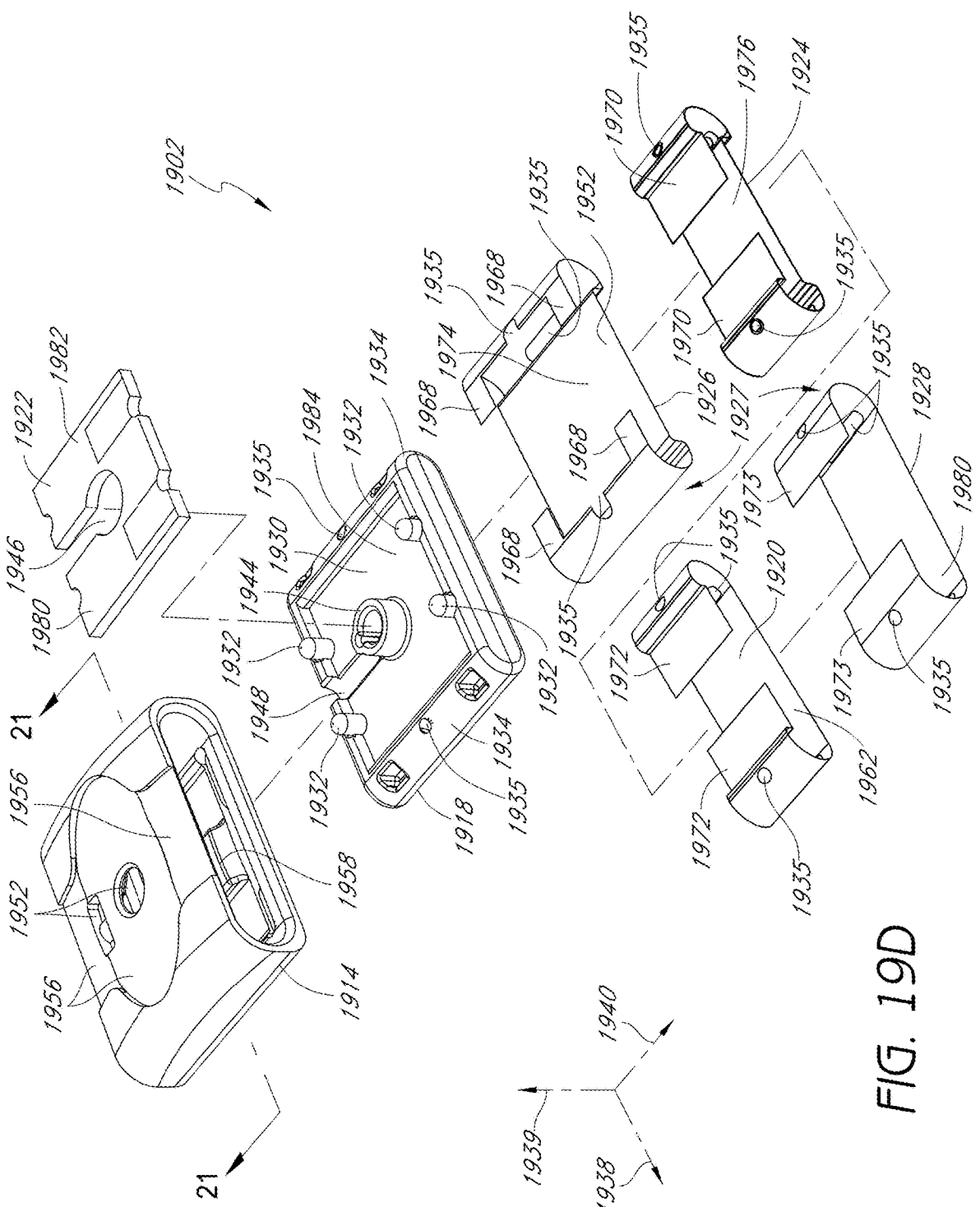
FIGS. 19D-19E are top and bottom exploded, perspective views, respectively, of the sensor subassembly of FIGS. 19A-19C.
Figure 19E:
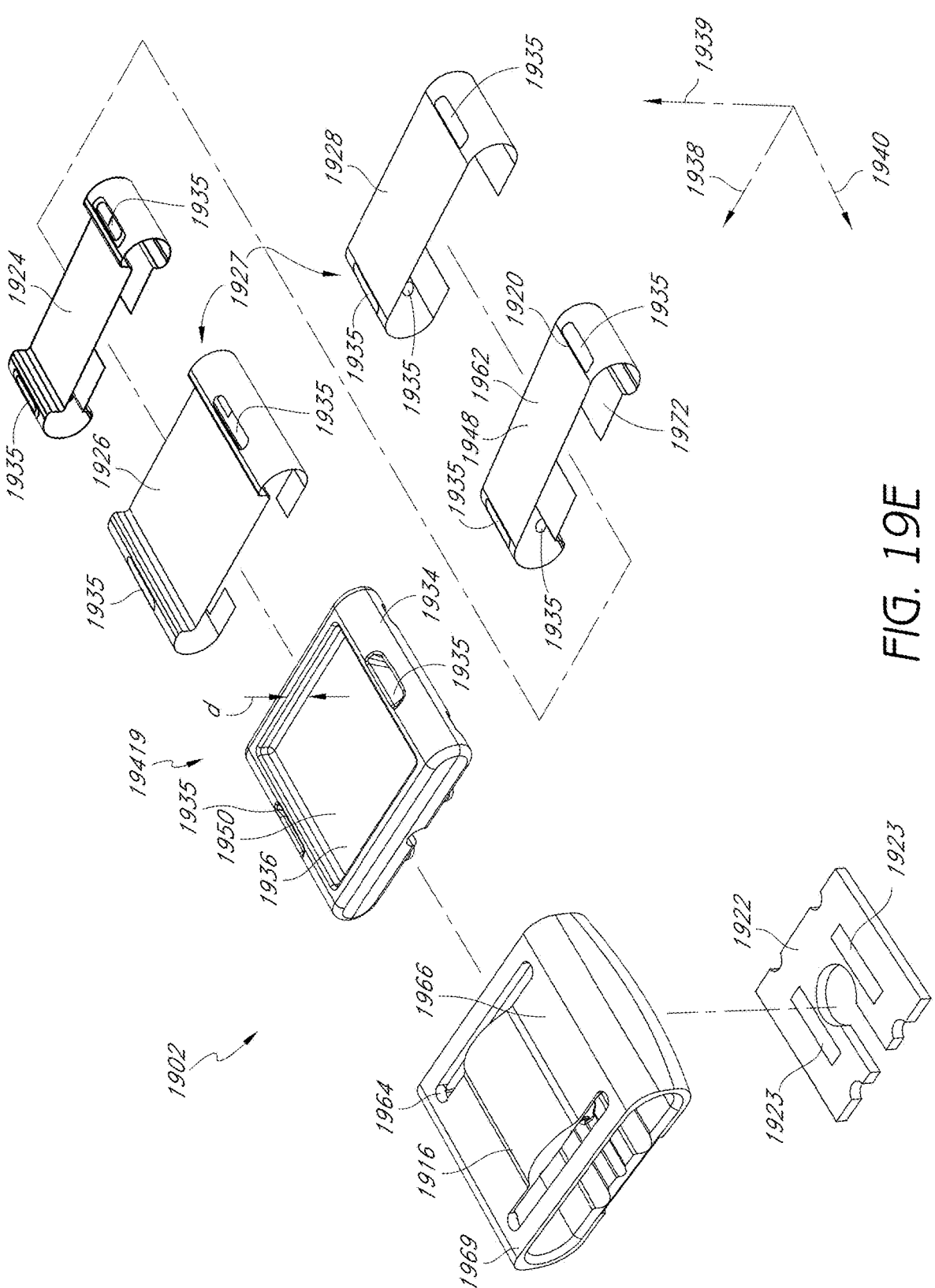

FIGS. 19D-19E are top and bottom exploded, perspective views, respectively, of the sensor subassembly 1902 of FIGS. 19A-C.

Support Frame

The frame generally supports the various components of the sensor. For example, the piezoelectric element, electrical shielding barrier, attachment element and other components may be attached to the frame. The frame can be configured to hold the various components in place with respect to the frame and with respect to one another, thereby beneficially providing continuous operation of the sensor under a variety of conditions, such as during movement of the sensor. For example, the frame can be configured to hold one or more of the components together with a predetermined force. Moreover, the frame can include one or more features which can improve the operation of the sensor. For example, the frame can include one or more cavities which allow for the piezoelectric element to move freely and/or which amplify acoustic vibrations from bodily sounds of the patient.

In the illustrated embodiment, a PCB 1922 is mounted on the frame 1918. The frame 1918 supports a series of layers which are generally wrapped around the underside 1942 of the frame 1918 and include, from innermost to outermost, an inner shield layer 1926, an bonding layer 1924, a sensing element 1920 and an outer shield layer 1928.

As shown in FIG. 19D, the support frame 1918 has a generally rectangular shape, as viewed from the top or bottom, although the frame shape could be any shape, including square, oval, elliptical, elongated, etc. In various embodiments, the frame 1918 has a length of from between about 5 and 50 millimeters. In one embodiment, the frame 1918 has a length of about 17 millimeters. The relatively small size of the frame 1918 can allow the sensor subassembly 1902 to be attached comfortably to contoured, generally curved portions of the patient's body. For, example, the sensor subassembly 1902 can be comfortably attached to portions of the patient's neck whereas a larger frame 1918 may be awkwardly situated on the patient's neck or other contoured portion of the patient. The size of the frame 1918 may allow for the sensor subassembly 1902 to be attached to the patient in a manner allowing for improved sensor operation. For example, the relatively small frame 1918, corresponding to a relatively smaller patient contact area, allows for the sensor subassembly 1902 to be applied with substantially uniform pressure across the patient contact area.

The frame 1918 is configured to hold the various components in place with respect to the frame. For example, in one embodiment, the frame 1918 includes at least one locking post 1932, which is used to lock the PCB 1922 into the sensor sub-assembly 1902, as described below. In the illustrated embodiment, the frame 1918 includes four locking posts 1932, for example, near each of the 1918 four corners of the frame 1918. In other embodiments, the frame 1918 includes one, two, or three locking posts 1918. When the locking posts 1932 are brought into contact with horns of an ultrasonic welder or a heat source, they liquefy and flow to expand over the material beneath it and then harden in the expanded state when the welder is removed. When the components of the sensor sub-assembly 1902 are in place, the locking posts 1932 are flowed to lock all components into a fixed position.

In one embodiment, the locking posts 1932 are formed from the same material as, and are integral with the frame 1918. In other embodiments, the locking posts 1932 are not formed from the same material as the frame 1918. For example, in other embodiments, the locking posts 1932 include clips, welds, adhesives, and/or other locks to hold the components of the sensor sub-assembly 1902 in place when the locking posts 1932 are locked into place.

With further reference to FIGS. 19E, in an assembled configuration, the PCB 1922 sits inside of an upper cavity 1930 of the frame 1918 and is pressed against the sensing element 1920 to create a stable electrical contact between the PCB 1922 and electrical contact portions of the sensing element 1920. For example, in certain embodiments, the expanded locking posts 1932 press downward on the PCB 1922 against the sensing element 1920, which is positioned between the PCB 1922 and the frame 1918. In this manner, a stable and sufficient contact force between the PCB 1922 and the sensing element 1920 is maintained. For example, as the sensor assembly 1900 moves due to acoustic vibrations coming from the patient or due to other movements of the patient, the electrical contact between the PCB 1922 and the sensing element 1920 remains stable, constant, uninterrupted, and/or unchanged.

In another embodiment, the sensing element 1920 may be positioned over the PCB 1922 between the expanded locking posts 1932 and the PCB 1922. In certain embodiments, the contact force between the PCB 1922 and the sensing element 1920 is from between about 0.5 pounds and about 10 pounds. In other embodiments, the contact force is between about 1 pound and about 3 pounds. In one embodiment, the contact force between the PCB 1922 and the sensing element 1920 is at least about 2 pounds. The bonding layer 1924 is positioned between the frame 1918 and the sensing element 1920 and allows, among other things, for the sensing element 1920 to be held in place with respect to the frame 1918 prior to placement of the PCB 1922. The PCB 1922 and frame 1918 include corresponding cutout portions 1946, 1948 which are configured to accept the sensor cable (not shown).

The PCB cutout portion 1946 also includes a circular portion which is configured to accept a button post 1944 positioned in the center of the cavity 1930. The button post 1944 is configured to receive the button 1912 (FIG. 19B). The frame 1918, shielding layers 1926, 1928, adhesive layer 1924, and sensing element 1920 each include injection holes 1935 extending through opposing sides of the respective components. Additionally, in an assembled configuration the injection holes 1935 of the various components line up with the holes 1935 of the other components such that a syringe or other device can be inserted through the holes. Glue is injected into the holes 1935 using the syringe, bonding the assembled components together.

Referring now to FIG. 19E, a lower cavity 1936 is disposed on the underside of the frame 1918 and has a depth d. In an assembled configuration, the sensing element 1920 is wrapped around the frame 1918 in the direction of the transverse axis 1938 such that the lower planar portion 1962 of the sensing element 1920 stretches across the top of the lower cavity 1936. As such, the lower cavity 1936 can serve as an acoustic chamber of the multi-parameter sensor assembly. The sensing element 1920 thus has freedom to move up into the acoustic chamber in response to acoustic vibrations, allowing for the mechanical deformation of the piezoelectric sensing material and generation of the corresponding electrical signal. In addition, the chamber of certain embodiments allows sound waves incident on the sensing element to reverberate in the chamber. As such, the sound waves from the patient may be amplified or more effectively directed to the sensing element 1920, thereby improving the sensitivity of the sensing element 1920. As such, the cavity 1936 allows for improved operation of the sensor.

Figure 19F:
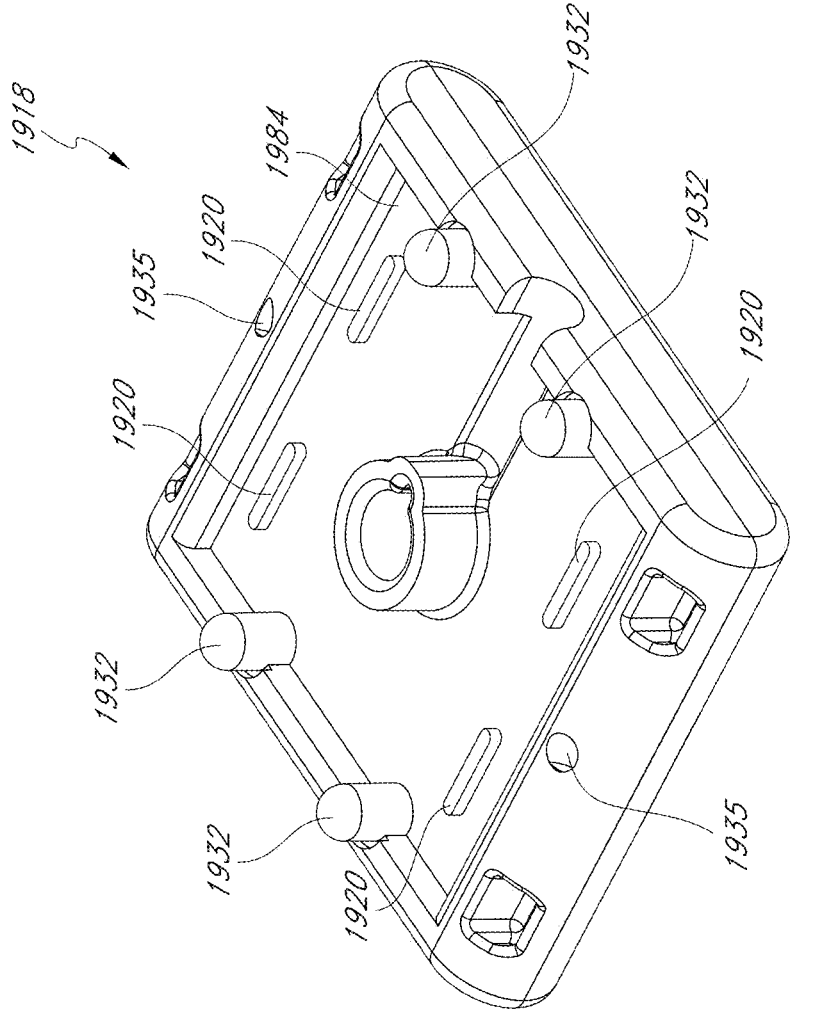
FIG. 19F shows a top perspective view of an embodiment of a support frame.

The frame may include one or more contacts extending from the frame which press into corresponding contact strips of the PCB, helping to ensure a stable, relatively constant contact resistance between the PCB and the sensing element. FIG. 19F shows a top perspective view of an embodiment of a support frame 1918 including such contacts. The frame 1918 may be generally similar in structure and include one or more of the features of the frame shown in FIGS. 19D-19E, such as the locking posts 332 and the upper surface 384. The frame 1918 further includes one or more contact bumps 1920 which press into corresponding contact strips 1923 (FIG. 2E) of the PCB 1922 when the sensor sub-assembly is assembled. For example, the contact bumps 1920 may include generally narrow rectangular raised segments and may be positioned on the upper surface 1984 of the frame 1918.

The contact bumps 1920 help ensure a stable, constant contact resistance between the PCB 1922 and the sensing element 1920. The contact bumps 1920 are dimensioned to press a portion of the sensing element 1920 into the PCB 1922 when the sensor subassembly 1902 is assembled. In some embodiments, the height of the contact bumps 1920 is from about 0.1 to about 1 mm. In some embodiments, the height of the contact bumps 1920 is in the range from about 0.2 to about 0.3 mm. In one embodiment, the contact bumps 1920 have a height of about 0.26 mm. The height is generally selected to provide adequate force and pressure between the sensing element 1920 and PCB 1922.

In other embodiments, the contact bumps may have different shapes. For example, the bumps 1920 may be generally circular, oval, square or otherwise shaped such that the bumps 1920 are configured to press into corresponding contact strips 1923 on the PCB 1922. The contact strips 1923 may be shaped differently as well. For example, the strips 1923 may be shaped so as to generally correspond to the cross-sectional shape of the bumps 1920. While there are two bumps 1920 per contact strip 1923 in the illustrated embodiment, other ratios of contact bumps 1920 to contract strips 1923 are possible. For example, there may be one contact bump 1920 per contact strip 1923, or more than two contact bumps 1920 per contact strip 1923.

Referring again to FIGS. 19D-19E, the frame 1918 includes rounded edges 1934 around which the various components including the inner shield 1926, the bonding layer 1924, the sending element 1920, and the outer shield 1928 wrap in the direction of the transverse axis 1938. The rounded edges 1934 help assure that the sensing element 1920 and other layers 1926, 1924, 1928 extend smoothly across the frame 3116, and do not include wrinkles, folds, crimps and/or unevenness. Rounded edges 1934 advantageously allow uniform application of the sensing element 1920 to the frame 1918, which helps assure uniform, accurate performance of the sensor assembly 1902. In addition, the dimensions of the rounded corners and the upper cavity 1930 can help to control the tension provided to the sensing element 1920 when it is stretched across the frame 1918.

The frame 1918 may have different shapes or configurations. For example, in some embodiments, the frame 1918 does not include a recess 1930 and the PCB 1922 sits on top of the frame 1918. In one embodiment the edges 1934 are not rounded. The frame 1918 may be shaped as a board, for example. The frame 1918 may include one or more holes. For example, the frame 1918 includes four elongate bars connected to form a hollow rectangle in one configuration. In various embodiments, the frame 1918 may not be generally rectangular but may instead be generally shaped as a square, circle, oval or triangle, for example. The shape of the frame 1918 may be selected so as to advantageously allow the sensor subassembly 1902 to be applied effectively to different areas of the body, for example. The shape of the frame 1918 may also be selected so as to conform to the shape of one or more of the other components of the sensor system 1900 such as the sensing element 1920.

In addition, in some embodiments, one or more of the inner shield 1926, the bonding layer 1924, the sensing layer 1920 and the outer shield 1928 are not wrapped around the frame 1918. For example, in one embodiment, one or more of these components are generally coextensive with and attached to the underside of the frame 1918 and do not include portions which wrap around the edges 1934 of the frame.

Sensing Element

The sensing element 1920 of certain embodiments is configured to sense acoustic vibrations from a measurement site of a medical patient. In one embodiment, the sensing element 1920 is a piezoelectric film, such as described in U.S. Pat. No. 6,661,161, incorporated in its entirety by reference herein, and in the '883 application. Referring still to FIGS. 19D-19E, the sensing element 1920 includes upper portions 1972 and lower planar portion 1962. As will be discussed, in an assembled configuration, the top of the upper portions 1972 include electrical contacts which contact electrical contacts on the PCB 1922, thereby enabling transmission of electrical signals from the sensing element 1920 for processing by the sensor system. The sensing element 1920 can be formed in a generally "C" shaped configuration such that it can wrap around and conform to the frame 1918. Sensing elements in accordance with embodiments described herein can also be found in the '883 application. In some embodiments, the sensing element 1920 includes one or more of crystals of tourmaline, quartz, topaz, cane sugar, and/or Rochelle salt (sodium potassium tartrate tetrahydrate). In other embodiments, the sensing element 1920 includes quartz analogue crystals, such as berlinite ($AlPO_4$) or gallium orthophosphate ($GaPO_4$), or ceramics with perovskite or tungsten-bronze structures ($BaTiO_3$, $SrTiO_3$, $Pb(ZrTi)O_3$, $KNbO_3$, $LiNbO_3$, $LiTaO_3$, $BiFcO_3$, $Na_xWO_3$, $Ba_2NaNb_5O_5$, $Pb_2KNb_5O_{15}$).

In other embodiments, the sensing element 1920 is made from a polyvinylidene fluoride plastic film, which develops piezoelectric properties by stretching the plastic while placed under a high pooling voltage. Stretching causes the film to polarize and the molecular structure of the plastic to align. For example, stretching the film under or within an electric field causes polarization of the material's molecules into alignment with the field. A thin layer of conductive metal, such as nickel-copper or silver is deposited on each side of the film as electrode coatings, forming electrical poles. The electrode coating provides an electrical interface between the film and a circuit.

In operation, the piezoelectric material becomes temporarily polarized when subjected to a mechanical stress, such as a vibration from an acoustic source. The direction and magnitude of the polarization depend upon the direction and magnitude of the mechanical stress with respect to the piezoelectric material. The piezoelectric material will produce a voltage and current, or will modify the magnitude of a current flowing through it, in response to a change in the mechanical stress applied to it. In one embodiment, the electrical charge generated by the piezoelectric material is proportional to the change in mechanical stress of the piezoelectric material.

Piezoelectric material generally includes first and second electrode coatings applied to the two opposite faces of the material, creating first and second electrical poles. The voltage and/or current through the piezoelectric material are measured across the first and second electrical poles. Therefore, stresses produced by acoustic waves in the piezoelectric material will produce a corresponding electric signal. Detection of this electric signal is generally performed by electrically coupling the first and second electrical poles to a detector circuit. In one embodiment, a detector circuit is provided with the PCB 1922, as described in greater detail below.

By selecting the piezoelectric material's properties and geometries, a sensor having a particular frequency response and sensitivity can be provided. For example, the piezoelectric material's substrate and coatings, which generally act as a dielectric between two poles, can be selected to have a particular stiffness, geometry, thickness, width, length, dielectric strength, and/or conductance. For example, in some cases stiffer materials, such as gold, are used as the electrode. In other cases, less stiff materials, such as silver, are employed. Materials having different stiffness can be selectively used to provide control over sensor sensitivity and/or frequency response.

The piezoelectric material, or film, can be attached to, or wrapped around, a support structure, such as the frame 1918. As shown in FIGS. 19D-19E, the geometry of the piezoelectric material can be selected to match the geometry of the frame. Overall, the sensor can optimized to pick up, or respond to, a particular desired sound frequency, and not other frequencies. The frequency of interest generally corresponds to a physiological condition or event that the sensor is intended to detect, such as internal bodily sounds, including, cardiac sounds (e.g., heart beats, valves opening and closing, fluid flow, fluid turbulence, etc.), respiratory sounds (e.g., breathing, inhalation, exhalation, wheezing, snoring, apnea events, coughing, choking, water in the lungs, etc.), or other bodily sounds (e.g., swallowing, digestive sounds, gas, muscle contraction, joint movement, bone and/or cartilage movement, muscle twitches, gastro-intestinal sounds, condition of bone and/or cartilage, etc.).

The surface area, geometry (e.g., shape), and thickness of the piezoelectric material 1920 generally defines a capacitance. The capacitance is selected to tune the sensor to the particular, desired frequency of interest. Furthermore, the frame 1918 is structured to utilize a desired portion and surface area of the piezoelectric material.

The capacitance of the sensor can generally be expressed by the following relationship: $C = \varepsilon S/D$, where C is the sensor's capacitance, $\varepsilon$ is the dielectric constant associated with the material type selected, S is the surface area of the material, and D is the material thickness (e.g., the distance between the material's conducive layers). In one embodiment, the piezoelectric material (having a predetermined capacitance) is coupled to an sensor impedance (or resistance) to effectively create a high-pass filter having a predetermined high-pass cutoff frequency. The high-pass cutoff frequency is generally the frequency at which filtering occurs. For example, in one embodiment, only frequencies above the cutoff frequency (or above approximately the cutoff frequency) are transmitted.

The amount of charge stored in the conductive layers of the piezoelectric material 1920 is generally determined by the thickness of its conductive portions. Therefore, controlling material thickness can control stored charge. One way to control material thickness is to use nanotechnology or MEMS techniques to precisely control the deposition of the electrode layers. Charge control also leads to control of signal intensity and sensor sensitivity. In addition, as discussed above, mechanical dampening can also be provided by controlling the material thickness to further control signal intensity and sensor sensitivity.

In addition, controlling the tension of the sensing element 1920 in the region where the mechanical stress (e.g., mechanical stress due to acoustic vibration from a patient's skin) is incident upon the sensing element 1920 can serve to improve the sensitivity of the sensing element 1920 and/or the coupling between the source of the signal (e.g., the patient's skin) and the sensing element 1920. This feature will be discussed in greater detail below with respect to the coupler 1914.

Figures 20A, 20B, 20C:
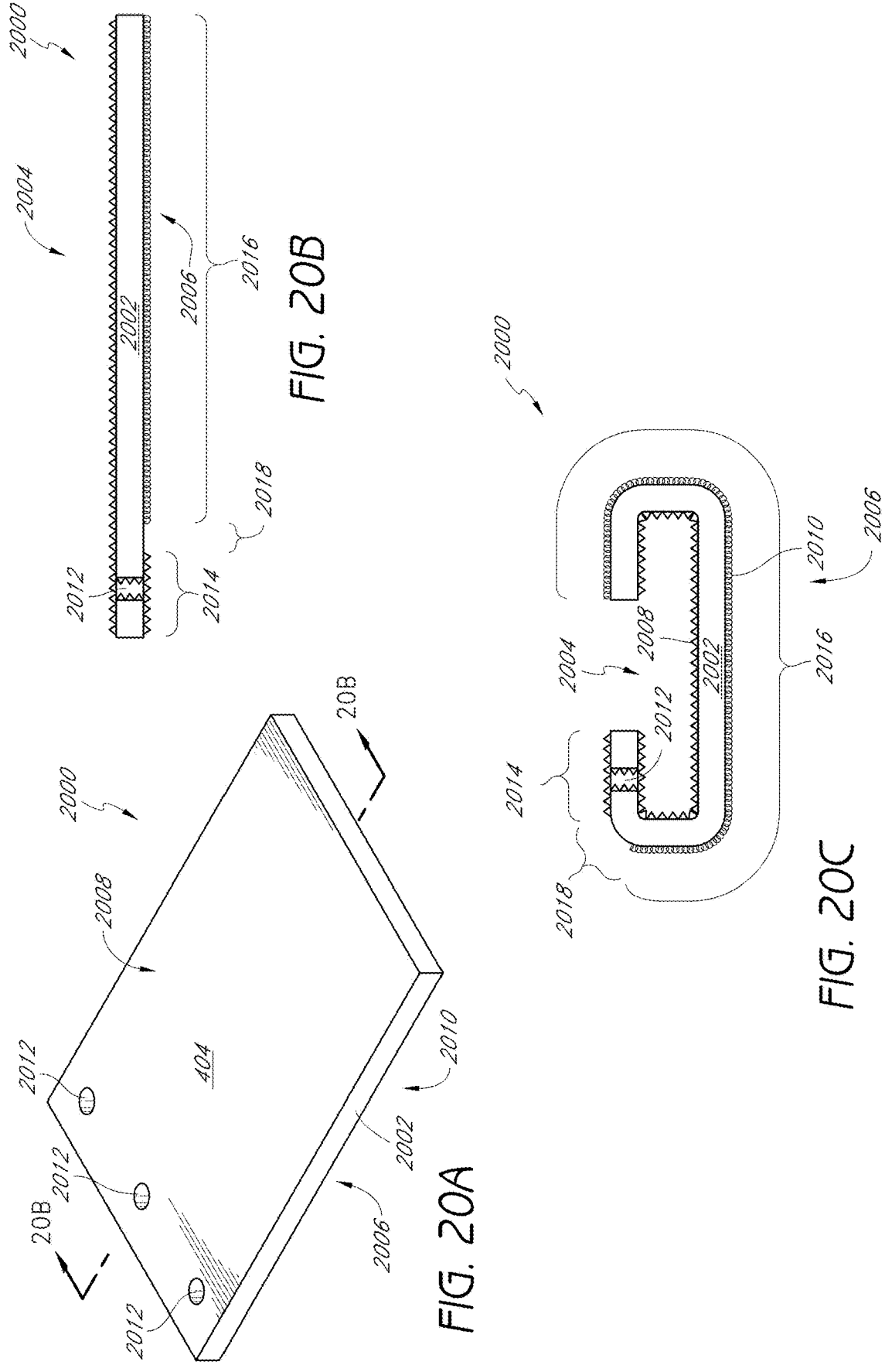
FIG. 20A a perspective view of a sensing element according to an embodiment of the disclosure usable with the sensor assembly of FIG. 19A.
FIG. 20B is a cross-sectional view of the sensing element of FIG. 20A along the line 20B-20B.
FIG. 20C is a cross-sectional view of the sensing element of FIGS. 20A-B shown in a wrapped configuration.

One embodiment of a piezoelectric sensing element 2000 is provided in FIGS. 20A-C. The sensing element 2000 includes a substrate 2002 and coatings 2004, 2006 on each of its two planar faces 2008, 2010. The planar faces 2008, 2010 are substantially parallel to each other. At least one through hole 2012 extends between the two planar faces 2008, 2010. In one embodiment, the sensing element 2000 includes two or three through holes 2012.

In one embodiment, a first coating 2004 is applied to the first planar face 2008, the substrate 2002 wall of the through holes 2012, and a first conductive portion 2014 of the second planar face 2010, forming a first electrical pole. By applying a first coating 2004 to the through holes 2012, a conductive path is created between the first planar face 2008 and the first conductive portion 2014 of the sensing element 2000. A second coating 2006 is applied to a second conductive portion 2016 of the second planar face 2010 to form a second electrical pole. The first conductive portion 2014 and second conductive portion 2016 are separated by a gap 2018 such that the first conductive portion 2014 and second conductive portion 2016 are not in contact with each other. In one embodiment, the first conductive portion 2014 and second conductive portion 2016 are electrically isolated from one another.

In some embodiments, the first and second conductive portions 2014, 2016 are sometimes referred to as masked portions, or coated portions. The conductive portions 2014, 2016, can be either the portions exposed to, or blocked from, material deposited through a masking, or deposition process. However, in some embodiments, masks aren't used. Either screen printing, or silk screening process techniques can be used to create the first and second conductive portions 2014, 2016.

In another embodiment, the first coating 2004 is applied to the first planar face 2008, an edge portion of the substrate 2002, and a first conductive portion 2014. By applying the first coating 2004 to an edge portion of the substrate 2002, through holes 2012 can optionally be omitted.

In one embodiment, the first coating 2004 and second coating 2006 are conductive materials. For example, the coatings 2004, 2006 can include silver, such as from a silver deposition process. By using a conductive material as a coating 2004, 2006, the multi-parameter sensor assembly can function as an electrode as well.

Electrodes are devices well known to those of skill in the art for sensing or detecting the electrical activity, such as the electrical activity of the heart. Changes in heart tissue polarization result in changing voltages across the heart muscle. The changing voltages create an electric field, which induces a corresponding voltage change in an electrode positioned within the electric field. Electrodes are typically used with echo-cardiogram (EKG or ECG) machines, which provide a graphical image of the electrical activity of the heart based upon signal received from electrodes affixed to a patient's skin.

Therefore, in one embodiment, the voltage difference across the first planar face 2008 and second planar face 2010 of the sensing element 2000 can indicate both a piezoelectric response of the sensing element 2000, such as to physical aberration and strain induced onto the sensing element 2000 from acoustic energy released from within the body, as well as an electrical response, such as to the electrical activity of the heart. Circuitry within the sensor assembly and/or within a physiological monitor (not shown) coupled to the sensor assembly distinguish and separate the two information streams. One such circuitry system is described in U.S. Provisional No. 60/893,853, filed Mar. 8, 2007, titled, "Multi-parameter Physiological Monitor," which is expressly incorporated by reference herein.

Referring still to FIGS. 20A-C, the sensing element 2000 is flexible and can be wrapped at its edges, as shown in FIG. 20C. In one embodiment, the sensing element 2000 is the sensing element 1920 wrapped around the frame 1918, as shown in FIGS. 19D and 19E. In addition, by providing both a first conductive portion 2014 and a second conductive portion 2016, both the first coating 2004 and second coating 2006 and therefore the first electrical pole of and the second electrical pole of the sensing element 2000 can be placed into direct electrical contact with the same surface of the PCB, such as the PCB 1922 as shown FIGS. 5A-B below. This advantageously provides symmetrical biasing of the sensing element 2000 under tension while avoiding uneven stress distribution through the sensing element 2000.

Bonding Layer

Referring back to FIGS. 19D-19E, the bonding layer 1924 (sometimes referred to as an insulator layer) of certain embodiments is an elastomer and has adhesive on both of its faces. In other embodiments, the bonding layer 1924 is a rubber, plastic, tape, such as a cloth tape, foam tape, or adhesive film, or other compressible material that has adhesive on both its faces. For example, in one embodiment, the bonding layer 1924 is a conformable polyethylene film that is double coated with a high tack, high peel acrylic adhesive. The bonding layer 1924 in some embodiments is about 2, 4, 6, 8 or 10 millimeters thick.

The bonding layer 1924 advantageously forms a physical insulation layer or seal between the components of the sensor subassembly 1902 preventing substances entering and/or traveling between certain portions of the sensor subassembly 1902. In many embodiments, for example, the bonding layer 1924 forms a physical insulation layer that is water resistant or water proof, thereby providing a water-proof or water-resistant seal. The water-resistant properties of the bonding layer 1924 provides the advantage of preventing moisture from entering the acoustic chamber or lower cavity 1936. In certain embodiments, the sensing element 1920, the bonding layer 1924 and/or the shield layers 1926, 1928 (described below) form a water resistant or water proof seal. The seal can prevent moisture, such as perspiration, or other fluids, from entering portions of the sensor subassembly 1902, such as the cavity 1936 when worn by a patient. This is particularly advantageous when the patient is wearing the multi-parameter sensor assembly 1900 during physical activity. The water-resistant seal prevents current flow and/or a conductive path from forming from the first surface of the sensing element 1920 to its second surface or vice versa as a result of patient perspiration or some other moisture entering and/or contacting the sensing element 1920 and/or sensor assembly 1915.

The bonding layer 1924 can also provide electrical insulation between the components of the sensor subassembly 1902, preventing the flow of current between certain portions of the sensor subassembly 1902. For example, the bonding layer 1924 also prevents the inside electrical pole from shorting to the outside electrical pole by providing electrical insulation or acting as an electrical insulator between the components. For example, in the illustrated embodiment, the bonding layer 1924 provides electrical insulation between the sensing element 1920 and the inner shield layer 1926, preventing the inside electrical pole of the sensing element 1920 from shorting to the outside electrical pole. In another embodiment, a bonding layer is placed between the outer surface of the sensing element 1920 and the outer shield layer 1928.

The elasticity or compressibility of the bonding layer 1924 can act as a spring and provide some variability and control in the pressure and force provided between the sensing element 1920 and PCB 1922. In some embodiments, the sensor assembly does not include a bonding layer 1924.

Electrical Noise Shielding Barrier

An electrical noise shielding barrier can electrically shield the electrical poles of the sensing element from external electrical noises. In some embodiments the electrical shielding barrier can include one or more layers which form a Faraday cage around a piezoelectric sensing element, and which distribute external electrical noise substantially equally to the electrical poles of the piezoelectric sensing element. In addition, the shielding barrier flexibly conforms to the surface shape of the piezoelectric element as the surface shape of the piezoelectric element changes, thereby improving the shielding and sensor performance.

Referring still to FIGS. 19D-19E, the electrical shielding barrier 1927 of the illustrated embodiment includes first and second shield layers 1926, 1928 (also referred to herein as inner and outer shield layers 1926, 1928) which form a Faraday cage (also referred to as a Faraday shield) which encloses the sensing element 1920 and acts to reduce the effect of noise on the sensing element from sources such as external static electrical fields, electromagnetic fields, and the like. As will be described, one or more of the inner and outer shield layers 1926, 1928 advantageously conform to the contours of the sensing element 1920 during use, allowing for enhanced shielding of the sensing element from external electrical noise.

The inner and outer shield layers 1926, 1928 include conductive material. For example, the inner and outer shield layers 1926, 1928 include copper in certain embodiments and are advantageously formed from a thin copper tape such that the layers can conform to the shape, contours and topology of the sensor element 1920 and the frame 1918. In some configurations, other materials (e.g., other metals) or other combinations of materials can be used. Moreover, as described herein with respect to FIGS. 19-22, the electrical shielding barrier 1927 or portions thereof, such as one or more of the first and second shield layers 1926, 1928, can be formed from piezoelectric films. In such embodiments, the sensor 1915 can include first and second piezoelectric films arranged in a stack, and the shielding barrier 1927 can be formed from the outer electrode of each film in the stack.

In various embodiments, one or more of the inner and outer shield layers 1926, 1928 are from between about 0.5 micrometer and 10 micrometers thick. For example, the shield layers 1926, 1928, may be from between about 1.5 and about 6 micrometers thick. In one embodiment, the inner and outer shield layers 1926, 1928 include copper tape about 3 micrometers thick. In yet other embodiments, the shield layers 1926, 1928 may be greater than 10 micrometers thick or less than 0.5 micrometers thick. In general, the thickness of the shield layer 1926, 1928 is selected to provide improved electrical shielding while allowing for the shield layers 1926, 1928 to conform to the sensor element 1920 and/or the frame 1918. The inner shield layer 1926 includes an adhesive on the inside surface 1952 such that it can adhere to the frame 1918. The inner shield layer 1926 adheres directly to the frame 1918 and advantageously conforms to the contours of the frame such as the rounded edges 1934 and the lower cavity 1936, adhering to the surface 1950 defining the base of the cavity 1936. The bonding layer 1924 (e.g., a tape adhesive) is wrapped around and generally conforms to the contours of the inner shield layer 1926 and the frame 1918. The sensing element 1920 is wrapped around the bonding layer 1924, the inner shield layer 1924 and the frame 1918. The outer shield layer 1928 is wrapped around and advantageously conforms to the contours of the sensing element 1920 and the frame 1918. In certain embodiments, a bonding or insulating layer is positioned between the sensing element 1920 and the outer shielding layer 1928 as well. As such, the sensing element 1920 is sandwiched between and enclosed within the inner and outer shield layers 1926, 1928 which form a Faraday cage around the sensing element 1920. The configuration of the shield layers 1926, 1928, the sensing element 1920 and the bonding layer 1924 will be described in greater detail below with respect to FIGS. 5A-B.

In certain embodiments, the shield layers 1926, 1928 are coupled to a common potential (e.g., ground) or are otherwise operatively coupled, and each of the shield layers 1926, 1928 are also electrically (e.g., capacitively) coupled to one of the poles of the sensing element 1920. For example, the shielding layer 1926 may be capacitively coupled to the first electrode of the sensing element 1920, and the shielding layer 1928 may be capacitively coupled to the second electrode of the sensing element 1920.

As discussed, the electrical shielding barrier 1927 such as the Faraday cage formed by the inner and outer shield layers 1926, 1928 helps to reduce the effect of noise electrical noise on the sensing element 1920 from sources such as external static electrical fields and electromagnetic fields, thereby lowering the noise floor, providing better noise immunity, or both. For example, the electrical shielding barrier 1927 allows for the removal of electrical interference or noise incident directed towards the sensing element 1920 while allowing the non-noise component of the sensed signal indicative of bodily sounds to be captured by the sensor 1915. For example, in one embodiment the sensing element 1920 is a piezoelectric film such as one of the piezoelectric films described herein having positive and negative electrical poles and configured in a differential mode of operation. The electrical shielding barrier 1927 acts to balance the effect of the noise by distributing at least a portion of the noise substantially equally to the positive and negative electrical poles of the piezoelectric element. In some embodiments, the electrical shielding barrier 1927 distributes the noise equally to both the positive and negative poles. Moreover, the noise signals distributed to the positive and negative electrical poles are substantially in phase or actually in phase with each other. For example, the noise signals distributed to the positive and negative poles are substantially similar frequencies and/or amplitudes with substantially no phase shift between them.

For example, in certain embodiments, noise incident on the shielding barrier 1927 is substantially equally distributed to each of the shielding layers 1926, 1928 because these layers are at a common potential (e.g., ground). The substantially equally distributed noise may then be coupled (e.g., capacitively coupled) to the poles of the sensing element 1920. In certain embodiments, at least some of the external electrical noise is shunted or otherwise directed to ground by the shield layers 1926, 1928 instead of, or in addition to, being distributed to the poles of the sensing element 1920.

Because the noise signal components on the positive and negative poles are substantially in phase, the difference between the noise components on the respective poles is negligible or substantially negligible. On the other hand, the difference between the differential non-noise sensor signal components indicative of bodily sounds on the positive and negative poles will be non-zero because the sensing element is configured in a differential mode. As such, the noise signals can advantageously be removed or substantially removed through a common-mode rejection technique.

For example, a common-mode rejection element may receive a signal including the combined noise and non-noise sensor signal components of the positive and negative poles, respectively. The common-mode rejection element is configured to output a value indicative of the difference between the combined signal on the positive pole and the combined signal on the negative pole. Because the difference between the noise signals is negligible, the output of the common-mode rejection element will be substantially representative of the non-noise component of the sensor signal and not include a significant noise component. The common mode rejection element may include, for example, an operational amplifier. In one embodiment, for example, three operational amplifiers (not shown) are used and they are disposed on the PCB 1922.

Because the shielding layers 1926, 1928 conform to the topology of the frame 1918 and the sensing element 1920, the shielding layers 1926, 1928 are physically closer to the electrical poles of the sensing element 1920 and are more uniformly displaced from the sensing element 1920. Moreover, the outer shield layer 1928 of certain embodiments actively moves with and conforms to the contours of the sensing element 1920 during use, such as when the sensor assembly is placed against the skin or when the sensing element 1920 is moving due to acoustic vibrations. For example, when placed against the skin, the coupling element 1958 pushes against both the outer shielding layer 1928 of the shielding barrier 1927 and the sensing element 1920, causing them to curve along the inside surface of the coupling element 1958 (FIG. 5A). Because the cage is flexible and can conform to the movement of the shielding element 1920, the shielding performance and sensor performance is improved. This arrangement provides advantages such as for example, for the noise signals to be more accurately and evenly distributed to the positive and negative electrical poles of the sensing element 1920 by the shielding layers 1926, 1928, thereby providing enhanced noise reduction. This arrangement can also provide for improved manufacturability and a more stream-lined design.

Alternative configurations for the electrical shielding barrier 1927 are possible. For example, the inner shield layer may not include an adhesive layer and may, for example, be held in place against the frame 1918 by pressure (e.g., from the locking posts 1932). The outer shield 1928 may also include an adhesive layer in some embodiments. In various other embodiments, the shield layers 1926, 1928 may include other materials such as other types of metals. One or more of the shield layers may be relatively rigid in some configurations. In one embodiment, an insulating layer or bonding layer is disposed between sensing element 1920 and the outer shield layer 1928. In some embodiments, the inner shield layer 1926 actively conforms to the contours of the sensing element 1920 during use in addition to the outer shield layer 1928. In another embodiment, the inner shield layer 1926 actively conforms to the sensing element 1920 during use and the outer shield layer 1928 does not. In yet other embodiments, the sensor assembly 1901 does not include an electrical shielding barrier 1927.

Acoustic Coupler

The sensor may also include an acoustic coupler or biasing element, which advantageously improves the coupling between the source of the signal to be measured by the sensor (e.g., the patient's skin) and the sensing element. The acoustic coupler generally includes a coupling portion positioned to apply pressure to the sensing element so as to bias the sensing element in tension. For example, the acoustic coupler may include one or more bumps, posts or raised portions which provide such tension. The bumps, posts or raised portions may be positioned on the inner surface of the coupler, the outer surface of the coupler, or both and may further act to evenly distribute pressure across the sensing element. In addition, the acoustic coupler can be further configured to transmit bodily sound waves to the sensing element. The acoustic coupler can also be configured to provide electrical isolation between the patient and the electrical components of the sensor.

In the illustrated embodiment, the acoustic coupler 1914 houses the other components of the sensor subassembly including the frame 1918, the PCB 1922, the shield layers 1926, 1928, the bonding layers 1924 and the sensing element 1920. The acoustic coupler 1914 includes a non-conductive material or dielectric. As shown, the acoustic coupler 1914 generally forms a dielectric barrier between the patient and the electrical components of the sensor assembly 1901. As such, the acoustic coupler 1914 provides electrical isolation between the patient and the electrical components of the sensor subassembly 1902. This is advantageous in avoiding potential harmful electrical pathways or ground loops forming between the patient and the sensor.

As shown in FIGS. 19D-19E, the acoustic coupler 1914 is formed in a hollow shell capable of housing the components of the other sensor subassembly 1902. Referring to FIG. 19D, the acoustic coupler 1914 of the illustrated embodiment also includes recesses 1956 and holes 1952 capable of receiving and securing the button 1912 (FIG. 19B) and portions of the elongate member 1910 (FIG. 19B) of the attachment subassembly 1904.

Figure 21:
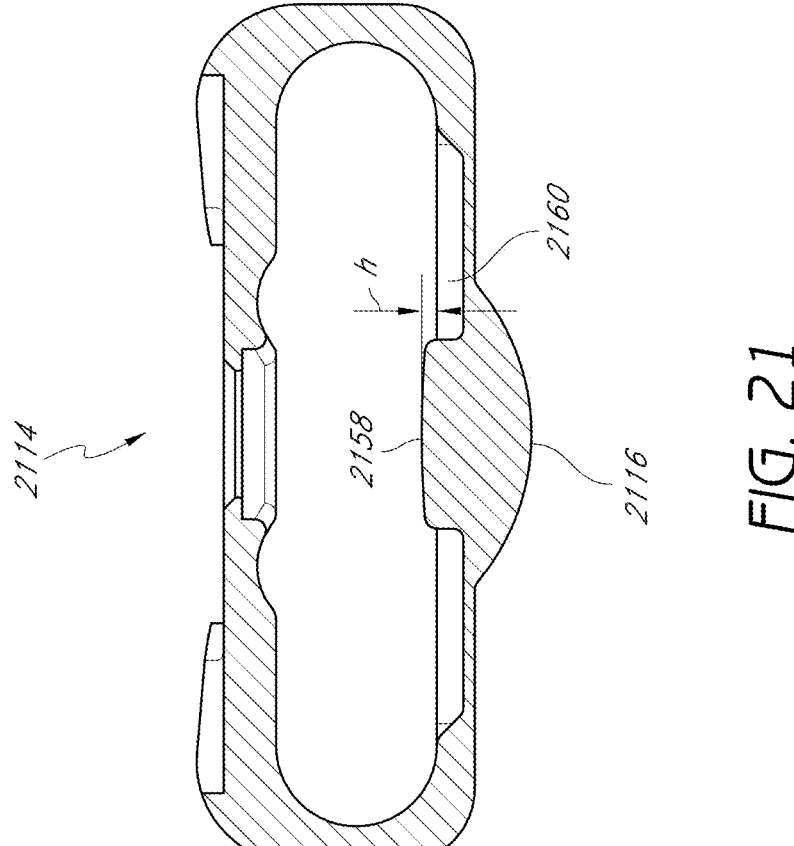
FIG. 21 is a cross-sectional view of the coupler of FIGS. 19A-19E taken along the line 21-21 shown in FIG. 19D.

FIG. 21 is a cross-sectional view of the acoustic coupler 1914 taken along the line 21-21. In certain embodiments, the acoustic coupler includes a bump or protrusion on the inner surface of the coupler 1914 and configured to advantageously bias the sensing membrane in tension. For example, a coupling element 1958 is disposed on the on the interior bottom portion of the acoustic coupler 1914 and which biases the sensing element 1920 in tension. The coupling element 1958 of the illustrated embodiment is a generally rectangular bump which extends by a height h above the cavity 1960 which is formed on the interior bottom of the acoustic coupler 1914. The coupling element 1958 is centered about and extends along the longitudinal axis 1940 (FIGS. 19D and 19E) from near the front of the acoustic coupler 1914 to near the back of the acoustic coupler 1914. In the illustrated embodiment, the coupling element 1958 is about ¼ of the width of the acoustic coupler 1914 along the transverse axis 1938. As will be discussed in greater detail below with respect to FIG. 22A-B, the coupling element 1958 can advantageously bias the sensing element 1920 in tension by applying pressure to the sensing element 1920. Because the sensing element 1920 may be generally taut in tension under the pressure of the coupling bump 1958, the sensing element 1920 will be mechanically coupled to the coupling bump 1958 and responsive to acoustic vibrations travelling through the coupler 1914 to the sensing element 1920, thereby providing improved coupling between the patient's skin and the sensing element 1920. As such, the acoustic coupler 1914 provides for improved measurement sensitivity, accuracy, or both, among other advantages.

The acoustic coupler 1914 is further configured to transmit bodily sound waves to the sensing element 1920. The coupler 1914 can further include a portion disposed on the outer surface of the coupler 1914 and which is configured to contact the skin during use. For example, the acoustic coupler 1914 can include an outer protrusion, bump or raised portion on the outer surface. Referring to FIGS. 19E and 4, the underside of the acoustic coupler 1914 includes portion 1916 which is configured to contact the skin of the patient and can provides contact between the skin and the acoustic coupler 1914. Acoustic vibrations from the skin will be incident on the portion 1916, travel through the acoustic coupler to the coupling bump 1958 and eventually be incident on the sensing element 1920 held in tension by the bump 1958. In addition, the contact portion 1916 may, in conjunction with the coupling element 1958 or on its own, also help to improve the coupling between the skin and the sensing element 1920. For example, when pressed against the skin, the contact portion 1916 may push a portion of the inner surface of the coupler 1914, such as the coupling element 1958, into the sensing element 1920, advantageously holding the sensing element 1920 in tension. As shown, the contact portion 1916 of the illustrated embodiment includes a semi-cylindrical bump mounted generally underneath the coupling element 1958. Similar to the coupling element 1958, the contact portion 1916 is centered about and extends along the longitudinal axis 1940 from near the front of the acoustic coupler 1914 to near the back of the acoustic coupler 1914. Moreover, the acoustic coupler 1914 acts to evenly distribute pressure to the sensing element 1920 during use. For example, because the coupling element 1958 and the portion 1916 are generally positioned such that they are centered with respect to surface of the sensing element 1920, pressure will be distributed symmetrically and/or evenly across the sensing element 1920.

Referring to FIG. 19E, a pair of slots 1964 are disposed on either end of the contact portion 1916 and each run generally along the transverse axis from near the left side of the acoustic coupler 1914 to the right side of the acoustic coupler 1914. The slots serve to decouple a segment 1966 of the bottom of the acoustic coupler 1914 including the coupling element 1958 and the contact portion 1916 from the remainder of the acoustic coupler 1914. As such, the segment 1966 can move at least partially independent from the rest of the acoustic coupler 1914 in response to acoustic vibrations on the skin of the patient, thereby efficiently transmitting acoustic vibrations to the sensing element 1920. The acoustic coupler 1914 of certain embodiments includes an elastomer such as, for example, rubber or plastic material.

In an alternative embodiment of the acoustic coupler 1914, for example, the acoustic coupler 1914 does not include a hollow shell and does not house the other components of the sensor subassembly. For example, the coupler 1914 may include a single planar portion such as, for example, a board which couples to the underside of the frame 1918 such that the shielding layers 1926, 1928, the sensing element 1920 and the bonding layer 1924 are positioned between the coupler 1914 and the frame 1918. In some configurations, the coupler 1914 is positioned between the frame 1918 and one or more of the shielding layers 1926, 1928, the sensing element 1920 and the bonding layer 1924. Moreover, the acoustic coupler 1914 may include a dielectric material, which advantageously electrically isolates the electrical components of the sensor subassembly 1902 from the patient. For example, the dielectric layer may ensure that there is no electrical connection or continuity between the sensor assembly and the patient.

In certain embodiments, portions of the sensor assembly such as, for example, the acoustic coupler 1914 may include a gel or gel-like material. The gel may provide beneficial acoustic transmission, for example, serving to enhance the coupling between the acoustic vibrations from the patient's skin and the sensing element 1920. The gel may provide acoustic impedance matching, for example, between the skin and the sensor. For example, the gel may serve to reduce the impedance mismatch from potential skin-to-air and air-to-sensing element discontinuity, thereby reducing potential reflections and signal loss. The gel may be embedded in a portion of the acoustic coupler 1914. For example, one or more of the coupling element 1958 and the contact portion 1916 may include a gel or gel-like material. The acoustic coupler 1914 may include an embedded gel in certain embodiments where one or more of the coupling element 1958 and the contact portion 1916 are not included. For example, the entire patient contact portion of the acoustic coupler 1914 may include gel material extending substantially from the patient contact surface to the interior of the coupler 1914 across the contact portion. One or more columns of gel material may extend from the patient contact surface of the coupler 1914 to the interior of the coupler 1914 in other embodiments. In yet further embodiments, the gel is not embedded in the acoustic coupler 1914 but is added to the skin directly. In one embodiment, the gel is embedded in the acoustic coupler 1914 and is configured to be released from the coupler 1914 when the sensor assembly is applied to the patient. For example, gel can be filled in one or more cavities of the acoustic coupler 1914 prior to use wherein the cavities are configured to open and release the gel when the coupler is pressed against the skin.

Figure 22B:
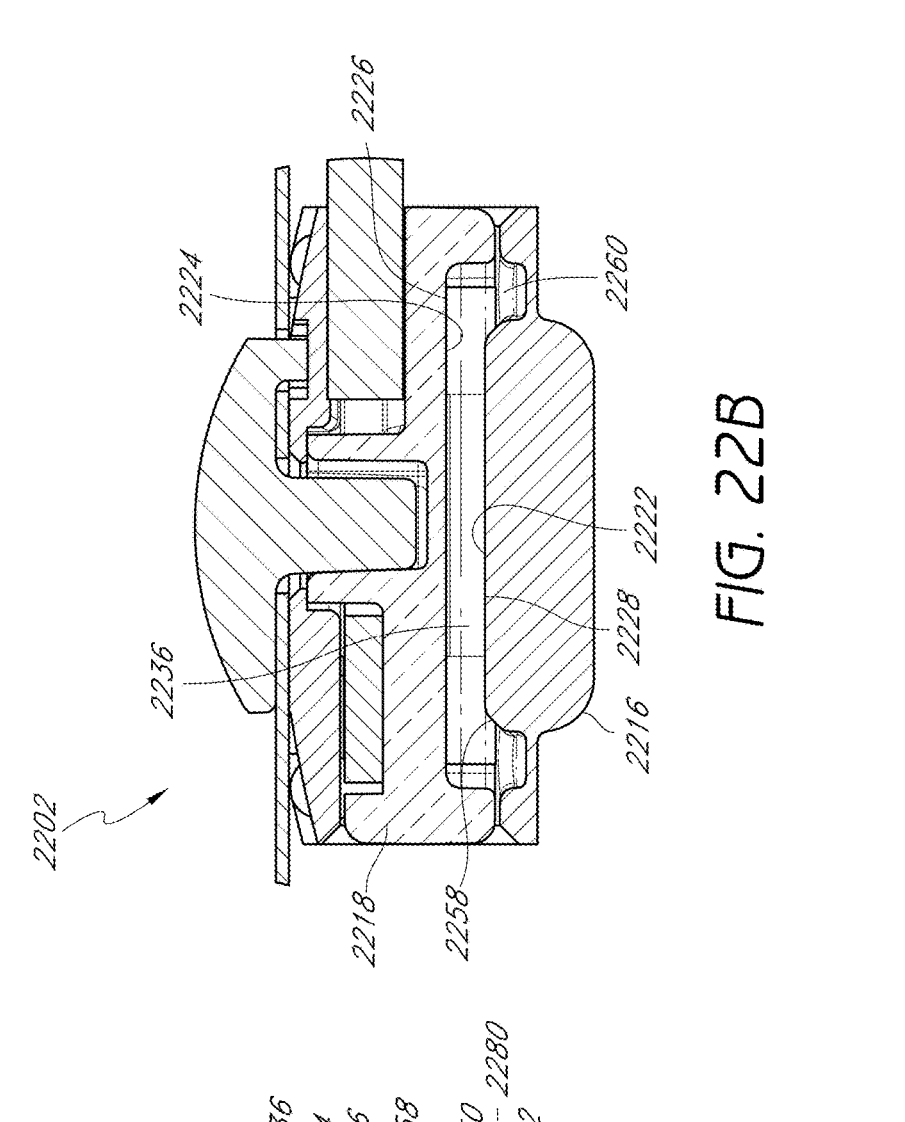
FIGS. 22A-22B are cross-sectional views of the sensor subassembly of FIGS. 19B-19C along the lines 22A-22A and 22B-22B, respectively.
Figure 22A:
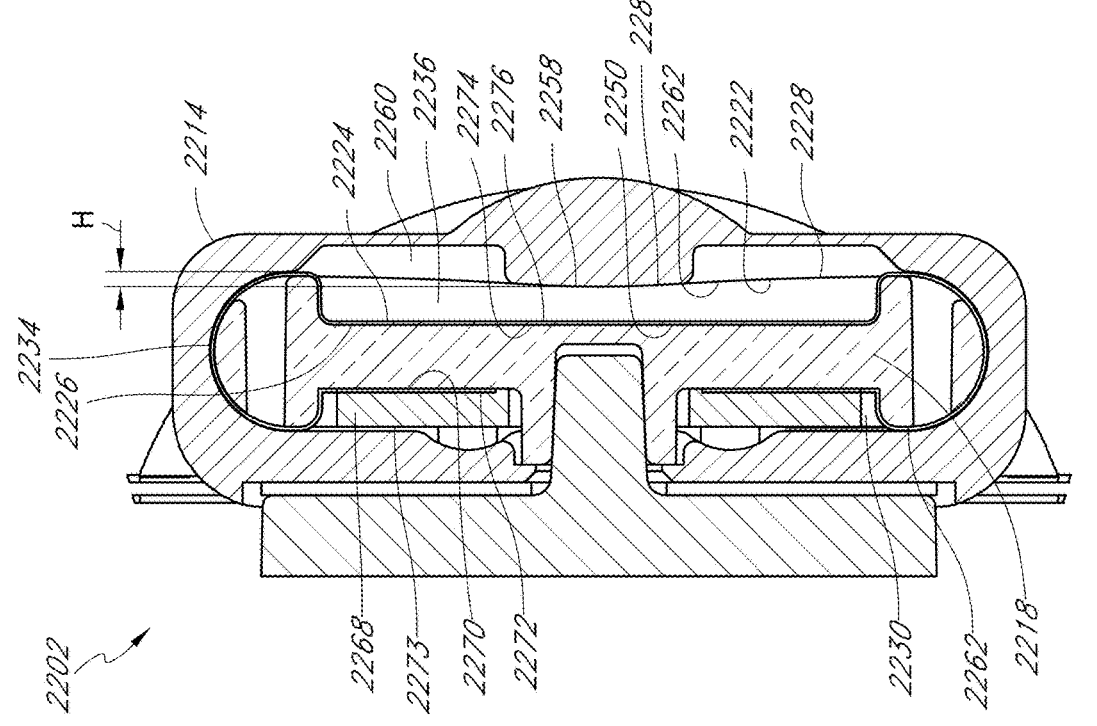

FIGS. 22A-B are cross-sectional views of the sensor subassembly 1902 of FIG. 19 along the lines 22A-22A and 22B-22B, respectively. As shown, the inner copper shield 1926 is positioned as the inner most of the shield layers 1926, 1928, the bonding layer 1924 and the sensing element 1920. Referring to FIGS. 19D-E and FIGS. 22A-B, the four tabs 1968 of the inner copper shield 1926 are flat and extend across the top of the frame recess 1930 and the four corners of the top surface of the PCB (not shown in FIGS. 22A-B) which sits in the frame recess 1930. The bonding layer 1924 is wrapped around the inner copper shield 1926. The upper portions 1970 of the bonding layer 1924 bend downward to conform to the shape of the frame 1918 such that they extend across and contact the bottom of the frame cavity 1930. The sensing element 1920 is wrapped around the bonding layer 1924 and the upper portions 1972 of the sensing element 1920 also bend downward to conform to the shape of the frame 1918. As such, the upper portions 1972 of the sensing element 1920 extend across the bottom of the frame cavity 1930 and are in contact with the bottom of the PCB 1922 and the top surface of the bonding layer 1924. The outer copper layer 1928 is wrapped around the sensing element 1920 and the upper planar portions 1973 of the outer copper shield 1928 are flat, extend across the top of the frame recess 1930, and are in contact with the top surface of the PCB (not shown).

The shield layers 1926, 1928, the bonding layer 1924 and the sensing element 1920 wrap around the rounded edges 1934 of the frame 1918. The lower planar portions 1974, 1976 of the inner shield layer 1926 and the bonding layer 1924 bend upwards so as extend across the bottom surface 1950 of the frame 1918. The lower planar portions 1962, 1980 of the sensing element 1920 and the outer shield layer 1928, on the other hand, extend between the lower frame cavity 1936 and the coupler cavity 1960. Moreover, the lower planar portions 1962, 1980 of the sensing element 1920 and the outer shield layer 1928 extend across the top of the coupling portion 1958. Because the coupler portion 1958 extends slightly above the coupler cavity 1960 into the lower frame cavity 1936 by the distance h, the sensing element 1920 is advantageously biased in tension improving the sensitivity of the sensing element 1920, the coupling of the sensing element 1920 to acoustic vibrations in the skin of the patient (not shown), or both.

In various embodiments, the components of the sensor subassembly 1902 may be arranged differently. For example, the components may be combined such that the overall assembly include fewer discrete components, simplifying manufacturability. In one embodiment, one or more of the shielding layers 1926, 1928, the bonding layer 1924 and the sensing element 1920 may include an integral portion (e.g., a multi-layered film). In some embodiments, more than one bonding layer 1924 is used. In one embodiment, adhesive layers are formed on one or more of the shielding layers 1926, 1928 and the sensing element 1920, and no separate bonding layer 1924 is present. In another embodiment, the various layers are held together by pressure (e.g., from the contact posts 1932 and/or PCB) instead of through the use of adhesives.

Referring still to FIGS. 19D-E and 22A-B, a method for attaching the shielding layers 1926, 1928, the bonding layer 1924, the sensing element 1920 and the PCB 1922 to the frame 1918 includes providing the inner shield 1926 and attaching it to the frame 1918. The sensing element 1920 and bonding layer 1924 are provided and also attached to the frame 1918. A printed circuit board 1922 is then provided. The printed circuit board 1922 is placed on top of the sensing element 1920 such that a first edge 1980 of the printed circuit board 1922 is placed over a first conductive portion of the sensing element 1920, and a second edge 1982 of the printed circuit board 1922 is placed over a second conductive portion of the sensing element 1920.

The printed circuit board 1922 is pressed down into the sensing element 1920 in the direction of the frame 1918. As the printed circuit board 1922 is pressed downward, the contact bumps (not shown) of the frame 1918 push the bonding layer 1924 and sensing element 1920 into contact strips located along the first and second sides or edges 1980, 1982 of the printed circuit board 1922. The contact strips of the printed circuit board 1922 are made from conductive material, such as gold. Other materials having a good electro negativity matching characteristic to the conductive portions of the sensing element 1920, may be used instead. The elasticity or compressibility of the bonding layer 1924 acts as a spring, and provides some variability and control in the pressure and force provided between the sensing element 1920 and printed circuit board 1922.

Once the outer shield 1928 is provided and attached to the frame 1918, a desired amount of force is applied between the PCB 1922 and the frame 1918 and the locking posts 1932 are vibrated or ultrasonically or heated until the material of the locking posts 1932 flows over the PCB 1922. The locking posts 1932 can be welded using any of a variety of techniques, including heat staking, or placing ultrasonic welding horns in contact with a surface of the locking posts 1932, and applying ultrasonic energy. Once welded, the material of the locking posts 1932 flows to a mushroom-like shape, hardens, and provides a mechanical restraint against movement of the PCB 1922 away from the frame 1918 and sensing element 1920. By mechanically securing the PCB 1922 with respect to the sensing element 1920, the various components of the sensor sub-assembly 1902 are locked in place and do not move with respect to each other when the multi-parameter sensor assembly is placed into clinical use. This prevents the undesirable effect of inducing electrical noise from moving assembly components or inducing instable electrical contact resistance between the PCB 1922 and the sensing element 1920. In certain embodiments, the locking posts 1932 provide these advantages substantially uniformly across multiple sensors.

Therefore, the PCB 1922 can be electrically coupled to the sensing element 1920 without using additional mechanical devices, such as rivets or crimps, conductive adhesives, such as conductive tapes or glues, like cyanoacrylate, or others. In addition, the mechanical weld of the locking posts 1932 helps assure a stable contact resistance between the PCB 1922 and the sensing element 1920 by holding the PCB 1922 against the sensing element 1920 with a constant pressure, for example, and/or preventing movement between the PCB 1922 and the sensing element 1920 with respect to each other.

The contact resistance between the sensing element 1920 and PCB 1922 can be measured and tested by accessing test pads on the PCB 1922. For example, in one embodiment, the PCB 1922 includes three discontinuous, aligned test pads that overlap two contact portions between the PCB 1922 and sensing element 1920. A drive current is applied, and the voltage drop across the test pads is measured. For example, in one embodiment, a drive current of about 100 mA is provided. By measuring the voltage drop across the test pads the contact resistance can be determined by using Ohm's law, namely, voltage drop (V) is equal to the current (I) through a resistor multiplied by the magnitude of the resistance (R), or V=IR. While one method for attaching the shield layers 1926, 1928, the bonding layer 1924, the sensing element and the PCB 1922 to the frame 1918 has been described, other methods are possible. For example, as discussed, in some embodiments, one or more of the various separate layers are combined in an integral layer which is attached to the frame 1918 in one step.

Printed Circuit Board

The PCB 1922 includes various electronic components mounted to either or both faces of the PCB 1922. When sensor assembly is assembled and the PCB 1922 is disposed in the upper frame cavity 1930, some of the electronic components of the PCB 1922 may extend above the upper frame cavity 1930. To reduce space requirements and to prevent the electronic components from adversely affecting operation of the sensor assembly, the electronic components can be low-profile, surface mounted devices. The electronic components are often connected to the PCB 1922 using conventional soldering techniques, for example the flip-chip soldering technique. Flip-chip soldering uses small solder bumps such of predictable depth to control the profile of the soldered electronic components. The four tabs 1968 of the inner copper shield 1926 and the upper planar portions 1973 of the outer copper shield 1928 are soldered to the PCB 1922 in one embodiment, electrically coupling the electrical shielding barrier to the PCB 1922.

In some embodiments, the electronic components include filters, amplifiers, etc. for pre-processing or processing a low amplitude electric signal received from the sensing element 1920 (e.g., the operational amplifiers discussed above with respect to the Faraday cage) prior to transmission through a cable to a physiological monitor. In other embodiments, the electronic components include a processor or pre-processor to process electric signals. Such electronic components may include, for example, analog-to-digital converters for converting the electric signal to a digital signal and a central processing unit for analyzing the resulting digital signal.

In other embodiments, the PCB 1922 includes a frequency modulation circuit having an inductor, capacitor and oscillator, such as that disclosed in U.S. Pat. No. 6,661,161, which is incorporated by reference herein. In another embodiment, the PCB 1922 includes an FET transistor and a DC-DC converter or isolation transformer and phototransistor. Diodes and capacitors may also be provided. In yet another embodiment, the PCB 3114 includes a pulse width modulation circuit.

In one embodiment, the PCB 1922 also includes a wireless transmitter, thereby eliminating mechanical connectors and cables. For example, optical transmission via at least one optic fiber or radio frequency (RF) transmission is implemented in other embodiments. In other embodiments, the sensor assembly includes an information element which can determine compatibility between the sensor assembly and the physiological monitor to which it is attached and provide other functions, as described below.

Additional Example Sensor

Figure 23A:
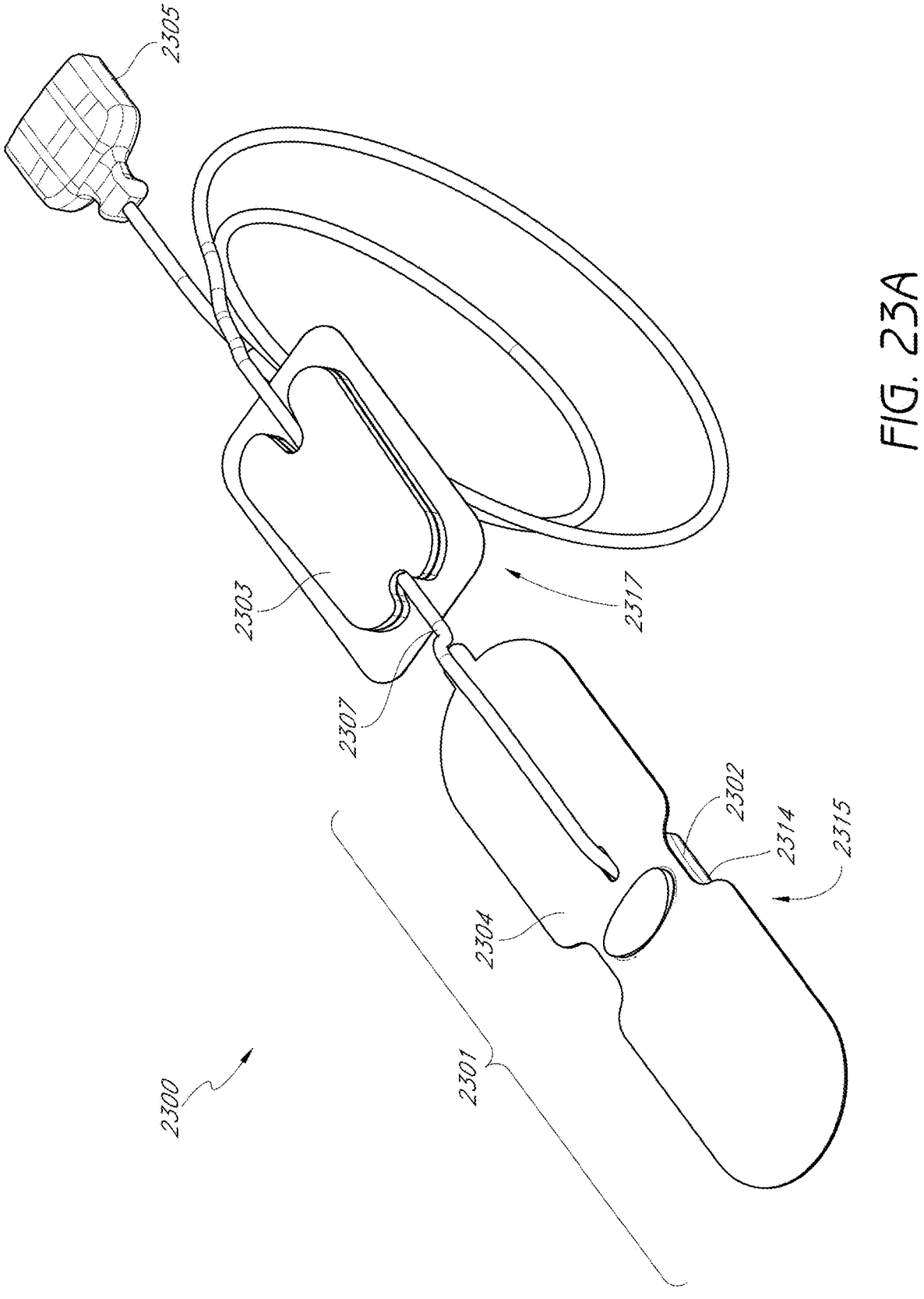
FIG. 23A is a top perspective view illustrating portions of a sensor assembly in accordance with another embodiment of the disclosure.

FIG. 23A is a top perspective view illustrating portions of another embodiment of a sensor system 2300 including a sensor assembly 2301 suitable for use with any of the physiological monitors shown in FIGS. 1A-C. The sensor assembly 2301 includes a sensor 2315, a cable assembly 2317 and a connector 2305. The sensor 2315, in one embodiment, includes a sensor subassembly 2302 and an attachment subassembly 2304. The cable assembly 2317 of one embodiment includes a cable 2307 and a patient anchor 2303. The various components are connected to one another via the sensor cable 2307. The sensor connector 2305 can be removably attached to a physiological monitor (not shown), such as through a monitor cable, or some other mechanism. In one embodiment, the sensor assembly 2301 communicates with a physiological monitor via a wireless connection.

The sensor system 2300 and certain components thereof may be generally similar in structure and function or identical to other sensor systems described herein, such as, for example, the sensor systems 100, 1900 described herein with respect to FIGS. 1 and 19-22, respectively.

For example, the sensor system 2300 may include an electrical shielding barrier (FIGS. 23D-E) including one or more layers which form a Faraday cage around an piezoelectric sensing element (FIGS. 23D-E), and which distribute external electrical noise substantially equally to electrical poles of the piezoelectric sensing element. The shielding barrier or portions thereof of some embodiments can flexibly conform to the surface shape of the piezoelectric element as the surface shape of the piezoelectric element changes, thereby improving the shielding and sensor performance.

The sensor system 2300 may further include an acoustic coupler 2314 which can including a bump positioned to apply pressure to the sensing element so as to bias the sensing element in tension. The acoustic coupler can also provide electrical isolation between the patient and the electrical components of the sensor, beneficially preventing potentially harmful electrical pathways or ground loops from forming and affecting the patient or the sensor.

The sensor system 2309 may also include an attachment subassembly 2304. In one embodiment, the attachment subassembly 2304 is configured to press the sensor against the patient's skin with a pre-determined amount of force. The attachment subassembly 2304 can be configured act in a spring-like manner to press the sensor 2300 against the patient. The attachment subassembly 2304 can also be configured such that movement of the sensor 2300 with respect to the attachment subassembly 2304 does not cause the attachment subassembly 2304 to peel off or otherwise detach from the patient during use.

Additionally, in some embodiments, a patient anchor 2303 is provided which advantageously secures the sensor 2315 to the patient at a point between the ends of the cable 2307. Securing the cable 2307 to the patient can decouple the sensor assembly 2300 from cable 2307 movement due to various movements such as accidental yanking or jerking on the cable 2307, movement of the patient, etc. Decoupling the sensor assembly 2300 from cable 2307 movement can significantly improve performance by eliminating or reducing acoustical noise associated with cable 2307 movement. For example, by decoupling the sensor 2300 from cable movement, cable movement will not register or otherwise be introduced as noise in the acoustical signal generated by the sensor 2300.

The shielding barrier, acoustic coupler 2314, attachment subassembly 2304, and patient anchor 2303 may be generally similar in certain structural and functional aspects to the shielding barrier, acoustic coupler 1914, attachment subassembly 1904, and patient anchor 1903 of other sensor systems described herein, such as the sensor system 1900 described with respect to FIGS. 19A-22B, for example.

Figure 23B:
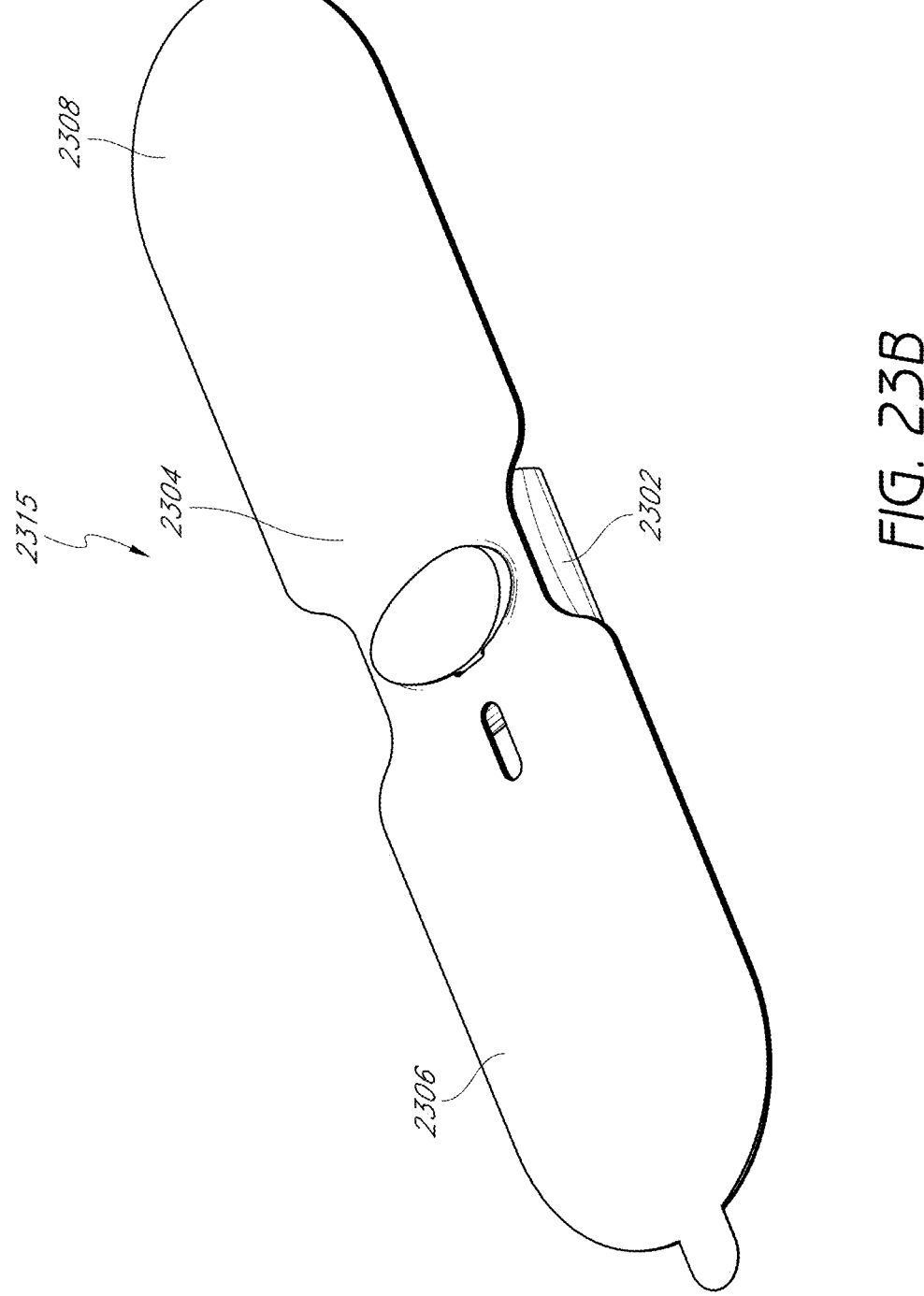
FIGS. 23B-23C are top and bottom perspective views, respectively, of a sensor including a sensor subassembly and an attachment subassembly of FIG. 23A.
Figure 23C:
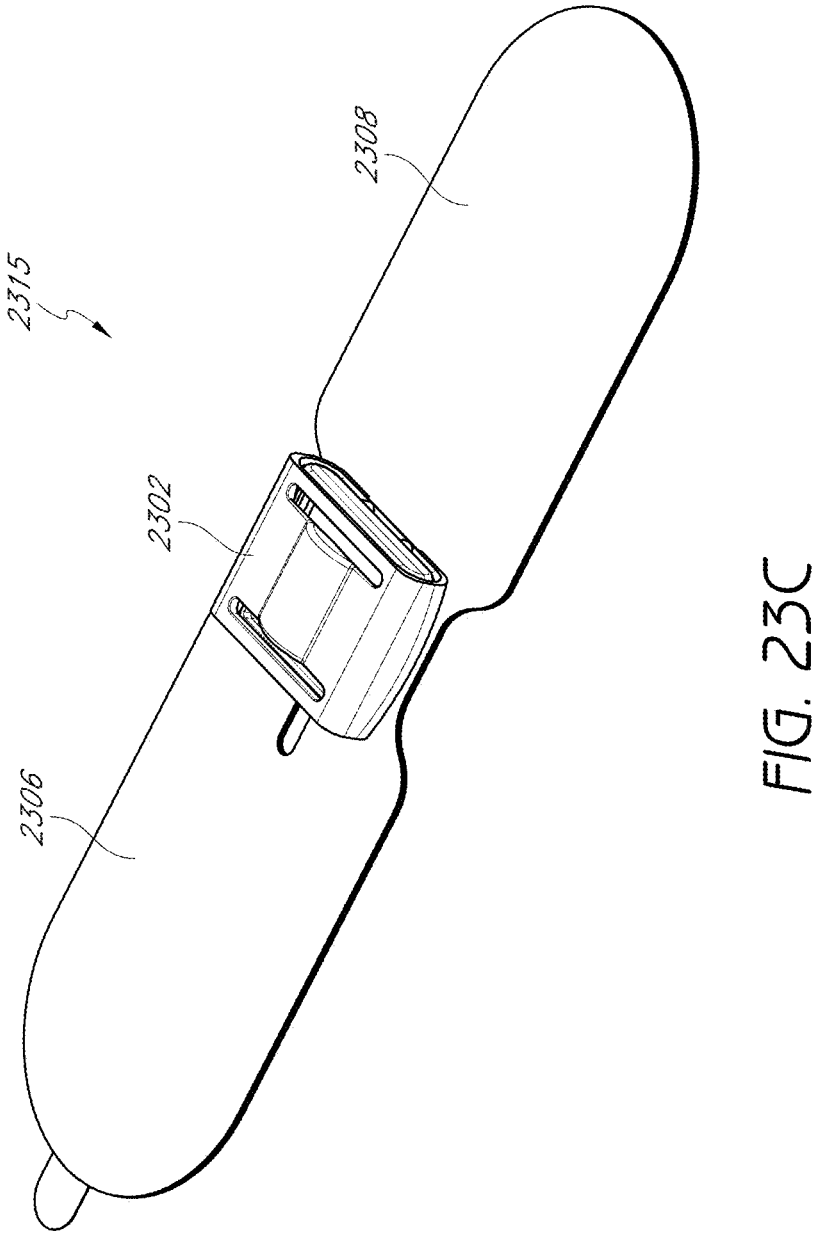

FIGS. 23B-C are top and bottom perspective views of a sensor including subassembly 2302 and an attachment subassembly 2304 in accordance with another embodiment of the present disclosure. The attachment subassembly 2304 generally includes lateral extensions symmetrically placed about the sensor subassembly 2302. An embodiment of a similar attachment subassembly is described in detail with respect to FIG. 10.

Figure 23D:
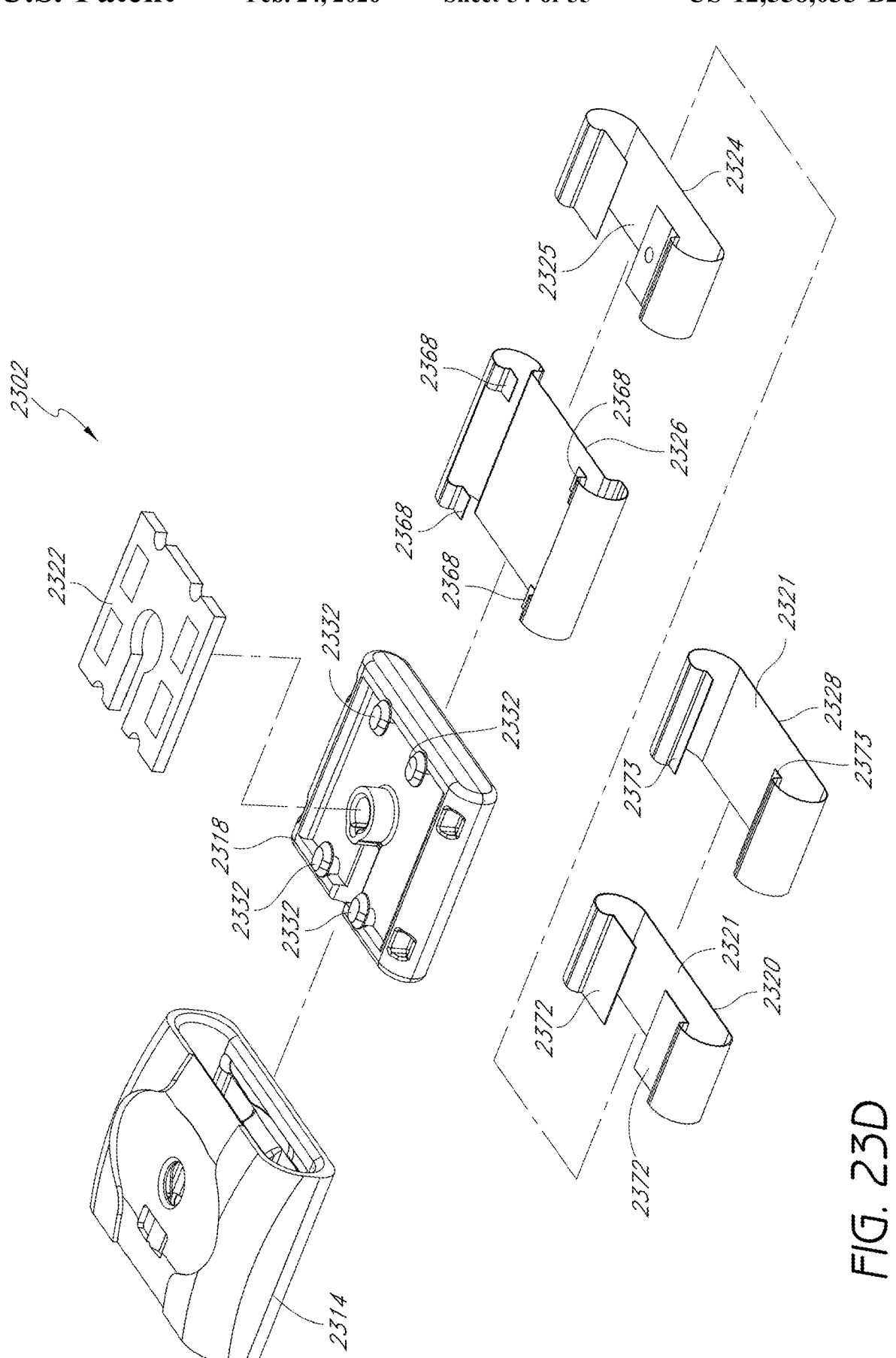
FIGS. 23D-23E are top and bottom exploded, perspective views, respectively, of the sensor subassembly of FIGS. 23A-C.
Figure 23E:
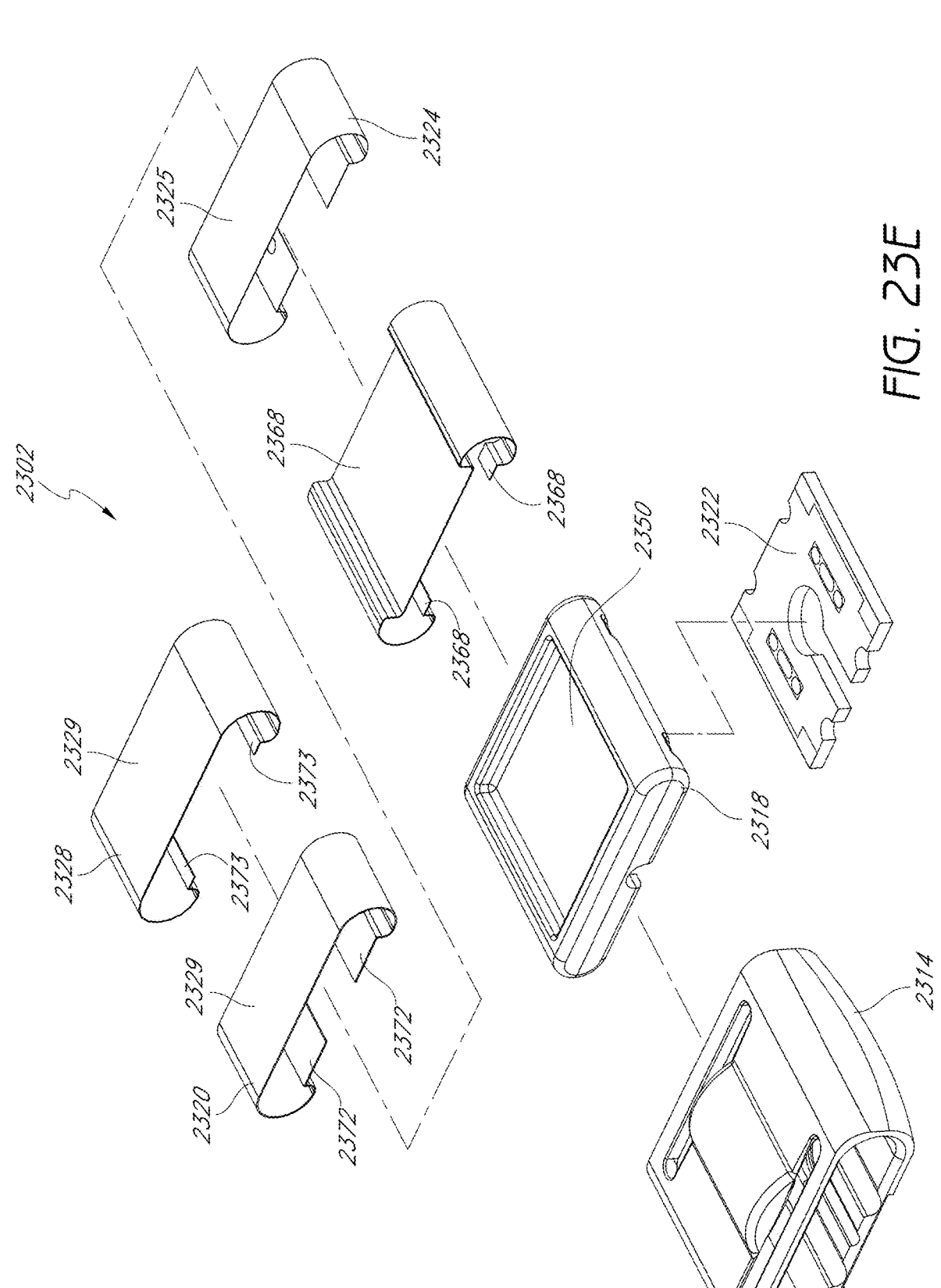

FIG. 23D-E are top and bottom exploded, perspective views, respectively, of the sensor subassembly of FIGS. 23A-C. The frame 2318 generally supports the various components of the sensor such as the piezoelectric element, electrical shielding barrier, attachment element and other components. The sensor subassembly 2302 includes an acoustic coupler 2314, sensing element 2320, adhesive layer 2324, and first and second electrical shielding layers 2326, 2328 which may, in certain aspects, be generally similar in structure and function to the acoustic coupler 1914, sensing element 1920, adhesive layer 1924, and first and second electrical shielding layers 1926, 1928 of FIGS. 19A-19E, for example.

As shown, and unlike the embodiment shown in FIGS. 19A-E, the adhesive layer 2324 of FIG. 23D-E stretches straight across the frame 2328 without conforming to the surface 2350 on the underside of the frame 2318. Thus, the sensing element 2320 is sandwiched between the adhesive layer 2324 and the outer shielding layer 2328. The adhesive layer 2324 includes adhesive over its entire outer surface which is in contact with the sensing element 2320. Moreover, the copper layer 2328 may also include an adhesive on its interior surface which contacts the other side of the sensing element 2320. As such, the adhesive layer 2324 and the shielding layer 2328 bond to opposite sides of the sensing element 2320, sandwiching and creating a seal around it. This sandwiching and sealing of the sensing element 2320 improves the liquid resistivity of the sensor subassembly 2302 by impeding water or water vapors (e.g., from sweat or other sources) from ingressing and contacting the sensing element 2320. Thus, the sandwiching of the sensing element 2320 protects the sensor 2302 from undesired effects such as electrical shorting due to liquid ingress. In one embodiment, the sensor 2302 is IPX1 compliant.

The planar portion 2325 of the adhesive layer 2324, along with the corresponding planar portions 2321, 2329 of the sensing element 2320 and outer shielding layer 2328, are configured to move with respect to the cavity defined by the underside of the frame 2318 in response to vibrations. The adhesive layer 2324 generally includes adhesive on all of its surface area except for the interior surface of the planar portion 2325. As such, the adhesive layer 2324 is securely bonded in place while the planar portion 2325 can move freely with respect to the cavity during operation without sticking. Moreover, because the interior portion of the planar portion 2325 is non-adhesive, foreign material such as dust particles will generally not stick to the non-adhesive planar portion 2325, improving sensor operation.

Similar to the frame 1918 of FIG. 19D, the frame 2318 includes four locking posts 2332. However, the posts 2332 of FIG. 23D are shown in a locked or liquefied configuration, unlike the posts 1932 illustrated in FIG. 19D.

As shown in FIG. 23D, the shielding layers 2326, 2328 include flap portions 2368, 2373 which conform to the frame 2318 and sit underneath the PCB 2322 in an assembled configuration. Similarly, the sensing element 2320 of the sensor subassembly 2302 includes a flap portion 2372 which conforms to the frame 2318 and sits underneath the PCB 1922. Upon welding of the locking posts 2332, the PCB 2322 is pressed downwards into physical and electrical contact with the flap portions 2368, 2373, 2372 of the shielding layers 2326, 2328 and sensing element 2320. As such, because the flaps 2368, 2373, 2372 are configured to sit underneath the PCB 2322, they are held in place in a pressure fit without soldering, improving manufacturability.

Information Element

In addition, the sensor assembly can include any of a variety of information elements, such as readable and/or writable memories. Information elements can be used to keep track of device usage, manufacturing information, duration of sensor usage, compatibility information, calibration information, identification information, other sensor, physiological monitor, and/or patient statistics, etc. The information element can communicate such information to a physiological monitor. For example, in one embodiment, the information element identifies the manufacturer, lot number, expiration date, and/or other manufacturing information. In another embodiment, the information element includes calibration information regarding the multi-parameter sensor. Information from the information element is provided to the physiological monitor according to any communication protocol known to those of skill in the art. For example, in one embodiment, information is communicated according to an I²C protocol. The information element may be provided on or be in electrical communication with the PCB 1922. In various embodiments, the information element can be located in another portion of the sensor assembly. For example, in one embodiment, the information element is provided on a cable connected to the PCB 1922. The information element may further be located on the sensor connector 1905, the attachment subassembly 1904, or some other part of the sensor assembly.

The information element can include one or more of a wide variety of memory devices known to an artisan from the disclosure herein, including an EPROM, an EEPROM, a flash memory, a combination of the same or the like. The information element can include a read-only device such as a ROM, a read and write device such as a RAM, combinations of the same, or the like. The remainder of the present disclosure will refer to such combination as simply EPROM for case of disclosure; however, an artisan will recognize from the disclosure herein that the information element can include the ROM, the RAM, single wire memories, combinations, or the like.

The information element can advantageously store some or all of a wide variety data and information, including, for example, information on the type or operation of the sensor, type of patient or body tissue, buyer or manufacturer information, sensor characteristics including calculation mode data, calibration data, software such as scripts, executable code, or the like, sensor electronic elements, sensor life data indicating whether some or all sensor components have expired and should be replaced, encryption information, monitor or algorithm upgrade instructions or data, or the like. In some embodiments, the information element can be used to provide a quality control function. For example, the information element may provide sensor identification information to the system which the system uses to determine whether the sensor is compatible with the system.

In an advantageous embodiment, the monitor reads the information element on the sensor to determine one, some or all of a wide variety of data and information, including, for example, information on the type or operation of the sensor, a type of patient, type or identification of sensor buyer, sensor manufacturer information, sensor characteristics including history of the sensor temperature, the parameters it is intended to measure, calibration data, software such as scripts, executable code, or the like, sensor electronic elements, whether it is a disposable, reusable, or multi-site partially reusable, partially disposable sensor, whether it is an adhesive or non-adhesive sensor, sensor life data indicating whether some or all sensor components have expired and should be replaced, encryption information, keys, indexes to keys or has functions, or the like monitor or algorithm upgrade instructions or data, some or all of parameter equations, information about the patient, age, sex, medications, and other information that can be useful for the accuracy or alarm settings and sensitivities, trend history, alarm history, sensor life, or the like.

TERMINOLOGY/ADDITIONAL EMBODIMENTS

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. An acoustic sensor system comprising:
first and second acoustic sensors arranged in a stack,
wherein the stack of the first and second acoustic sensors includes electrode layers on a top and a bottom of the stack that together are configured to form an electromagnetic noise shielding barrier.

2. The acoustic sensor system of claim 1, wherein the electrode layers comprise electrode coatings on sensing elements of the respective first and second acoustic sensors.

3. The acoustic sensor system of claim 2, wherein the sensing elements comprise piezoelectric elements.

4. The acoustic sensor system of claim 3, wherein the electrode layers are coupled to a common potential.

5. The acoustic sensor system of claim 4, wherein the stack of the first and second acoustic sensors further includes inner layers positioned between the sensing elements of the first and second acoustic sensors.

6. The acoustic sensor system of claim 5, wherein:
a first inner layer of the inner layers covers a first percentage of an inner surface area of a first sensing element of the sensing elements, and
a first electrode layer of the electrode layers covers a second percentage of an outer surface area of the first sensing element, the second percentage greater than the first percentage.

7. The acoustic sensor system of claim 6, wherein:
a second inner layer of the inner layers covers a third percentage of an inner surface area of a second sensing element of the sensing elements, and
a second electrode layer of the electrode layers covers a fourth percentage of an outer surface area of the second sensing element, the fourth percentage greater than the third percentage.

8. The acoustic sensor system of claim 7, wherein the first acoustic sensor produces a first signal in response to acoustic vibrations and provides the first signal to a noise attenuator, wherein the second acoustic sensor produces a second signal in response to acoustic vibrations and provides the second signal to the noise attenuator, and wherein the noise attenuator is responsive to the first and second signals to produce a reduced noise signal having a higher signal to noise ratio than either of the first or second signals.

9. The acoustic sensor system of claim 8, wherein the first and second electrode layers distribute electromagnetic noise incident on the acoustic sensor system substantially evenly between the first signal and the second signal.

10. The acoustic sensor system of claim 9, wherein the electromagnetic noise in the first signal is substantially in phase with the electromagnetic noise in the second signal.

11. The acoustic sensor system of claim 5, wherein the stack of the first and second acoustic sensors further includes an intermediate layer positioned between the first and second acoustic sensors, the intermediate layer configured electrically insulate the first and second acoustic sensors from one another.

12. The acoustic sensor system of claim 11, wherein the intermediate layer forms a substantially water resistant seal between the first and second acoustic sensors.

13. The acoustic sensor system of claim 12, wherein the intermediate layer is configured to at least partially bond the first and second acoustic sensors together such that mechanically active regions of the sensing elements move together in response to acoustic vibrations.

14. The acoustic sensor system of claim 5 further comprising:
a noise attenuator coupled to a first inner layer of the first acoustic sensor and a second inner layer of the second acoustic sensor, the noise attenuator configured to:
at least partially constructively combine a physiological signal component of a first signal output by a first acoustic sensing element and a physiological signal component of a second signal output by a second acoustic sensing element; and
at least partially destructively combine a noise component of the first signal output by the first acoustic sensing element and a noise component of the second signal output by the second acoustic sensing element.

15. The acoustic sensor system of claim 14, wherein the noise attenuator comprises at least one of: circuitry including an amplifier, a signal processor, or a general-purpose processor.

16. The acoustic sensor system of claim 15, wherein the noise attenuator is further configured to generate a reduced noise signal based on constructively combining the physiological signal components and destructively combining the noise components.

17. The acoustic sensor system of claim 16, wherein the reduced noise signal has a lower noise component than one or more of the first and second signals.

18. The acoustic sensor system of claim 17, wherein the noise attenuator generates the reduced noise signal using common-mode rejection.

19. A method comprising:
receiving signals from the acoustic sensor system according to claim 1 that is attachable to a patient and configured to provide signals responsive to acoustic vibrations indicative of one or more physiological parameters of the patient.

20. The method of claim 19, wherein the acoustic sensor system further includes a coupling bump configured to apply pressure to at least one of the first and second acoustic sensors to push at least a portion of the one of the first and second acoustic sensors into a cavity of the acoustic sensor system, and wherein the coupling bump is configured to transmit acoustic vibrations to the one of the first and second acoustic sensor through the acoustic coupling bump when the acoustic sensor system is attached to the patient.

\* \* \* \* \*